(12) United States Patent
Duff et al.

(10) Patent No.: US 6,706,478 B2
(45) Date of Patent: *Mar. 16, 2004

(54) DIAGNOSTICS AND THERAPEUTICS FOR DISEASES ASSOCIATED WITH AN IL-1 INFLAMMATORY HAPLOTYPE

(75) Inventors: Gordon W. Duff, Sheffield (GB); Angela Cox, Sheffield (GB); Nicola Jane Camp, Salt Lake City, UT (US); Francesco S. di Giovine, Sheffield (GB)

(73) Assignee: Interleukin Genetics, Inc., Waltham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/845,129

(22) Filed: Apr. 27, 2001

(65) Prior Publication Data

US 2002/146700 A1 Oct. 10, 2002

Related U.S. Application Data

(63) Continuation of application No. 09/345,217, filed on Jun. 30, 1999, now Pat. No. 6,268,142, which is a continuation of application No. PCT/GB98/01481, filed on May 21, 1998.

(30) Foreign Application Priority Data

May 29, 1997 (GB) ............................................. 9711040

(51) Int. Cl.[7] .......................... C12Q 1/68; C12P 19/34; A61K 38/00; C07H 21/04
(52) U.S. Cl. ...................... 435/6; 435/91.1; 435/91.2; 536/22.1; 536/23.1; 536/25.3; 514/12
(58) Field of Search .................. 435/6, 91.2; 536/22.1, 536/23.1, 25.3; 514/12

(56) References Cited

U.S. PATENT DOCUMENTS

| 5,582,979 A | * | 12/1996 | Weber ........................... 435/6 |
| 5,681,940 A | * | 10/1997 | Wang ......................... 536/22.1 |
| 5,686,246 A |  | 11/1997 | Kornman et al. ............... 435/6 |
| 5,698,399 A | * | 12/1997 | Duff .............................. 435/6 |
| 5,780,587 A | * | 7/1998 | Potter ......................... 530/326 |
| 5,993,817 A | * | 11/1999 | Yoneda ................... 424/158.1 |
| 6,268,142 B1 | * | 7/2001 | Duff .............................. 435/6 |

FOREIGN PATENT DOCUMENTS

| WO | WO 97/25445 | 7/1997 |
| WO | WO 98/15653 | 4/1998 |
| WO | WO 98/44150 | 10/1998 |
| WO | WO 98/54359 | 12/1998 |

OTHER PUBLICATIONS

Bloque et al., "Allelic polymorphism in IL–1B and IL–1 receptor antagonist . . ." Clin Exp. Immunol. 102: 379–383. 1995.*
Bailly et al.; " An Intronic Polymorphic Repeat Sequence Modulates Interleukin–1 Alpha Gene Regulation", Molecular Immunology 33(11/12):999–1006 (1996).
Bailly et al.; " Genetic Polymorphism of Human Interleukin–1α", Eur. J. Immunol. 23: 1240–1245 (1993).

(List continued on next page.)

Primary Examiner—Gary Benzion
Assistant Examiner—Arun Kr. Chakrabarti
(74) Attorney, Agent, or Firm—Ivan R. Elrifi, Esq.; Mintz, Levin, Cohn, Ferris, Glovsky and Popeo, P.C.; Cynthia A. Kozakiewicz

(57) ABSTRACT

Methods and kits for determining whether a subject has or is predisposed to developing a disease which is associated with IL-1 polymorphisms and assays for identifying therapeutics for treating and/or preventing the development of these diseases are provided.

40 Claims, 15 Drawing Sheets

OTHER PUBLICATIONS

Blakemore et al.; " Association of Graves' Disease with an Allele of the Interleukin–1 Receptor Antogonist Gene", Journal of Clinical Endocrinology and Metabolism 80(1): 111–115 (1995).

Blakemore et al.; " Interleukin–1 Receptor Antagonist Gene Polymorphism as a Disease Severity Factor in Systemic Lupus Erythematosus", Arthritis & Rheumatism 37(9): 1380–1385 (Sep. 1994).

Clay et al.; " Interleukin–1 Receptor Antagonist Gene Polymorphism Association with Lichen Sclerosus", Hum. Genet. 94: 407–410 (1994).

Copeman et al.; "Linkage Disequilibrium Mapping of a Type 1 Diabetes Susceptibility Gene (IDDM7) to Chromosome 2q31–q33", Nature Genetics 9: 80–85(1995).

Cork et al.; " Genetic Control of Cytokines ; Cytokine GEne Polymorphisms in Alopecia areata", Dermatologic Clinics 14(4): 671–678 (Oct. 1996).

Cox et al.; " An Analysis of Linkage Disequilibrium in the Interleukin–1 Gene Cluster, Using a Novel Grouping Method for Multiallelic Markers", Am. J. Hum. Genet. 62:1180–1188(1998).

Guash et al.; " Five Novel Intragenic Dimorphism in the Human Interleukin–1 Genes Combine to High Informativity", Cytokine 8(8): 598, (1996).

Hart and Kornman; " Genetic Factors in the Pathogenesis of Periodontitis", Preiodontology 14: 202–215 (2000).

Hurme et al.; " IL–1 Receptor Antagonist (IL–1Ra) Plasma Levels are co–ordinately Regulated by Both IL–1Ra and IL–1B Genes", European J. Immunol., 28:2598, (1998).

Kimble et al.; " Interleukin–1 Receptor Antagonist Decreases Bone Loss and Bone Resoption in Ovariectomized Rats", J. Clin. Invest. 93: 1959, (1994).

Kornman, KS et al.;" The Interleukin–1 Genotype as a Severity Factor in Adult Periodontal Disease", J. Clin. Periodontol. 24: 72–77 (1997).

Lander and Schork; "Genetic Dissection of Complex Traits", Science 265: 2037–2048 (Sep. 30, 1994).

Mansfield et al.; "Novel Genetic Association Between Ulcerative Colitis and the Anti–inflammatory Cytokine Interleukin–1 Receptor Antagonist", Gastroenterology 106: 637–642 (1994).

McDowell et al.;"A Genetic Association Between Juvenile Rheumatoid Arthritis and a Novel Interleukin–1α Polymorphism", Arthritis and Rheumatism 38(2): 221–228 (Feb. 1995).

McGuire et al.;"Variation in the TNF–α Region Associated with Susceptibility to Cerebral Malaria", Nature 371: 508–511 (Oct. 6, 1994).

Nicklin et al.;"A Physical Map of the Region Encompassing the Human Interleukin–1α, Interleukin–1β, and Interleukin–1 Receptor Antagonist Genes", Genomics 19: 382–384 (1994).

Pociot et al.; "Taql Polymorphism in the Human Interleukin–1β (IL–1β) Gene Correlates with IL–1β Secretion in Vitro ", European Journal of Clinical Investigation 22: 396–402 (1992).

Andus, T. et al., "IL–1ra genotype 2 is associated with reduced IL–1ra in colonic mucosa", Gastroenterology, 108:A3070 (1996).

Andus, T. et al., "Imbalance of the interleukin 1 system in colonic mucosa—association with intestinal inflammation and interleukin 1 receptor antagonist genotype 2", Gut, 41:651–657 (1997).

Bioque, G. et al., "Allelic polymorphism in IL–1β and IL–1 receptor antagonist genes in inflammatory bowel disease", Clinical and experimental Immunology, 102:379–383 (1995).

Blakemore, A. et al., "Interleukin–1 receptor antagonist allele (IL1RN*2) associated with neuropathy in diabetes mellitus", Human Genetics, 97:374 (1996).

Clay, F. et al., "Novel Interleukin–1 receptor antagonist exon polymorphisms and their use in allele–specific mRNA assesment", Human Genetics, 97:723–726 (1996).

Cork, M.J. et al., "An allele in of the interleukin–1 receptor antagonist as a genetic severity factor in Alopecia areata", J. Investigative Dermatology, 104:15S–16S (1995).

Cox, A. et al., "An analysis of Linkage Disequilibrium in the Interleukin–1 Gene Cluster, Using a Novel Grouping Method for Multiallelic Markers", Am. J. Hum. Genet., 62:1180–1188 (1998).

Crusius, J.B.A. et al., "Interleukin–1 receptor antagonist gene polymorphism and multiple sclerosis", Lancet, 346:979–980 (1995).

Cuddihy, R. et al., "Lack of association between alleles of interleukin–1 alpha and interleukin–1 receptor antagonist genes and Graves' disease in a North American Caucasian population" J. of Clinical Endocrinology & Metabolism, 81;4476–4478 (1996).

Diehl, S. et al., "Interleukin–1 genotypes and the risk of early onset periodontitis– a family based study of linkage disequilibrium", J. Dental Research, 77 Suppl. :195 (1998).

Duerr, R.H. et al., "Association between ulcerative colitis and a polymorphism in intron 2 of the interleukin–1 receptor antagonist gene", Gastroenterology, 108:A812 (1995).

Eastell, R. et al., "IL–1 receptor antagonist genotype as a predictor of bone loss in postmenopausal women", Bone, 23 (5s):S375 (1998).

Eastell, R. et al., "IL–1 receptor antagonist genotype is associated with a low bone mineral density in postmenopausal women", Bone, 23 (5S):S375 (1998).

Engebretson, S.P. et al., "The influence of interleukin–1 (IL–1) gene polymorphisms on expression of IL–1β and tumor necrosis factor alpha (TNFα) in periodontal tissue and gingival crevicular fluid", J. Periodontology (1998).

Freedman, B. I. et al., "Genetic linkage analysis of growth factor loci and end–stage renal disease in African Americans", Kidney International, 51(3):819–825 (1997).

Friedlander, R. M. et al., "Inhibition of ICE slows ALS in mice", Nature, 388:31 (1997).

Gore, E.A. et al., "Interleukin–1β In allele 2: association with disease status in perio", J. Clin. Periodontology, 25:781–785 (1998).

Herren, L. T. et al., "IL–1 receptor antagonist as a potential new therapeutic agent for osteoporosis: a computer simulation model of bone remodeling and osteoporosis", Bone, 23 (5S): S620 (1998).

Harai, R, et al. Production of mice deficient in genes for interleukin (IL)–1 alpha, IL–1 beta IL–1 alpha/beta, IL–1 receptor antagonist shows that IL–1 beta is crucial in turpentine–induced fever development and glucocorticoid secretion, J. Experimental Medicine, 187:1463–1475 (1998).

Hurme, M. et al., "Polymorphisms of the IL–1 gene complex in Epstein–Barr virus seronegative and seropositive adult blood donors", Scandinavian J. of Immunology, 48:219–222 (1998).

Keen, et al., "Allelic variation at the interleukin–1 receptor antagonist gene is associated with early postmenopausal bone loss at the spine", *Bone*, 23:367–371 (1998).

Louis, E. et al., "Cytokine gene polymorphism in inflammatory bowel diseases", *Gut*, 39:705–710 (1996).

Mandrup–Poulsen T. et al., "Monokine antagonism is reduced in patients with IDDM", *Diabetes*, 43:1242–1247 (1994).

McGuire M.K. et al., "Prognosis versus actual outcome. IV. The effectiveness ao clinical parameters and IL–1 genotype in accurately predicting prognosis and tooth survival", *J. Periodontology*, (1998).

Muhlberg, T. et al, "Lack of Association of Graves' Disease with the A2 Allele of the linterleukin–1 Receptor Antagonist in a White European Population", *European J. of Endocrinology*, 138:686–690 (1998).

deleted from list.

Okada, H. et al., "Cytokine expression in periodontal health and disease", *Critical Reviews in Oral Biology & Medicine*, 9:248–266 (1998).

Stokkers, P.C.F. et al., "Five genetic markers in the interleukin–1 family in relation to inflammatory bowel disease", Gut, 43:33–39 (1998).

Suzuki, H. et al., "Interleukin–1 receptor antagonist gene polymorphism in Japanese patients with systemic lupus erythemateous", *Concise Communications, 389–390*.

Tarlow, J. et al., "Association between interleukin–1 receptor antagonist (IL–1ra) gene polymorphism and early and and late–onset psoriasis", *British Journal of Dermatology*, 148–149 (1997).

Tarlow, J.K. et al., "Severity of *Alopecia areata* is associated with a polymorphism in the interleukin–1 receptorantagonist gene", J. Invest. Dermatol. 103:387–390 (1994).

Tarnow, L. et al., "Polymorphisms in the interleukin–1 gene cluster do not contribute to the genetic susceptibility of diabetic neuropathy in Caucasian patients with IDDM", *Diabetes*, 46:1075–1076 (1997).

Clark et al.; "Genomic Sequence for Human Prointerleukin I beta: Possible Evolution from the a Reverse Transcribed Prointerleukin alpha Gene ", Nucleic Acids Research, 14 (20): 7897–7914 (1986).

DI Giovine et al., "Single Base Polymorphism at –511 in the Human Interleukin–1β Gene (IL 1β )", Human Molecular Genetics, 1 (6): 450 (Sep. 1992).

Clay, et al., " Novel Interleukin–1 Receptor Antagonist *Exon Polymorphisms* and their use in Allele–specific mRNA Assessement", Hum. Genet. 97 (6): 723–726 (Jun. 1996).

Duff, " Molecular Genetics of Cytokines", The Cytokine Handbook(19940 $2^{nd}$ ed., chap. 2 :21–30.

International Search Report Completed on Apr. 4, 2001 and mailed on Jul. 12, 2001.

* cited by examiner

```
-1437 AAGCTTCTAC CCTAGTCTGG TGCTACACTT ACATTGCTTA CATCCAAGTG TGGTTATTTC
-1377 TGTGGCTCCT GTTATAACTA TTATAGCACC AGGTCTATGA CCAGGAGAAT TAGACTGGCA
-1317 TTAAATCAGA ATAAGAGATT TTGCACCTGC AATAGACCTT ATGACACCTA ACCAACCCCA
-1257 TTATTTACAA TTAAACAGGA ACAGAGGGAA TACTTTATCC AACTCACACA AGCTGTTTTC
-1197 CTCCCAGATC CATGCTTTTT TGCGTTTATT ATTTTTTAGA GATGGGGCT TCACTATGTT
-1137 GCCCACACTG GACTAAAACT CTGGGCCTCA AGTGATTGTC CTGCCTCAGC CTCCTGAATA
-1077 GCTGGGACTA CAGGGGCATG CCATCACACC TAGTTCATTT CCTCTATTTA AAATATACAT
-1017 GGCTTAAACT CCAACTGGGA ACCCAAAACA TTCATTTGCT AAGAGTCTGG TGTTCTACCA
 -957 CCTGAACTAG GCTGGCCACA GGAATTATAA AAGCTGAGAA ATTCTTTAAT AATAGTAACC
 -897 AGGCAACATC ATTGAAGGCT CATATGTAAA AATCCATGCC TTCCTTTCTC CCAATCTCCA
 -837 TTCCCAAACT TAGCCACTGG TTCTGGCTGA GGCCTTACGC ATACCTCCCG GGGCTTGCAC
 -777 ACACCTTCTT CTACAGAAGA CACACCTTGG GCATATCCTA CAGAAGACCA GGCTTCTCTC
 -717 TGGTCCTTGG TAGAGGGCTA CTTTACTGTA ACAGGGCCAG GGTGGAGAGT TCTCTCCTGA
 -657 AGCTCCATCC CCTCTATAGG AAATGTGTTG ACAATATTCA GAAGAGTAAG AGGATCAAGA
 -597 CTTCTTTGTG CTCAAATACC ACTGTTCTCT TCTCTACCCT GCCCTAACCA GGAGCTTGTC
 -537 ACCCCAAACT CTGAGGTGAT TTATGCCTTA ATCAAGCAAA CTTCCCTCTT CAGAAAAGAT
 -477 GGCTCATTTT CCCTCAAAAG TTGCCAGGAG CTGCCAAGTA TTCTGCCAAT TCACCCTGGA
 -417 GCACAATCAA CAAATTCAGC CAGAACACAA CTACAGCTAC TATTAGAACT ATTATTATTA
 -357 ATAAATTCCT CTCCAAATCT AGCCCCTTGA CTTCGGATTT CACGATTTCT CCCTTCCTCC
 -297 TAGAAACTTG ATAAGTTTCC CGCGCTTCCC TTTTTCTAAG ACTACATGTT TGTCATCTTA
 -237 TAAAGCAAAG GGGTGAATAA ATGAACCAAA TCAATAACTT CTGGAATATC TGCAAACAAC
 -177 AATAATATCA GCTATGCCAT CTTTCACTAT TTTAGCCAGT ATCGAGTTGA ATGAACATAG
 -117 AAAAATACAA AACTGAATTC TTCCCTGTAA ATTCCCCGTT TTGACGACGC ACTTGTAGCC
  -57 ACGTAGCCAC GCCTACTTAA GACAATTACA AAAGGCGAAG AAGACTGACT CAGGCTTAAG
    4 CTGCCAGCCA GAGAGGGAGT CATTTCATTG GCGTTTGAGT CAGCAAAGGT ATTGTCCTCA
   64 CATCTCTGGC TATTAAAGTA TTTTCTGTTG TTGTTTTTCT CTTTGGCTGT TTTCTCTCAC
  124 ATTGCCTTCT CTAAAGCTAC AGTCTCTCCT TTCTTTTCTT GTCCCTCCCT GGTTTGGTAT
  184 GTGACCTAGA ATTACAGTCA GATTTCAGAA AATGATTCTC TCATTTTGCT GATAAGGACT
  244 GATTCGTTTT ACTGAGGGAC GGCAGAACTA GTTTCCTATG AGGGCATGGG TGAATACAAC
  304 TGAGGCTTCT CATGGGAGGG AATCTCTACT ATCCAAAATT ATTAGGAGAA AATTGAAAAT
  364 TTCCAACTCT GTCTCTCTCT TACCTCTGTG TAAGGCAAAT ACCTTATTCT TGTGGTGTTT
  424 TTGTAACCTC TTCAAACTTT CATTGATTGA ATGCCTGTTC TGGCAATACA TTAGGTTGGG
  484 CACATAAGGA ATACCAACAT AAATAAAACA TTCTAAAAGA AGTTTACGAT CTAATAAAGG
  544 AGACAGGTAC ATAGCAAACT AATTCAAAGG AGCTAGAAGA TGGAGAAAAT GCTGAATGTG
  604 GACTAAGTCA TTCAACAAAG TTTTCAGGAA GCACAAAGAG GAGGGGCTCC CCTCACAGAT
  664 ATCTGGATTA GAGGCTGGCT GAGCTGATGG TGGCTGGTGT TCTCTGTTGC AGAAGTCAAG
  724 ATGGCCAAAG TTCCAGACAT GTTTGAAGAC CTGAAGAACT GTTACAGGTA GGAATAAGA
  784 TTTATCTCTT GTGATTTAAT GAGGGTTTCA AGGCTCACCA GAATCCAGCT AGGCATAACA
  844 GTGGCCAGCA TGGGGGCAGG CCGGCAGAGG TTGTAGAGAT GTGTACTAGT CCTGAAGTCA
  904 GAGCAGGTTC AGAGAAGACC CAGAAAAACT AAGCATTCAG CATGTTAAAC TGAGATTACA
  964 TTGGCAGGGA GACCGCCATT TTAGAAAAAT TATTTTTGAG GTCTGCTGAG CCCTACATGA
 1024 ATATCAGCAT CAACTTAGAC ACAGCCTCTG TTGAGATCAC ATGCCCTGAT ATAAGAATGG
 1084 GTTTTACTGG TCCATTCTCA GGAAAACTTG ATCTCATTCA GGAACAGGAA ATGGCTCCAC
 1144 AGCAAGCTGG GCATGTGAAC TCACATATGC AGGCAAATCT CACTCAGATG TAGAAGAAAG
 1204 GTAAATGAAC ACAAAGATAA AATTACGGAA CATATTAAAC TAACATGATG TTTCCATTAT
 1264 CTGTAGTAAA TACTAACACA AACTAGGCTG TCAAAATTTT GCCTGGATAT TTTACTAAGT
 1324 ATAAATTATG AAATCTGTTT TAGTGAATAC ATGAAAGTAA TGTGTAACAT ATAATCTATT
 1384 TGGTTAAAAT AAAAAGGAAG TGCTTCAAAA CCTTTCTTTT CTCTAAAGGA GCTTAACATT
 1444 CTTCCCTGAA CTTCAATTAA AGCTCTTCAA TTTGTTAGCC AAGTCCAATT TTTACAGATA
 1504 AAGCACAGGT AAAGCTCAAA GCCTGTCTTG ATGACTACTA ATTCCAGATT AGTAAGATAT
```

Fig. 3

```
1564 GAATTACTCT ACCTATGTGT ATGTGTAGAA GTCCTTAAAT TTCAAAGATG ACAGTAATGG
1624 CCATGTGTAT GTGTGTGACC CACAACTATC ATGGTCATTA AAGTACATTG GCCAGAGACC
1684 ACATGAAATA ACAACAATTA CATTCTCATC ATCTTATTTT GACAGTGAAA ATGAAGAAGA
1744 CAGTTCCTCC ATTGATCATC TGTCTCTGAA TCAGGTAAGC AAATGACTGT AATTCTCATG
1804 GGACTGCTAT TCTTACACAG TGGTTTCTTC ATCCAAAGAG AACAGCAATG ACTTGAATCT
1864 TAAATACTTT TGTTTTACCC TCACTAGAGA TCCAGAGACC TGTCTTTCAT TATAAGTGAG
1924 ACCAGCTGCC TCTCTAAACT AATAGTTGAT GTGCATTGGC TTCTCCCAGA ACAGAGCAGA
1984 ACTATCCCAA ATCCCTGAGA ACTGGAGTCT CCTGGGGCAG GCTTCATCAG GATGTTAGTT
2044 ATGCCATCCT GAGAAAGCCC CGCAGGCCGC TTCACCAGGT GTCTGTCTCC TAACGTGATG
2104 TGTTGTGGTT GTCTTCTCTG ACACCAGCAT CAGAGGTTAG AGAAAGTCTC CAAACATGAA
2164 GCTGAGAGAG AGGAAGCAAG CCAGCTGAAA GTGAGAAGTC TACAGCCACT CATCAATCTG
2224 TGTTATTGTG TTTGGAGACC ACAAATAGAC ACTATAAGTA CTGCCTAGTA TGTCTTCAGT
2284 ACTGGCTTTA AAAGCTGTCC CCAAAGGAGT ATTTCTAAAA TATTTTGAGC ATTGTTAAGC
2344 AGATTTTTAA CCTCCTGAGA GGGAACTAAT TGGAAAGCTA CCACTCACTA CAATCATTGT
2404 TAACCTATTT AGTTACAACA TCTCATTTTT GAGCATGCAA ATAAATGAAA AAGTCTTCCT
2464 AAAAAAATCA TCTTTTTATC CTGGAAGGAG GAAGGAAGGT GAGACAAAAG GGAGAGAGGG
2524 AGGGAAGCCT AATGAAACAC CAGTTACCTA AGACCAGAAT GGAGATCCTC CTCACTACCT
2584 CTGTTGAATA CAGCACCTAC TGAAAGAACT TTCATTCCCT GACCATGAAC AGCCTCTCAG
2644 CTTCTGTTTT CCTTCCTCAC AGAAATCCTT CTATCATGTA AGCTATGGCC CACTCCATGA
2704 AGGCTGCATG GATCAATCTG TGTCTCTGAG TATCTCTGAA ACCTCTAAAA CATCCAAGCT
2764 TACCTTCAAG GAGAGCATGG TGGTAGTAGC AACCAACGGG AAGGTTCTGA AGAAGAGACG
2824 GTTGAGTTTA AGCCAATCCA TCACTGATGA TGACCTGGAG GCCATCGCCA ATGACTCAGA
2884 GGAAGGTAAG GGGTCAAGCA CAATAATATC TTTCTTTTAC AGTTTTAAGC AAGTAGGGAC
2944 AGTAGAATTT AGGGGAAATT TAAACGTGGA GTCAGAATAA CAAGAAGACA CCAAGCATT
3004 AGTCTGGTAA CTATACAGAG GAAAATTAAT TTTATCCTT CTCCAGGAGG GAGAAATGAG
3064 CAGTGGCCTG AATCGAGAAT ACTTGCTCAC AGCCATTATT TCTTAGCCAT ATTGTAAAGG
3124 TCGTGTGACT TTTAGCCTTT CAGGAGAAAG CAGTAATAAG ACCACTTACG AGCTATGTTC
3184 CTCTCATACT AACTATGCCT CCTTGGTCAT GTTACATAAT CTTTTCGTGA TTCAGTTTCC
3244 TCTACTGTAA AATGGAGATA ATCAGAATCC CCCACTCATT GGATTGTGT AAAGATTAAG
3304 AGTCTCAGGC TTTACAGACT GAGCTAGCTG GGCCCTCCTG ACTGTTATAA AGATTAAATG
3364 AGTCAACATC CCCTAACTTC TGGACTAGAA TAATGTCTGG TACAAAGTAA GCACCCAATA
3424 AATGTTAGCT ATTACTATCA TTATTATTAT TATTTTATTT TTTTTTTTTG AGATGGAGTC
3484 TGGCTCTGTC ACCCAGGCTG GAGTGCAGTG GCACAATCTC GGCTCACTGC AAGCTCTGCC
3544 TCCTGGGTTC ATGCCATTCT CCTGCCTCAG CCTCCCGAGT AAGCTGGGAA TACAGGCACC
3604 CGCCACTGTT CCCGGCTAAT TTTTTGTATT TTTAGTAGAG ACGGAGTTTC ACCGTGGTCT
3664 CCATCTCCTC GTGATCCACC CACCTTGGCC TCCCAAAGTG CCGGGATTAC AGGCGTGAGC
3724 CACCGCGCCC GGCCTATTAT TATTATTATT ACTACTACTA CTACCTATAT GAATACTACC
3784 AGCAATACTA ATTTATTAAT GACTGGATTA TGTCTAAACC TCACAAGAAT CCTACCTTCT
3844 CATTTTACAT AAAAGGAAAC TAAGCTCATT GAGATAGGTA AACTGCCCAA TGGCATACAT
3904 CTGTAAGTGG GAGAGCCTCA AATCTAATTC AGTTCTACCT GAGTAAAAAA ATCATGGTTT
3964 CTCCTCCATC CCTTTACTGT ACAAGCCTCC ACATGAACTA TAAACCCAAT ATTCCTGTTT
4024 TTAAGATAAT ACCTAAGCAA TAACGCATGT TCACCTAGAA GGTTTTAAAA TGTAACAAAA
4084 TATAAGAAAA TAAAAATCAC TCATATCGTC AGTGAGAGTT TACTACTGCC AGCACTATGG
4144 TATGTTTCCT TAAAATCTTT GCTATACACA TACCTACATG TGAACAAATA TGTCTAACAT
4204 CAAGACCACA CTATTTACAA CTTTATATCC AGCTTTTCTT ACTTAGCAAT GTATTGAGGA
4264 CATTTTAGAG TGCCCGTTTT TCACCATTAT AAGCAATGCA ACAATGAACA TCTGTATAAA
4324 TAAATATTCA TTTCTCTCAC CCTTTATTTC CTTAGAATAT ATTCCTAGAA GTAGAATTTC
4384 CCAGAGCCAT GAGGATTGT GACGCTATTG ATATGTGCCA CTTTGCACTC TCTGTGACAT
4444 ATATAATTAT TTTTAATGCA TTCATTTTTT TCTCAGAGTG CATTCGTTTG AAAACATAGA
4504 CGGGAAATAC TGGTAGTCTT CCTTGTCAGT TAGAAACACC CAAACAATGA AAATGAAAA
```

Fig. 3 (cont.)

```
4564 AGTTGCACAA ATAGTCTCTA AAAACAATGA AACTATTGCC TGAGGAATTG AAGTTTAAAA
4624 AGAAGCACAT AAGCAACAAC AAGGATAATC CTAGAAAACC AGTTCTGCTG ACTGGGTGAT
4684 TTCACTTCTC TTTGCTTCCT CATCTGGATT GGAATATTCC TAATACCCCC TCCAGAACTA
4744 TTTTCCCTGT TTGTACTAGA CTGTGTATAT CATCTGTGTT TGTACATAGA CATTAATCTG
4804 CACTTGTGAT CATGGTTTTA GAAATCATCA AGCCTAGGTC ATCACCTTTT AGCTTCCTGA
4864 GCAATGTGAA ATACAACTTT ATGAGGATCA TCAAATACGA ATTCATCCTG AATGACGCCC
4924 TCAATCAAAG TATAATTCGA GCCAATGATC AGTACCTCAC GGCTGCTGCA TTACATAATC
4984 TGGATGAAGC AGGTACATTA AAATGGCACC AGACATTTCT GTCATCCTCC CCTCCTTTCA
5044 TTTACTTATT TATTTATTTC AATCTTCTG CTTGCAAAAA ACATACCTCT TCAGAGTTCT
5104 GGGTTGCACA ATTCTTCCAG AATAGCTTGA AGCACAGCAC CCCCATAAAA ATCCCAAGCC
5164 AGGGCAGAAG GTTCAACTAA ATCTGGAAGT TCCACAAGAG AGAAGTTTCC TATCTTTGAG
5224 AGTAAAGGGT TGTGCACAAA GCTAGCTGAT GTACTACCTC TTTGGTTCTT TCAGACATTC
5284 TTACCCTCAA TTTTAAAACT GAGGAAACTG TCAGACATAT TAAATGATTT ACTCAGATTT
5344 ACCCAGAAGC CAATGAAGAA CAATCACTCT CCTTTAAAAA GTCTGTTGAT CAAACTCACA
5404 AGTAACACCA AACCAGGAAG ATCTTTATTA TCTCTGATAA CATATTTGTG AGGCAAAACC
5464 TCCAATAAGC TACAAATATG GCTTAAAGGA TGAAGTTTAG TGTCCAAAAA CTTTTATCAC
5524 ACACATCCAA TTTTCATGGC GGACATGTTT TAGTTTCAAC AGTATACATA TTTTCAAAGG
5584 TCCAGAGAGG CAATTTGCA ATAAACAAGC AAGACTTTTT CTGATTGGAT GCACTTCAGC
5644 TAACATGCTT TCAACTCTAC ATTTACAAAT TATTTTGTGT TCTATTTTTC TACTTAATAT
5704 TATTTCTGCA ATTTTCCCAA TATTGACATC GTGTATGTAT TTGCCATTTT TAATATCACT
5764 AGACAATTCA ATCAGGTTGC TACGTTGGTC CCTTGGGTTT ACTCTAAATA GCTTGATTGC
5824 AAATATCTTT GTATATATTA TTGTTTTTTC TCCTATCTTG TAATTTCTTT GAGCACATCC
5884 CAAAGAGGAA TGCCTAGATC AATGGGCACA ATAATTTGA CAGCTCTTAT TAAACATTAT
5944 TCTGTAAGTA AAAACTGAAC TACTTTTCAG TATCACTAGC AACATATGAG TGTATCAGCT
6004 TCCTAAACCC CTCCATGTTA GGTCATTATG AACTTATGAT CTAACAAATT ACAGGGTCTT
6064 ATCCCACTAA TGAAATTATA AGAGATTCAA CACTTATTCA GCCCGAAGG ATTCATTCAA
6124 CGTAGAAAAT TCTAAGAACA TTAACCAAGT ATTTACCTGC CTAGTGAGTG TGGAAGACAT
6184 TGTGAAGGAC ACAAAGATGT ATAGAATTCC ATTCCTGACT TCCAGGTATT TACACCATAG
6244 GTGGGGACCT AACTACACAC ACACACACAC ACACACACAC ACACACACAC ACCATGCACA
6304 CACAATCTAC ATCAACACTT GATTTTATAC AAATACAATG AATTTACTTT CTTTTTGGTT
6364 CTTCTCTTCA CCAGTGAAAT TTGACATGGG TGCTTATAAG TCATCAAAGG ATGATGCTAA
6424 AATTACCGTG ATTCTAAGAA TCTCAAAAAC TCAATTGTAT GTGACTGCCC AAGATGAAGA
6484 CCAACCAGTG CTGCTGAAGG TCAGTTGTCC TTTGTCTCCA ACTTACCTTC ATTTACATCT
6544 CATATGTTTG TAAATAAGCC CAATAGGCAG ACACCTCTAA CAAGGTGACA CTGTCCTCTT
6604 TCCTTCCTAC CACAGCCCCC ACCTACCCAC CCCACTCCCA TTGATTCCAG AGGCGTGCCT
6664 AGGCAGGATC TATGAGAkAA TATAACAGAG AGTAAGAGGA AAATTACCTT CTTTCTTTTT
6724 CCTTTCCCTG CCTGACCTTA TTCACCTCCC ATCCCAGAGC ATCCATTTAT TCCATTGATC
6784 TTTACTGACA TCTATTATCT GACCTACACA ATACTAGACA TTAGGACAAT GTGGCCTGCC
6844 TCCAAGAAAC TCAAATAAGC CAACTGAGAT CAGAGAGGAT TAATCACCTG CCAATGGGCA
6904 CAAAGCAACA AGCTGGGAGC CAAGTCCCAA ATGGGGCCT GCTGCTTCCA GTTCCCCTCT
6964 CTCTGCATTG ATGTCAGCAT TATCCTTCGT CCCAGTCCTG TCTCCACTAC CACTTTCCCC
7024 CTCAAACACA CACACACACA ACAGCCTTAG ATGTTTTCTC CACTGATAAG TAGGTGACTC
7084 AATTTGTAAG TATATAATCC AAGACCTTCT ATTCCCAAGT AGAATTTATG TGCCTGCCTG
7144 TGCTTTTCTA CCTGGATCAA GTGATGTCTA CAGAGTAGGG CAGTAGCTTC ATTCATGAAC
7204 TCATTCAACA AGCATTATTC ACTGAGAGCC TTGTATTTTT CAGGCATAGT GCCAACAGCA
7264 GTGTGGACAG TGGTGCATCA AAGCCTCTAG TCTCATAGAA CTTAGTCTTC TGGAGGATAT
7324 GGAAAACAGA CAACCCAAAC AACCAACAAA AGAGCAAGAT GCTGCAAAAA AAAAAAAAT
7384 GAATAGGGTG CTAAGATAGA GAAAGTGGG AGAGTGCTAT TTAGACAAAG TGGTAAAAAC
7444 AAAGCCCCTT GTGAGATGAG AGCTGCCGAC AGAGGGGGCG GGTCATGGTT GTGGGTTTTT
7504 GGGTAGGACA TTCAGAGGAG GGGGCGGGTC GTGGTTGTGG GTTTTGGGT AGGACATTCA
```

Fig. 3 (cont.)

```
7564 GAGGAGGGGG CGGGTCGTGG TTGTGGGTTT TTGGGTAGGA CATTCAGAGG AGGGGGCGGG
7624 TCGTGGTTGT GGGTTTTTGG GTAGGACATT CAGAGGAGGG GGCGGGTCGT GGTTGTGGGT
7684 TTTTGGGACA TTCAGAGGAG TCTGAATGCA CCCAGGCCTA CAACTTCAAG ATGGTAAAGG
7744 ACAGCTCCAA GGATCAGAAG AAGCATTCTT GGAACTGGGG CATTTTGAGA AGGAGGAAAA
7804 ATATGCAGAG ACTAGTGCTT GCAGAGCTTG CATTTGGATT TCATTTGAGG TACAATGAAA
7864 ACCCATTAAT GGGTTTCACA CAGTGCAATG GCCTGACCTC ACTTATATTT CCTAAAATAG
7924 AAAACAGATC AGAAGGAAGG CAATAGAGAA GCAGAAAGTC AATGAGGAG GTTTCACAGC
7984 AGTCATGGGG GTGGGGTAAG GAAAAGAAGT GGAAAGAAAC AGACAGAATT GGGTTATATT
8044 TTGGAGATAG AACCAACAGA AGGAAGAGGA GAAACAACAT TTACTGAGAA GGGAAAAAGT
8104 AGGAGAGGAA TAGGTTTGGG AAATAAATCC TGCTGACATT GGAAACCCCA GGAAGCCTC
8164 AAAAGTATAT TTACTTGCTT TAGATTTAAA AGAATAGGAA AGAAGCATCT CAACTTGGAA
8224 TTTGAAATCT ATTTTTCCAT AAAAGTATTG TTAAATTCTA CTCATACTCA CAAGAAAAGT
8284 ACATTCTAAA GAGTATATTG AAAGAGTTTA CTGATATACT TAGGAATTTT GTGTGTATGT
8344 GTGTGTGTGT ATGTGTGTGT GTGTGTTTAA CCTTCAATTG TTGACTTAAA TACTGAGATA
8404 AATGTCATCT AAATGCTAAA TTGATTTCCC AAAGGTATGA TTTGTTCACT TGGAGATCAA
8464 AATGTTTAGG GGGCTTAGAA TCACTGTAGT GCTCAGATTT GATGCAAAAT GTCTTAGGCC
8524 TATGTTGAAG GCAGGACAGA AACAATGTTT CCCTCCTACC TGCCTGGATA CAGTAAGATA
8584 CTAGTGTCAC TGACAATCTT CATAACTAAT TTAGATCTCT CTCCAATCAA CTAAGGAAAT
8644 CAACTCTTAT TAATAGACTG GGCCACACAT CTACTAGGCA TGTAATAAAT GCTTGCTGAA
8704 TGAACAAATG AATGAAGAGC CTATAGCATC ATGTTACAGC CATAGTCCTA AGTGGTGTT
8764 TCTCATGAAG GCCAAATGCT AAGGGATTGA GCTTCAGTCC TTTTTCTAAC ATCTTGTTCT
8824 CTAACAGAAT TCTCTTCTTT TCTTCATAGG AGATGCCTGA GATACCCAAA ACCATCACAG
8884 GTAGTGAGAC CAACCTCCTC TTCTTCTGGG AAACTCACGG CACTAAGAAC TATTTCACAT
8944 CAGTTGCCCA TCCAAACTTG TTTATTGCCA CAAAGCAAGA CTACTGGGTG TGCTTGGCAG
9004 GGGGGCCACC CTCTATCACT GACTTTCAGA TACTGGAAAA CCAGGCGTAG GTCTGGAGTC
9064 TCACTTGTCT CACTTGTGCA GTGTTGACAG TTCATATGTA CCATGTACAT GAAGAAGCTA
9124 AATCCTTTAC TGTTAGTCAT TTGCTGAGCA TGTACTGAGC CTTGTAATTC TAAATGAATG
9184 TTTACACTCT TTGTAAGAGT GGAACCAACA CTAACATATA ATGTTGTTAT TTAAAGAACA
9244 CCCTATATTT TGCATAGTAC CAATCATTTT AATTATTATT CTTCATAACA ATTTTAGGAG
9304 GACCAGAGCT ACTGACTATG GCTACCAAAA AGACTCTACC CATATTACAG ATGGGCAAAT
9364 TAAGGCATAA GAAAACTAAG AAATATGCAC AATAGCAGTT GAAACAAGAA GCCACAGACC
9424 TAGGATTTCA TGATTTCATT TCAACTGTTT GCCTTCTGCT TTTAAGTTGC TGATGAACTC
9484 TTAATCAAAT AGCATAAGTT TCTGGGACCT CAGTTTTATC ATTTTCAAAA TGGAGGGAAT
9544 AATACCTAAG CCTTCCTGCC GCAACAGTTT TTTATGCTAA TCAGGGAGGT CATTTTGGTA
9604 AAATACTTCT CGAAGCCGAG CCTCAAGATG AAGGCAAAGC ACGAAATGTT ATTTTTTAAT
9664 TATTATTTAT ATATGTATTT ATAAATATAT TTAAGATAAT TATAATATAC TATATTTATG
9724 GGAACCCCTT CATCCTCTGA GTGTGACCAG GCATCCTCCA CAATAGCAGA CAGTGTTTTC
9784 TGGGATAAGT AAGTTTGATT TCATTAATAC AGGGCATTTT GGTCCAAGTT GTGCTTATCC
9844 CATAGCCAGG AAACTCTGCA TTCTAGTACT TGGGAGACCT GTAATCATAT AATAAATGTA
9904 CATTAATTAC CTTGAGCCAG TAATTGGTCC GATCTTTGAC TCTTTTGCCA TTAAACTTAC
9964 CTGGGCATTC TTGTTTCATT CAATTCCACC TGCAATCAAG TCCTACAAGC TAAAATTAGA
10024 TGAACTCAAC TTTGACAACC ATGAGACCAC TGTTATCAAA ACTTTCTTTT CTGGAATGTA
10084 ATCAATGTTT CTTCTAGGTT CTAAAAATTG TGATCAGACC ATAATGTTAC ATTATTATCA
10144 ACAATAGTGA TTGATAGAGT GTTATCAGTC ATAACTAAAT AAAGCTTGCA ACAAAATTCT
10204 CTGACACATA GTTATTCATT GCCTTAATCA TTATTTTACT GCATGGTAAT TAGGGACAAA
10264 TGGTAAATGT TTACATAAAT AATTGTATTT AGTGTTACTT TATAAAATCA AACCAAGATT
10324 TTATATTTTT TTCTCCTCTT TGTTAGCTGC CAGTATGCAT AAATGGCATT AAGAATGATA
10384 ATATTTCCGG GTTCACTTAA AGCTCATATT ACACATACAC AAAACATGTG TTCCCATCTT
10444 TATACAAACT CACACATACA GAGCTACATT AAAAACAACT AATAGGCCAG GCACGGTGGC
10504 TCAGACCTGT AATCCCAGCA CTTTGGGAGG
```

Fig. 3 (cont.)

```
-1933 AGAAAGAAAG AGAGAGAGAA AGAAAAGAAA GAGGAAGGAA GGAAGGAAGG AAGAAAGACA
-1873 GGCTCTGAGG AAGGTGGCAG TTCCTACAAC GGGAGAACCA GTGGTTAATT TGCAAAGTGG
-1813 ATCCTGTGGA GGCANNCAGA GGAGTCCCCT AGGCCACCCA GACAGGGCTT TTAGCTATCT
-1753 GCAGGCCAGA CACCAAATTT CAGGAGGGCT CAGTGTTAGG AATGGATTAT GGCTTATCAA
-1693 ATTCACAGGA AACTAACATG TTGAACAGCT TTTAGATTTC CTGTGGAAAA TATAACTTAC
-1633 TAAAGATGGA GTTCTTGTGA CTGACTCCTG ATATCAAGAT ACTGGGAGCC AAATTAAAAA
-1573 TCAGAAGGCT GCTTGGAGAG CAAGTCCATG AAATGCTCTT TTTCCCACAG TAGAACCTAT
-1513 TTCCCTCGTG TCTCAAATAC TTGCACAGAG GCTCACTCCC TTGGATAATG CAGAGCGAGC
-1453 ACGATACCTG GCACATACTA ATTTGAATAA AATGCTGTCA AATTCCCATT CACCCATTCA
-1393 AGCAGCAAAC TCTATCTCAC CTGAATGTAC ATGCCAGGCA CTGTGCTAGA CTTGGCTCAA
-1333 AAAGATTTCA GTTTCCTGGA GGAACCAGGA GGGCAAGGTT TCAACTCAGT GCTATAAGAA
-1273 GTGTTACAGG CTGGACACGG TGGCTCACGC CTGTAATCCC AACATTTGGG AGGCCGAGGC
-1213 GGGCAGATCA CAAGGTCAGG AGATCGAGAC CATCCTGGCT AACATGGTGA AACCCTGTCT
-1153 CTACTAAAAA TACAAAAAAT TAGCCGGGCG TTGGCGGCAG GTGCCTGTAG TCCCAGCTGC
-1093 TGGGGAGGCT GAGGCAGGAG AATGGTGTGA ACCCGGGAGG CGGAACTTGC AGGGGGCCGA
-1033 GATCGTGCCA CTGCACTCCA GCCTGGGCGA CAGAGTGAGA CTCTGTCTCA AAAAAAAAAA
 -973 AAAAGTGTTA TGATGCAGAC CTGTCAAAGA GGCAAAGGAG GGTGTTCCTA CACTCCAGGC
 -913 ACTGTTCATA ACCTGGACTC TCATTCATTC TACAAATGGA GGGCTCCCCT GGGCAGATCC
 -853 CTGGAGCAGG CACTTTGCTG GTGTCTCGGT TAAAGAGAAA CTGATAACTC TTGGTATTAC
 -793 CAAGAGATAG AGTCTCAGAT GGATATTCTT ACAGAAACAA TATTCCCACT TTTCAGAGTT
 -733 CACCAAAAAA TCATTTTAGG CAGAGCTCAT CTGGCATTGA TCTGGTTCAT CCATGAGATT
 -673 GGCTAGGGTA ACAGCACCTG GTCTTGCAGG GTTGTGTGAG CTTATCTCCA GGGTTGCCCC
 -613 AACTCCGTCA GGAGCCTGAA CCCTGCATAC CGTATGTTCT CTGCCCCAGC CAAGAAAGGT
 -553 CAATTTTCTC CTCAGAGGCT CCTGCAATTG ACAGAGAGCT CCCGAGGCAG AGAACAGCAC
 -493 CCAAGGTAGA GACCCACACC CTCAATACAG ACAGGGAGGG CTATTGGCCC TTCATTGTAC
 -433 CCATTTATCC ATCTGTAAGT GGGAAGATTC CTAAACTTAA GTACAAAGAA GTGAATGAAG
 -373 AAAAGTATGT GCATGTATAA ATCTGTGTGT CTTCCACTTT GTCCCACATA TACTAAATTT
 -313 AAACATTCTT CTAACGTGGG AAAATCCAGT ATTTTAATGT GGACATCAAC TGCACAACGA
 -253 TTGTCAGGAA AACAATGCAT ATTTGCATGG TGATACATTT GCAAAATGTG TCATAGTTTG
 -193 CTACTCCTTG CCCTTCCATG AACCAGAGAA TTATCTCAGT TTATTAGTCC CCTCCCCTAA
 -133 GAAGCTTCCA CCAATACTCT TTTCCCCTTT CCTTTAACTT GATTGTGAAA TCAGGTATTC
  -73 AACAGAGAAA TTTCTCAGCC TCCTACTTCT GCTTTTGAAA GCTATAAAAA CAGCGAGGGA
  -13 GAAACTGGCA GATACCAAAC CTCTTCGAGG CACAAGGCAC AACAGGCTGC TCTGGGATTC
   48 TCTTCAGCCA ATCTTCATTG CTCAAGTATG ACTTTAATCT TCCTTACAAC TAGGTGCTAA
  108 GGGAGTCTCT CTGTCTCTCT GCCTCTTTGT GTGTATGCAT ATTCTCTCTC TCTCTCTCTT
  168 TCTTTCTCTG TCTCTCCTCT CCTTCCTCTC TGCCTCCTCT CTCAGCTTTT TGCAAAAATG
  228 CCAGGTGTAA TATAATGCTT ATGACTCGGG AAATATTCTG GAATGGATA CTGCTTATCT
  288 AACAGCTGAC ACCCTAAAGG TTAGTGTCAA AGCCTCTGCT CCAGCTCTCC TAGCCAATAC
  238 ATTGCTAGTT GGGGTTTGGT TTAGCAAATG CTTTTCTCTA GACCCAAAGG ACTTCTCTTT
  308 CACACATTCA TTCATTTACT CAGAGATCAT TTCTTTGCAT GACTGCCATG CACTGGATGC
  468 TGAGAGAAAT CACACATGAA CGTAGCCGTC ATGGGAAGT CACTCATTTT CTCCTTTTTA
  528 CACAGGTGTC TGAAGCAGCC ATGGCAGAAG TACCTGAGCT CGCCAGTGAA ATGATGGCTT
  588 ATTACAGGTC AGTGGAGACG CTGAGACCAG TAACATGAGC AGGTCTCCTC TTTCAAGAGT
  648 AGAGTGTTAT CTGTGCTTGG AGACCAGATT TTTCCCCTAA ATTGCCTCTT TCAGTGGCAA
  708 ACAGGGTGCC AAGTAAATCT GATTTAAAGA CTACTTTCCC ATTACAAGTC CCTCCAGCCT
  768 TGGGACCTGG AGGCTATCCA GATGTGTTGT TGCAAGGGCT TCCTGCAGAG GCAAATGGGG
  828 AGAAAAGATT CCAAGCCCAC AATACAAGGA ATCCCTTTGC AAAGTGTGGC TTGGAGGGAG
  888 AGGGAGAGCT CAGATTTTAG CTGACTCTGC TGGGCTAGAG GTTAGGCCTC AAGATCCAAC
  948 AGGGAGCACC AGGGTGCCCA CCTGCCAGGC CTAGAATCTG CCTTCTGGAC TGTTCTGCGC
```

Fig. 4

```
1008 ATATCACTGT GAAACTTGCC AGGTGTTTCA GGCAGCTTTG AGAGGCAGGC TGTTTGCAGT
1068 TTCTTATGAA CAGTCAAGTC TTGTACACAG GGAAGGAAAA ATAAACCTGT TTAGAAGACA
1128 TAATTGAGAC ATGTCCCTGT TTTTATTACA GTGGCAATGA GGATGACTTG TTCTTTGAAG
1188 CTGATGGCCC TAAACAGATG AAGGTAAGAC TATGGGTTTA ACTCCCAACC CAAGGAAGGG
1248 CTCTAACACA GGGAAAGCTC AAAGAAGGGA GTTCTGGGCC ACTTTGATGC CATGGTATTT
1308 TGTTTTAGAA AGACTTTAAC CTCTTCCAGT GAGACACAGG CTGCACCACT TGCTGACCTG
1368 GCCACTTGGT CATCATATCA CCACAGTCAC TCACTAACGT TGGTGGTGGT GGCCACACTT
1428 GGTGGTGACA GGGGAGGAGT AGTGATAATG TTCCCATTTC ATAGTAGGAA GACAACCAAG
1488 TCTTCAACAT AAATTTGATT ATCCTTTTAA GAGATGGATT CAGCCTATGC CAATCACTTG
1548 AGTTAAACTC TGAAACCAAG AGATGATCTT GAGAACTAAC ATATGTCTAC CCCTTTTGAG
1608 TAGAATAGTT TTTTGCTACC TGGGGTGAAG CTTATAACAA CAAGACATAG ATGATATAAA
1668 CAAAAAGATG AATTGAGACT TGAAAGAAAA CCATTCACTT GCTGTTTGAC CTTGACAAGT
1728 CATTTTACCC GCTTTGGACC TCATCTGAAA AATAAAGGGC TGAGCTGGAT GATCTCTGAG
1788 ATTCCAGCAT CCTGCAACCT CCAGTTCTGA AATATTTTCA GTTGTAGCTA AGGGCATTTG
1848 GGCAGCAAAT GGTCATTTTT CAGACTCATC CTTACAAAGA GCCATGTTAT ATTCCTGCTG
1908 TCCCTTCTGT TTTATATGAT GCTCAGTAGC CTTCCTAGGT GCCCAGCCAT CAGCCTAGCT
1968 AGGTCAGTTG TGCAGGTTGG AGGCAGCCAC TTTTCTCTGG CTTTATTTTA TTCCAGTTTG
2028 TGATAGCCTC CCCTAGCCTC ATAATCCAGT CCTCAATCTT GTTAAAAACA TATTTCTTTA
2088 GAAGTTTTAA GACTGGCATA ACTTCTTGGC TGCAGCTGTG GAGGAGCCC ATTGGCTTGT
2148 CTGCCTGGCC TTTGCCCCCC ATTGCCTCTT CCAGCAGCTT GGCTCTGCTC CAGGCAGGAA
2208 ATTCTCTCCT GCTCAACTTT CTTTTGTGCA CTTACAGGTC TCTTTAACTG TCTTTCAAGC
2268 CTTTGAACCA TTATCAGCCT TAAGGCAACC TCAGTGAAGC CTTAATACGG AGCTTCTCTG
2328 AATAAGAGGA AAGTGGTAAC ATTTCACAAA AAGTACTCTC ACAGGATTTG CAGAATGCCT
2388 ATGAGACAGT GTTATGAAAA AGGAAAAAAA AGAACAGTGT AGAAAAATTG AATACTTGCT
2448 GAGTGAGCAT AGGTGAATGG AAAATGTTAT GGTCATCTGC ATGAAAAAGC AAATCATAGT
2508 GTGACAGCAT TAGGGATACA AAAAGATATA GAGAAGGTAT ACATGTATGG TGTAGGTGGG
2568 GCATGTACAA AAAGATGACA AGTAGAATCG GGATTTATTC TAAAGAATAG CCTGTAAGGT
2628 GTCCAGAAGC CACATTCTAG TCTTGAGTCT GCCTCTACCT GCTGTGTGCC CTTGAGTACA
2688 CCCTTAACCT CCTTGAGCTT CAGAGAGGGA TAATCTTTTT ATTTTATTTT ATTTTATTTT
2748 GTTTTGTTTT GTTTTGTTTT GTTTTATGAG ACAGAGTCTC ACTCTGTTGC CCAGGCTGGA
2808 GTGCAGTGGT ACAATCTTGG CTTACTGCAT CCTCCACCTC CTGAGTTCAA GCGATTCTCC
2868 TTCCTCAGTC TCCTGAATAG CTAGGATTAC AGGTGCACCC CACCACACCC AGCTAATTTT
2928 TGTATTTTTA GTAGAGAAGG GGTTTCGCCA TGTTGGCCAG GCTGGTTTTG AAGTCCTGAC
2988 CTAAATGATT CATCCACCTC GGCTTCCCAA AGTGCTGGGA TTACAGGCAT GAGCCACCAC
3048 GCCTGGCCCA GAGAGGGATG ATCTTTAGAA GCTCGGGATT CTTTCAAGCC CTTTCCTCCT
3108 CTCTGAGCTT TCTACTCTCT GATGTCAAAG CATGGTTCCT GGCAGGACCA CCTCACCAGG
3168 CTCCCTCCCT CGCTCTCTCC GCAGTGCTCC TTCCAGGACC TGGACCTCTG CCCTCTGCAT
3228 GGCGGCATCC AGCTACGAAT CTCCGACCAC CACTACAGCA AGGGCTTCAG GCAGGCCGCG
3288 TCAGTTGTTG TGGCCATGGA CAAGCTGAGG AAGATGCTGG TTCCCTGCCC ACAGACCTTC
3348 CAGGAGAATG ACCTGAGCAC CTTCTTTCCC TTCATCTTTG AAGAAGGTAG TTAGCCAAGA
3408 GCAGGCAGTA GATCTCCACT TGTGTCCTCT TGGAAGTCAT CAAGCCCAG CCAACTCAAT
3468 TCCCCAGAG CCAAAGCCCT TTAAAGGTAG AAGGCCCAGC GGGGAGACAA AACAAAGAAG
3528 GCTGGAAACC AAAGCAATCA TCTCTTTAGT GGAAACTATT CTTAAAGAAG ATCTTGATGG
3588 CTACTGACAT TTGCAACTCC CTCACTCTTT CTCAGGGGCC TTTCACTTAC ATTGTCACCA
3648 GAGGTTCGTA ACCTCCCTGT GGGCTAGTGT TATGACCATC ACCATTTTAC CTAAGTAGCT
3708 CTGTTGCTCG GCCACAGTGA GCAGTAATAG ACCTGAAGCT GGAACCCATG TCTAATAGTG
3768 TCAGGTCCAG TGTTCTTAGC CACCCCACTC CCAGCTTCAT CCCTACTGGT GTTGTCATCA
3828 GACTTTGACC GTATATGCTC AGGTGTCCTC CAAGAAATCA AATTTTGCCA CCTCGCCTCA
3888 CGAGGCCTGC CCTTCTGATT TTATACCTAA ACAACATGTG CTCCACATTT CAGAACCTAT
3948 CTTCTTCGAC ACATGGGATA ACGAGGCTTA TGTGCACGAT GCACCTGTAC GATCACTGAA
```

Fig. 4 (cont.)

```
4008 CTGCACGCTC CGGGACTCAC AGCAAAAAAG CTTGGTGATG TCTGGTCCAT ATGAACTGAA
4068 AGCTCTCCAC CTCCAGGGAC AGGATATGGA GCAACAAGGT AAATGGAAAC ATCCTGGTTT
4128 CCCTGCCTGG CCTCCTGGCA GCTTGCTAAT TCTCCATGTT TTAAACAAAG TAGAAAGTTA
4188 ATTTAAGGCA AATGATCAAC ACAAGTGAAA AAAAATATTA AAAAGGAATA TACAAACTTT
4248 GGTCCTAGAA ATGGCACATT TGATTGCACT GGCCAGTGCA TTTGTTAACA GGAGTGTGAC
4308 CCTGAGAAAT TAGACGGCTC AAGCACTCCC AGGACCATGT CCACCCAAGT CTCTTGGGCA
4368 TAGTGCAGTG TCAATTCTTC CACAATATGG GGTCATTTGA TGGACATGGC CTAACTGCCT
4428 GTGGGTTCTC TCTTCCTGTT GTTGAGGCTG AAACAAGAGT GCTGGAGCGA TAATGTGTCC
4488 ATCCCCCTCC CCAGTCTTCC CCCCTTGCCC CAACATCCGT CCCACCCAAT GCCAGGTGGT
4548 TCCTTGTAGG GAAATTTTAC CGCCCAGCAG GAACTTATAT CTCTCCGCTG TAACGGGCAA
4608 AAGTTTCAAG TGCGGTGAAC CCATCATTAG CTGTGGTGAT CTGCCTGGCA TCGTGCCACA
4668 GTAGCCAAAG CCTCTGCACA GGAGTGTGGG CAACTAAGGC TGCTGACTTT GAAGGACAGC
4728 CTCACTCAGG GGGAAGCTAT TGCTCTCAG CCAGGCCAAG AAAATCCTGT TTCTTTGGAA
4788 TCGGGTAGTA AGAGTGATCC CAGGGCCTCC AATTGACACT GCTGTGACTG AGGAAGATCA
4848 AAATGAGTGT CTCTCTTTGG AGCCACTTTC CCAGCTCAGC CTCCTCTC CCAGTTTCTT
4908 CCCATGGGCT ACTCTCTGTT CCTGAAACAG TTCTGGTGCC TGATTTCTGG CAGAAGTACA
4968 GCTTCACCTC TTTCCTTTCC TTCCACATTG ATCAAGTTGT TCCGCTCCTG TGGATGGGCA
5028 CATTGCCAGC CAGTGACACA ATGGCTTCCT TCCTTCCTTC CTTCAGCATT TAAAATGTAG
5088 ACCCTCTTTC ATTCTCCGTT CCTACTGCTA TGAGGCTCTG AGAAACCCTC AGGCCTTTGA
5148 GGGGAAACCC TAAATCAACA AAATGACCCT GCTATTGTCT GTGAGAAGTC AAGTTATCCT
5208 GTGTCTTAGG CCAAGGAACC TCACTGTGGG TTCCCACAGA GGCTACCAAT TACATGTATC
5268 CTACTCTCGG GGCTAGGGGT TGGGGTGACC CTGCATGCTG TGTCCCTAAC CACAAGACCC
5328 CCTTCTTTCT TCAGTGGTGT TCTCCATGTC CTTTGTACAA GGAGAAGAAA GTAATGACAA
5388 AATACCTGTG GCCTTGGGCC TCAAGGAAAA GAATCTGTAC CTGTCCTGCG TGTTGAAAGA
5448 TGATAAGCCC ACTCTACAGC TGGAGGTAAG TGAATGCTAT GGAATGAAGC CCTTCTCAGC
5508 CTCCTGCTAC CACTTATTCC CAGACAATTC ACCTTCTCCC CGCCCCCATC CCTAGGAAAA
5568 GCTGGGAACA GGTCTATTTG ACAAGTTTTG CATTAATGTA AATAAATTTA ACATAATTTT
5628 TAACTGCGTG CAACCTTCAA TCCTGCTGCA GAAAATTAAA TCATTTTGCC GATGTTATTA
5688 TGTCCTACCA TAGTTACAAC CCCAACAGAT TATATATTGT TAGGGCTGCT CTCATTTGAT
5748 AGACACCTTG GGAAATAGAT GACTTAAAGG GTCCCATTAT CACGTCCACT CCACTCCCAA
5808 AATCACCACC ACTATCACCT CCAGCTTTCT CAGCAAAAGC TTCATTTCCA AGTTGATGTC
5868 ATTCTAGGAC CATAAGGAAA AATACAATAA AAAGCCCCTG GAAACTAGGT ACTTCAAGAA
5928 GCTCTAGCTT AATTTTCACC CCCCCAAAAA AAAAAAATTC TCACCTACAT TATGCTCCTC
5988 AGCATTTGGC ACTAAGTTTT AGAAAAGAAG AAGGGCTCTT TTAATAATCA CACAGAAAGT
6048 TGGGGGCCCA GTTACAACTC AGGAGTCTGG CTCCTGATCA TGTGACCTGC TCGTCAGTTT
6108 CCTTTCTGGC CAACCCAAAG AACATCTTTC CCATAGGCAT CTTTGTCCCT TGCCCCACAA
6168 AAATTCTTCT TTCTCTTTCG CTGCAGAGTG TAGATCCCAA AAATTACCCA AGAAGAAGA
6228 TGGAAAAGCG ATTTGTCTTC AACAAGATAG AAATCAATAA CAAGCTGGAA TTTGAGTCTG
6288 CCCAGTTCCC CAACTGGTAC ATCAGCACCT CTCAAGCAGA AAACATGCCC GTCTTCCTGG
6348 GAGGGACCAA AGGCGGCCAG GATATAACTG ACTTCACCAT GCAATTTGTG TCTTCCTAAA
6408 GAGAGCTGTA CCCAGAGAGT CCTGTGCTGA ATGTGGACTC AATCCCTAGG CTGGCAGAA
6468 AGGGAACAGA AAGGTTTTTG AGTACGGCTA TAGCCTGGAC TTTCCTGTTG TCTACACCAA
6528 TGCCCAACTG CCTGCCTTAG GGTAGTGCTA AGAGGATCTC CTGTCCATCA GCCAGGACAG
6588 TCAGCTCTCT CCTTTCAGGG CCAATCCCCA GCCCTTTTGT TGAGCCAGGC CTCTCTCACC
6648 TCTCCTACTC ACTTAAAGCC CGCCTGACAG AAACCACGGC CACATTTGGT TCTAAGAAAC
6708 CCTCTGTCAT TCGCTCCCAC ATTCTGATGA GCAACCGCTT CCCTATTTAT TTATTTATTT
6768 GTTTGTTTGT TTTGATTCAT TGGTCTAATT TATTCAAAGG GGGCAAGAAG TAGCAGTGTC
6828 TGTAAAAGAG CCTAGTTTTT AATAGCTATG GAATCAATTC AATTTGGACT GGTGTGCTCT
6888 CTTTAAATCA AGTCCTTTAA TTAAGACTGA AAATATATAA GCTCAGATTA TTTAAATGGG
6948 AATATTTATA AATGAGCAAA TATCATACTG TTCAATGGTT CTGAAATAAA CTTCACTGAA
```

Fig. 4 (cont.)

```
7008 GAAAAAAAAA AAAGGGTCTC TCCTGATCAT TGACTGTCTG GATTGACACT GACAGTAAGC
7068 AAACAGGCTG TGAGAGTTCT TGGGACTAAG CCCACTCCTC ATTGCTGAGT GCTGCAAGTA
7128 CCTAGAAATA TCCTTGGCCA CCGAAGACTA TCCTCCTCAC CCATCCCCTT TATTTCGTTG
7188 TTCAACAGAA GGATATTCAG TGCACATCTG GAACAGGATC AGCTGAAGCA CTGCAGGGAG
7248 TCAGGACTGG TAGTAACAGC TACCATGATT TATCTATCAA TGCACCAAAC ATCTGTTGAG
7308 CAAGCGCTAT GTACTAGGAG CTGGGAGTAC AGAGATGAGA ACAGTCACAA GTCCCTCCTC
7368 AGATAGGAGA GGCAGCTAGT TATAAGCAGA ACAAGGTAAC ATGACAAGTA GAGTAAGATA
7428 GAAGAACGAA GAGGAGTAGC CAGGAAGGAG GGAGGAGAAC GACATAAGAA TCAAGCCTAA
7488 AGGGATAAAC AGAAGATTTC CACACATGGG CTGGGCCAAT TGGGTGTCGG TTACGCCTGT
7548 AATCCCAGCA CTTTGGGTGG CAGGGGCAGA AAGATCGCTT GAGCCCAGGA GTTCAAGACC
7608 AGCCTGGGCA ACATAGTGAG ACTCCCATCT CTACAAAAAA TAAATAAATA AATAAAACAA
7668 TCAGCCAGGC ATGCTGGCAT GCACCTGTAG TCCTAGCTAC TTGGGAAGCT GACACTGGAG
7728 GATTGCTTGA GCCCAGAAGT TCAAGACTGC AGTGAGCTTA TCCGTTGACC TGCAGGTCGA
7788 C
```

Fig. 4 (cont.)

```
-5988 GTCGACCTGC AGGTCAACGG ATCTGAGAGG AGAGTAGCTT CTTGTAGATA ACAGTTGGAT
-5928 TATATACCAT GTCCTGATCC CCTTCATCAT CCAGGAGAGC AGAGGTGGTC ACCCTGATAG
-5868 CAGCAAGCCT GGGGGCTGCA GCTTGGTGGG TAGAGGTACT CAGGGGTACA GATGTCTCCA
-5808 AACCTGTCCT GCTGCCTTAG GGAGCTTCTA ATAAGTTGAT GGATTTGGTT AAAATTAACT
-5748 TGGCTACTTG GCAGGACTGG GTCAGTGAGG ACCAACAAAA AGAAGACATC AGATTATACC
-5688 CTGGGGGTTT GTATTTCTTG TGTTTCTTTC TCTTCTTTGT ACTAAAATAT TTACCCATGA
-5628 CTGGGAAAGA GCAACTGGAG TCTTTGTAGC ATTATCTTAG CAAAAATTTA CAAAGTTTGG
-5568 AAAACAATAT TGCCCATATT GTGTGGTGTG TCCTGTGACA CTCAGGATTC AAGTGTTGGC
-5508 CGAAGCCACT AAATGTGAGA TGAAGCCATT ACAAGGCAGT GTGCACATCT GTCCACCCAA
-5448 GCTGGATGCC AACATTTCAC AAATAGTGCT TGCGTGACAC AAATGCAGTT CCAGGAGGCC
-5388 CAAATGAAAA TGTTTGTACT GAAATTTGTT AAAGCTTCCC GACAAACTAG ATTTATCAGT
-5328 AAGGATTGTT TTCTGCAAGG GGGATGAAAC TTGTGGGGTG AGCCATTTGG GCTGAGGAGG
-5268 AGGGAGGTTG GAGCTGAGAA ATGTGGAGAC AATTTCCCTT TAGAAGGACT GAATCTCCCT
-5208 GCCTCTCTGG GGTGCGGCAG CCAGCAGGAT CCAATGGTGT ATATGTCTCC CCAGCTCCCC
-5148 ATTCAGTGAT ATCATGTCAG TAGCTTGAAA TTATCCGTGG TGGGAGTATT ATGTCATGGA
-5088 AATTGGCAAA TGGAAACTTT TATTGGAGAT TCAATTGTTA AACTTTTACC AGCACAACAC
-5028 TGCCCTGCCT TCAGAGTCAA TGACCCTATC CAAGTTTAAT CCATCTGTCC ACTGTCTCCA
-4968 ACACGATCTT TATAAAACAC ACCTGACAAC ATTACCCTTT TATTCAGTTT TTTAAAAGAT
-4908 AAGTTTCCAG CTCATCGGGG TGGCTTTAAA GGCCATTTCT CCTCTGGACC TCACCCAACT
-4848 TTTCAAATCA CTTTTCCTAC CCCTACCTCT AAATGCTACT CAAACTCCAG CCATCCTGAA
-4788 TAATAAGACT TTTGAAAAGT AGATTATGGG CTGGGCACAG TGGCTCACAC CTGTAATCCC
-4728 AGCACTTTGG GAGGCCAAGA TGGGTGGATC ACCTGAGGTC GGGAGTTCGA GACCAGCCTG
-4668 ACTAACATAG TGAAACCCTG TCTCTACTAA AATACAAAA TTAGTTGGGG GTGGTGGCAC
-4608 AAGCCTGTAA TCCCAGCTAC TCAGGAGGTT GAGGCAGGGG AATTGCTTGA ACCTGGGAGG
-4548 CGGAGGTTGC GGTGAGCCTA GATTGCTCCA CTGCACTCCA GCCTGGGCAA CAAGAGCGAA
-4488 ACTCCATCTC AAAAAAATAA ATAAATAAAT AAAGTAGATT ACATCAGATA CCTCTGGCCT
-4428 AGGTTGTTTA TGACCAACTC TCCTGCTGAG AATAACTAGA AAAGCTAGAC AAAACATATT
-4368 TCCAAAAGAT CTCTTTGGAG GCATCAGAGA ATGGCCAAGG CTGTAAGGAA CTGCCTGAGC
-4308 CCAGAGAGGT GGAGCCCAGC ACTGGTGCCC TTTACTCCTG GGGACATGTG CTGGTTTCAA
-4248 AAACTTCAGC TGAGCTTTTG AGCATTCATG GAACTTGGTG GGGGAGATGA AATTTGTACC
-4188 TTAAATCCTG CCTACAGGGA GGGTCCCTGA TAATCCCCAC CCAATTTGGA AATCTGGGTC
-4128 AGCCTTCACA GGTACTGAAG CCCTCCTCTG AATGATCTCA AGTCCTGCTA GGGTAGAGGT
-4068 TACCTGCTTT TGAAAGGCTC CTGGCCTACC TGTGCAGCAG GAGCAAAAGT GAACCATCTC
-4008 AGGGTACAGA TAACAATCAT CCAGAGCCTT GAATGACCTC TACTGTGCTT AATATATAGT
-3948 ATTCAGCAGT CAGTAAAAAG GATTTAGGCA CATGCAAGAT GACCTGTGTA TCAGGGAGAA
-3888 ATAGGCAATA AATTGAGATC CAGCAGGGAT TTGAATCATG GATTTGAATC AGGGGCAGCC
-3828 TTCGAAAGAA CTATGGAGAA TATACTCAGA TTTAAAACAT AAGATTGGAA TTTTTGGCAG
-3768 AGAACTAACA ACTGTACAAA AAAGGAACCA AATGGAAATC CTAGAACTGA AAGATGCAAT
-3708 TAACCGATGT TGAGAAATAG CCAACATCTA TTGAACACTT CCCATGTGGA CAGCTGTGCT
-3648 AAACACTTTA CAGGCATCAA CATAAGATGT GTCCCCTTAC AGCAGTGCAG TGTCCCTCCT
-3588 AAGACATGGA CAGCCTGGTT TCCCTATCTC TCTGCTTCAT CAAAACCCCT TTACGTGGGG
-3528 CTTAGACACT CCTGTTGTCT CTAGTGTCTA GTAGCACAGG GCTCAGCACA TGGAAGCCAC
-3468 TAGATACAAT TTGATGACCA GGACCTCCGA TGAAAGCCAT GGGTGCTGAT TGGGAAGGCA
-3408 TTGTCTTTTA TGTGCTATGG TCTTAAAGCT TCATCCAGGA AGCAGAACTC GGGGGGTGCT
-3348 GAGGACCCAG AACCGAGAAT AAGATTAGTC AGAGATTTCC TGTGGGCAGA AATCATAAGG
-3288 ACGCCAACTG TTTGGGTGAG ATAAGACGAA ACCAAGAGTG GACTTGTGGC CAGAAGCGTG
-3228 AGGAAGAGGG AGAGAGCTTC CCTTGTCCCC TTTCTTCCTC TCCCTAAGCC ACAGTGATTG
-3168 ACAGCCCCCC CGCTTTGGAG TCAGAGCAGG CTTGAGACTG GACTGGGAAA GGAGGGTGGG
-3108 TCAGGATACA GAGCAGGAAG GCTGGGAGTG CAGGGCAGGA GCAAGGGGCT GGGGCATTCA
-3048 TTGTGCCTGA TCTCTCCCAC TTTACCTGGG GTAAAGAAGC ATATGCAAAA GCCACGGTGT
```

Fig. 5

```
-2988 GAGTATTTCC CAAGTGCCAG GGTCAGGGCA TGATTCATCA CGTGCAGCAT TTCATTCAAT
-2928 CCTTATAGTA ACCGATGATG TGGCTTCTAT TATTAGCTCT ATCAGATAAT GAAACTGAGA
-2868 CCAAGACAGG CTCTGCACAT TGTGTGGGGT AATGACACAG GGGGATTCAG ACCTAGACTC
-2808 CATAACTCCT GCCCCAGGGA CCACCCCCAC CCTCACCCTG TGCATGTCGA CAAAGGACAG
-2748 ACTGGGCCAC TTCTCAGGAC ACAGCGGGGA AATGACACAG AGCAGGGAGG TTCCAGGAGC
-2688 CCCGAGCGTC TTTTCTCCAG GAGAATACTC TCTGAATTCA GACTGGGGTC AGAGAAACAT
-2628 TTACCCAGGA GCCGCAGTGT GGGTGGGGCT TTTTACTTGA AACGCTGTCT GAAGGCAGTG
-2568 GCAGGATGAA CTCTCCACCC TACCTTGGCA AGCCACTTCT CTTCTGCAAT CTGTAAGGAC
-2508 ATTGTTGAGA GAATTATGGT CTTCCAATTC CGGAGGGTTG AAGAAAGACA AATAGGAGAG
-2448 AACCTATCAT AGTCAGGTGC TAGCTGCCTT CTCTTTCAGA GAGTGTGAGA ATAAAGTGAT
-2388 ACACTTGATT ATTAGCAAAT ACTTTGGAAA TTTTAAACGC TAATATTCAA CACACTCTGG
-2328 AAGAGGCAAA TAAGTAGACA GGTTCATATA CATCATCTCC TTCAGCTAGT CCTCACAAAA
-2268 ACAAACAAAT GAATAAACAA AATTCTTCTT TGGCCCTCAT AGGAAGACAC TGTTTCTTGA
-2208 ACGTGTTTCA AAAGGATGG GTGACTCACT CAAGGTCACA CTGTTTATGA GGACAGTACA
-2148 GGAATACAGA CATGCCATTT TGCCTGAAAA AATCCATCAC CCAGGGAGGT GACACAATTT
-2088 TGCAGAAATG TTCTATTTCC TCTGAAGGAT ACATTCTTTA AACCTTGGG AAATTCATTC
-2028 ATAGTCTTCC TCCTTTGAAG GATTACTCTC TGGACACAAA GTGTTTGATT CTGATTTGTT
-1968 GGTTGGAAGA TGTGTTGGTT GAGAGAAAGA TTCTGATTTG TTGGTTGAAA ATAGACTCAT
-1908 CAAGATCAAC TGCTGTAGTA GTAAATATTT TGACATTTTG TCTGTATTCC TGTGCTGCCC
-1848 TCACAAGCTG CATCACCTTG AGTGAGTCAT TCATACTTTT TTGTTTGTTT TTGTTTTGGA
-1788 GATGGAGTCT TACTCTGTTG CCTAGGCTGG AGTGCGGTGG CGTGATCTTG GCTCACTGCG
-1728 ACCTCCATCT CCTGGGTTCA AGTGATCCTC CTGCCTCAGC CTCCCGAGTA GCTGGGATTA
-1668 CAGGCACATG CCACCATCCC TGCTAATTTT TGCATTTTCA GTAGAGACGG AGTTTCACCA
-1608 TGTTGGTCAG GTTGGTCTTG AACTCCTGAC CTCAGGTGAT CCGCCCACCT CAGCCTCCCC
-1548 AAGTGCTGGG ATTACAGGTG TGAGCCACCG TGCCCAGCCC AGCCATCATT TTTGAAACAC
-1488 GTTTGAGAAA TAGTGTCTTC CTTTGAGGGC CAAGGAGACA TTTTTTTTGT TTATTTGTTT
-1428 GTTTTTGTGA GGACTAGCTG AAGGGGGTGA TGTATATTAA CCTGCCTACT TATTTGCCTC
-1368 TTCCCAGAGT GTGATGAATA TTAGGGTTTA AAGTTTCTGA AGCATTTGTT AATAAAGCCC
-1308 GGGGCTGGAG GTCAGAAGAC CTGGATTTCT CTGCATACTT TTGCCATCAG CAAGCTGTGT
-1248 GACCTTGGAC AGATCCCTTT TTTGTCTAAA TCTTTCTGAG TCTTCTTGAA AACAATGCCA
-1188 GGTTGGGACA GGATGATTGC CAAGCTCCCG TCCAGCTCTA AAACACTGCA ACGTATGCTT
-1128 CTGCACCAGC ACTGTCCATC CTGTAGATCA TGCAGAAATT CTCTTCAACT TTTTCCTACC
-1068 CATAAAATAG GAGCATGCTT ACCTTTTTCC TAATGTTCCA GGCCCCGGGT CTAGATATTG
-1008 TAAGTAAGGA AGTTAATGTG TATCAGAGCC CATTATGGGC CAGAAGTTCT CCTCTTCCTT
 -948 CCTACACCTG CTTCCTCCCT CCCTCCCTCC CTCTTTCCCT TCCTTCCTTC CATCCATTTG
 -888 TGAAGAAGAC ATGATCACCC TCATTCTGAG AGTGAAGAGA CAGAGGCTCA ACTAATGAAA
 -828 TGATTTGTTC AAGGTCACAC GGGTGGCACA AGGCAAGTGG CAGAGGTTGA ATTTAGACCC
 -768 ATTCCTGTCC AAATGCTGAG TTTATGTCAT CGTCCCGAGA CCATAACTTT AAAGATGTAA
 -708 GATAGTGGGA AAAGAGTTGA TTTCAAAGCA CCTCTCAGAA GGACTCACTT TACATCAGGG
 -648 GTCAGCAGAC TCAGGCCAAA TCCGGTCCAT TCCCCGCTTT TGCAAAGAAA GTTGTAGTGG
 -588 AACACAGCTA GGCTTATTGA TTTATGGATT GCCAACGTCC TTTTGTGAAA CAGACAGCTG
 -528 AGCTGAGTAA TCGTGGCGCA CAAAACCTAA AATATTTACT ATCTCGTCCT TTACAGAATG
 -468 TTTGCCAATC TATGGTCCGG AGTCCAAGGC TGTCCATTTT TCAAAGAACA CAAAGTGACA
 -408 TGAGACTGTC CCATGTGCAG GGAGCCCTAT CATTTTATTA TGARAAAACG GCCTTTCTGC
 -348 TCAAATCTGT TTTTTAAAAA GTCAACAAAC AGACTCTGGG TACCTGTCAG GAACAGTAGG
 -288 GAGTTTGGTT TCCATTGTGC TCTTCTTCCC AGGAACTCAA TGAAGGGGAA ATAGAAATCT
 -228 TAATTTTGGG GAAATTGCAC AGGGGAAAAA GGGGAGGGAA TCAGTTACAA CACTCCATTG
 -168 CGACACTTAG TGGGGTTGAA AGTGACAACA GCAAGGGTTT CTCTTTTTGG AAATGCGAGG
 -108 AGGGTATTTC CGCTTCTCGC AGTGGGGCAG GGTGGCAGAC GCCTAGCTTG GGTGAGTGAC
  -48 TATTTCTTTA TAAACCACAA CTCTGGGCCC GCAATGGCAG TCCACTGCTT GCTGCAGTCA
```

Fig. 5 (cont.)

```
  13 CAGAATGGAA ATCTGCAGAG GCCTCCGCAG TCACCTAATC ACTCTCCTCC TCTTCCTGTT
  73 CCATTCAGAG ACGATCTGCC GACCCTCTGG GAGAAAATCC AGCAAGATGC AAGCCTTCAG
 133 GTAAGGCTAC CCCAAGGAGG AGAAGGTGAG GGTGGATCAG CTGGAGACTG GAAACATATC
 193 ACAGCTGCCA GGGCTGCCAG GCCAGAGGGC CTGAGAACTG GGTTTGGGCT GGAGAGGATG
 253 TCCATTATTC AAGAAAGAGG CTGTTACATG CATGGGCTTC AGGACTTGTG TTTCAAAATA
 313 TCCCAGATGT GGATAGTGCG ACCGGAGGGC TGTCTTACTT TCCCAGAGAC TCAGGAACCC
 373 AGTGAGTAAT AGATGCATGC CAAGGAGTGG GACTGCGATT CAGGCCTAGT TGAATGTGCT
 433 GACAGAGAAG CAGAGAGGGG CACCAGGGGC ACAGCCCGAA GGCCCAGACT GATATGGGCA
 493 AGGCCTGTCT GTGCTGACAT GTCGGAGGGT CCCACTCTCC AGGGACCTTG GTTTCCCCGT
 553 CTGTGACATC TGTGACATGA GAGTCACGAT AACTCCTTGT GTGCCTTACA GGGTTGTTGT
 613 GAAAATTAAA TGCACAGATA ATAGCGTAAC AGTATTCCGT GCATTGTAAA GAGCCTGAAA
 673 ACCATTATGA TTTGAAAATG GAATCGGCTT TGTGAGACCA TCACTATTGT AAAGATGTGA
 733 TGCTGATAGA AATGACAGGA CTGCTTGTGC ATGCCCTCTG CAGTGTGACA TTCCAGCAGT
 793 GAAATCATGT TGGGGTGACT CTCCCCCAC TCTGACCTTT ATGTTTGTCT GGGCCGAGGC
 853 TGCAAGTCGG GCTCTGTGGG TGTATGAGTG ACAAGTCTCT CCCTTCCAGA TATGGGGACT
 913 GTCTGCTTCC CTAGGTTGCC CTCCCTGCT CTGATCAGCT AGAAGCTCCA GGAGATCCTC
 973 CTGGAGGCCC CAGCAGGTGA TGTTTATCCC TCCAGACTGA GGCTAAATCT AGAAACTAGG
1033 ATAATCACAA ACAGGCAAT GCTGCCATAT GCAAAGCACT TTGGTTTGCC TGGCCACCCC
1093 TCGTCGAGCA TGTGGGCTCT TCAGAGCACC TGATGAGGTG GGTACAGTTA GCCACACTTC
1153 ACAGGTGAAG AGGTGAGGCA CAGGTCCCAG GTCAGGCTGG CCGGAGCTCT GTTTATTACG
1213 TCTCACAGCT TTGAGTCCTG CTCTCAACCA GAGAGGCCCT TTACCAAGAA GAAAGGATTG
1273 GGACCCAGAA TCAGGTCACT GGCTGAGGTA GAGAGGAAGC CGGGTTGTTC CCAAGGGTAG
1333 CTGCTCCTGC AGGACTCTGA GCAGGTCACC AGCTAATGGA GGAAAGGCTC TAGGGAAAGA
1393 CCCTTCTGGT CTCAGACTCA GAGCGAGTTA GCTGCAAGGT GTTCCGTCTC TTGAAACTTC
1453 TACCTAGGTG CTATGGTAGC CACTAGTCTC AGGTGGCTAT TTAAATTTAT ACTTAAATGA
1513 ATGAAAATAG AAGAAAATTT AAATCCAGA CCCTTGGTCA CACTATCCAC ATTTAAAGAG
1573 GTCAATAGCC ACATGTGGTT AGTGGCCACC CTATTGGGCA GTGCAGCTAC AGAACATTTT
1633 TGCATCCCAG AAAGTTCTTT TGGATGTTGC TGCTCTACAG CATGCTTTGC TGAAACAGAA
1693 GTGCCTTCCC TGGGAATCTC AGATGGGAAG CAAGTAAGGA GGGGAGTCAA ATGTGGGCTC
1753 ACTGCTCACC AGCTGTGAGG GTTGGGCCTG CCTCTTAACC ATTGTCAGCC TCAGTCTTCT
1813 CATCCATGCA TGCCGTGGGT ATACTAAAAT ACTATACCCC TGGAAGAGCT GGATGCAAAT
1873 TTGACAAGTT CTGGGGGACA CAGGAAGGTG CCAAGCACAA GGCTGGGCAC ATGGTGGCTG
1933 TGCACTACAG CTGAGTCCTT TTCCTTTTCA GAATCTGGGA TGTTAACCAG AAGACCTTCT
1993 ATCTGAGGAA CAACCAACTA GTTGCTGGAT ACTTGCAAGG ACCAAATGTC AATTTAGAAG
2053 GTGAGTGGTT GCCAGGAAAG CCAATGTATC TGGGCATCAC GTCACTTTGC CCGTCTGTCT
2113 GCAGCAGCAT GGCCTGCCTG CACAAACCCT AGGTGCAATG TCCTAATCCT TGTTGGGTCT
2173 TTGTATTCAA GTTTGAAGCT GGGAGGGCCT GGCTACTGAA GGGCACATAT GAGGGTAGCC
2233 TGAAGAGGGT GTGGAGAGGT AGAGTCTAGG TCAGAGGTCA GTGCCTATAG CAAGTGGTC
2293 CCAGGGCCAC AGCTGGGAAG GGCAAATACC AGAAGGCAAG GTTGACCATT CCCTTCCTCA
2353 AGTGCCTATT AAGGCTCCAT GTTCCTATGT TGTTCAAACC CTAACTCAAT CCCAAATTAA
2413 TCCACCATGT ATAAGGTTGA GCTATGTCTC TTATTCCTGG ACACCATACT CAGCCATATC
2473 TGGTCCACAC ATTAACAGCT GGATGACCTT GAAGAAGCTT CACCCACTCT GTTCCTCAGC
2533 TTTCCCTTCA GTGGGATGAT ATCAACTGGA CAACAGGATG TGCGATTCTT TTAGTTCCAG
2593 CCTTCCAGGA TGTTTTCACT CCCCTGTTTG TTGTTGTAGG ATGGTATTAC CTCCACCTTC
2653 CCACCTTCCC TATGCCCTGG TTCTGTCTCC TGTGCCTCGC TCTGAAAGTG GATGAGACCT
2713 ACAATTCCTG TCCTGGTAGT TCTCCTAATG AACACACTGA AGCACGAGGA AGCTGAGATT
2773 TTTGTTGCTA CATGAGAGCA TGGAGGCCTC TTAGGGAGAG AGGAGGTTCA GAGACTCCTA
2833 GGCTCCTGGT GGAGCCCCAC TCATGGCCTT GTTCATTTTC CCTGCCCCTC AGCAACACTC
2893 CTATTGACCT GGAGCACAGG TATCCTGGGG AAAGTGAGGG AAATATGGAC ATCACATGGA
```

Fig. 5(cont.)

```
2953 ACAACATCCA GGAGACTCAG GCCTCTAGGA GTAACTGGGT AGTGTGCATC CTGGGGAAAG
3013 TGAGGGAAAT ATGGACATCA CATGGAACAA CATCCAGGAG ACTCAGGCCT CTAGGAGTAA
3073 CTGGGTAGTG TGCATCCTGG GGAAAGTGAG GGAAATATGG ACATCACATG GAACAACATC
3133 CAGGAGACTC AGGCCTCTAG GAGTAACTGG GTAGTGTGCA TCCTGGGGAA AGTGAGGGAA
3193 ATATGGACAT CACATGGAAC AACATCCAGG AGACTCAGGC CTCTAGGAGT AACTGGGTAG
3253 TGTGCTTGGT TTAATCTTCT ATTTACCTGC AGACCAGGAA GATGAGACCT CTCTGCCCTT
3313 CTGACCTCGG GATTTTAGTT TTGTGGGGAC CAGGGGAGAT AGAAAAATAC CCGGGGTCTC
3373 TTCATTATTG CTGCTTCCTC TTCTATTAAC CTGACCCTCC CCTCTGTTCT TCCCCAGAAA
3433 AGATAGATGT GGTACCCATT GAGCCTCATG CTCTGTTCTT GGGAATCCAT GGAGGGAAGA
3493 TGTGCCTGTC CTGTGTCAAG TCTGGTGATG AGACCAGACT CCAGCTGGAG GTAAAAACAT
3553 GCTTTGGATC TCAAATCACC CCAAAACCCA GTGGCTTGAA ACAACCAAAA TTTTTTCTTA
3613 TGATTCTGTG GGTTGACCAG GATTAGCTGG GTAGTTCTGT TCCATGTGGT GGAACATGCT
3673 GGGGTCACTT TGGAAGCTGC ATTCAGCAGA GTGCCAGGCT TGCGCTGGGC ATCCAAGGTG
3733 GTCCCTCATC CTCCAGGCTC TCTTTCCATG TGATCTCTCA GTGTTTAAGA GTTAGTTGGA
3793 GCTTCCTTAC AGCATGGCGG CTGACTTCCA AAAGGGATTA TTCCAAAAAG AGCCTCAACA
3853 TGCAGGCGCT TATTATGACT TCTGCTTGCA TCATCCTATT GGCCAAAGCC AGTCACGTGG
3913 CTAAGTCTAG CCCCCTGTGA GAGGAGACTG CATAAGAGTG TGAACACCAG GAGACACGGT
3973 CACTGGGGGC CACCACTGTA ACCATCTACC ACAGGACCTG AATCTCTGTG TGCTACTCCC
4033 TTGCTCAAGG GCCCCCCTAC CCACGCAGAC CTGCTGTCTT CTAGCAAAGC CCATCCTCAG
4093 GACCTTTCTC TTCCAATCCT TATTGACTCA AATTGATTAG TTGGTGCTCC ACCCAGAGCC
4153 CTGTGCTCCT TTATCTCATG TAATGTTAAT GGGTTTCCCA GCCCTGGGAA AACATGGCTT
4213 TGTCTCAGGG GCTTGCTGGA TGCAACCTTA ACCTCAATGT GAGTGGCCAT ACTGTGGCAC
4273 TGTCCCATCC CTCACCAGGG ACACTGTTCT GGAGGGTGAC TGCCTGTTCT GTGAGGAGTG
4333 GGGATGGCTA GGACATTGCA TGGAACACAC CACCACCCCA TCTTCTCAGA GCTCAAACCC
4393 TGACAGAACA CCAGCTCCAC AGGCCTTGGC TTCTGCTGAT GGTGCCGTGT ATTTACCAGA
4453 CTTAGTGGTC CAAGGCCAGA GTGGCAGATT TCCCAAAGTC AAGGTGTGAC AGTGGGACAG
4513 CCTCTTTGTG TCTTTGCTGT CCTAAGAAAC CTGGGCCAGG CCAGGCGCAG TGGCTCACGC
4573 CTTGTAATCC CAGCACTTTG AGAGGCCAAG GTGGGCAGAT CACGAGGTCA GGAGTTTGAG
4633 ACCAGCCTGG CCAACATTGG TGAAACCCTG TCTCTATTAA AAATAGAAAA CATTAGACAG
4693 GTGTGGTGGT GCATGCCTGT AATCCCAGCT ACTCAGGAGG CTGAGGCAGG AGAATCGCTT
4753 GAACCCAGGA GGTGGAGGTT GCAGTGAGCC GAGATTGTGC CACTGCACTC CAGCCTAGGC
4813 GACAGAGCAA GACTCCGTCT CGGGAAAATT AATTAATAAA TAAATAAACC TAGGTCCCAG
4873 AGTCCCACAG AATGGCAGAC AGGAGCACCT GGGGGCTTTT AGGGTATGGC ATTTCCCCTG
4933 TACTAACTCT GGGCTGTCCA GAGGCGATTT CATGGCGTGG AGTGGAGAGG GAGGCAGCAC
4993 AGGACTTCCT AGGCCTCAGC TCTCACCTGC CCATCTTTTG ATTTCCAGGC AGTTAACATC
5053 ACTGACCTGA GCGAGAACAG AAAGCAGGAC AAGCGCTTCG CCTTCATCCG CTCAGACAGT
5113 GGCCCCACCA CCAGTTTTGA GTCTGCCGCC TGCCCCGGTT GGTTCCTCTG CACAGCGATG
5173 GAAGCTGACC AGCCCGTCAG CCTCACCAAT ATGCCTGACG AAGGCGTCAT GGTCACCAAA
5233 TTCTACTTCC AGGAGGACGA GTAGTACTGC CCAGGCCTGC CTGTTCCCAT TCTTGCATGG
5293 CAAGGACTGC AGGGACTGCC AGTCCCCCTG CCCCAGGGCT CCCGGCTATG GGGCACTGA
5353 GGACCAGCCA TTGAGGGGTG GACCCTCAGA AGGCGTCACA ACAACCTGGT CACAGGACTC
5413 TGCCTCCTCT TCAACTGACC AGCCTCCATG CTGCCTCCAG AATGGTCTTT CTAATGTGTG
5473 AATCAGAGCA CAGCAGCCCC TGCACAAAGC CCTTCCATGT CGCCTCTGCA TTCAGGATCA
5533 AACCCCGACC ACCTGCCCAA CCTGCTCTCC TCTTGCCACT GCCTCTTCCT CCCTCATTCC
5593 ACCTTCCCAT GCCCTGGATC CATCAGGCCA CTTGATGACC CCCAACCAAG TGGCTCCCAC
5653 ACCCTGTTTT ACAAAAAAGA AAAGACCAGT CCATGAGGGA GGTTTTAAG GGTTTGTGGA
5713 AAATGAAAAT TAGGATTTCA TGATTTTTTT TTTTCAGTCC CCGTGAAGGA GAGCCCTTCA
5773 TTTGGAGATT ATGTTCTTTC GGGGAGAGGC TGAGGACTTA AAATATTCCT GCATTTGTGA
5833 AATGATGGTG AAAGTAAGTG GTAGCTTTTC CCTTCTTTTT CTTCTTTTTT TGTGATGTCC
5893 CAACTTGTAA AAATTAAAAG TTATGGTACT ATGTTAGCCC CATAATTTTT TTTTTCCTTT
```

Fig. 5 (cont.)

```
5953 TAAAACACTT CCATAATCTG GACTCCTCTG TCCAGGCACT GCTGCCCAGC CTCCAAGCTC
6013 CATCTCCACT CCAGATTTTT TACAGCTGCC TGCAGTACTT TACCTCCTAT CAGAAGTTTC
6073 TCAGCTCCCA AGGCTCTGAG CAAATGTGGC TCCTGGGGGT TCTTTCTTCC TCTGCTGAAG
6133 GAATAAATTG CTCCTTGACA TTGTAGAGCT TCTGGCACTT GGAGACTTGT ATGAAAGATG
6193 GCTGTGCCTC TGCCTGTCTC CCCACCAGGC TGGGAGCTCT GCAGAGCAGG AAACATGACT
6253 CGTATATGTC TCAGGTCCCT GCAGGGCCAA GCACCTAGCC TCGCTCTTGG CAGGTACTCA
6313 GCGAATGAAT GCTGTATATG TTGGGTGCAA AGTTCCCTAC TTCCTGTGAC TTCAGCTCTG
6373 TTTTACAATA AAATCTTGAA AATGCCTATA TTGTTGACTA TGTCCTTGGC CTTGACAGGC
6433 TTTGGGTATA GAGTGCTGAG GAAACTGAAA GACCAATGTG TYTTYCTTAC CCCAGAGGCT
6493 GGCGCCTGGC CTCTTCTCTG AGAGTTCTTT TCTTCCTTCA GCCTCACTCT CCCTGGATAA
6553 CATGAGAGCA AATCTCTCTG CGGGG
```

Fig. 5(cont.)

SEQUENCE LISTING

```
<160> NUMBER OF SEQ ID NOS: 32

<210> SEQ ID NO 1
<211> LENGTH: 11970
<212> TYPE: DNA
<213> ORGANISM: Homo sapiens

<400> SEQUENCE: 1
aagcttctac cctagtctgg tgctacactt acattgctta catccaagtg tggttatttc    60
tgtggctcct gttataacta ttatagcacc aggtctatga ccaggagaat tagactggca   120
ttaaatcaga ataagagatt ttgcacctgc aatagacctt atgacaccta accaacccca   180
ttatttacaa ttaaacagga acagagggaa tactttatcc aactcacaca agctgttttc   240
ctcccagatc catgcttttt tgcgtttatt attttttaga gatgggggct tcactatgtt   300
gcccacactg gactaaaact ctgggcctca agtgattgtc ctgcctcagc ctcctgaata   360
gctgggacta caggggcatg ccatcacacc tagttcattt cctctattta aaatatacat   420
ggcttaaact ccaactggga acccaaaaca ttcatttgct aagagtctgg tgttctacca   480
cctgaactag gctggccaca ggaattataa aagctgagaa attctttaat aatagtaacc   540
aggcaacatc attgaaggct catatgtaaa aatccatgcc ttcctttctc ccaatctcca   600
ttcccaaact tagccactgg ttctggctga ggccttacgc atacctcccg gggcttgcac   660
```

```
acaccttctt ctacagaaga cacaccttgg gcatatccta cagaagacca ggcttctctc      720
tggtccttgg tagagggcta ctttactgta acagggccag ggtggagagt tctctcctga      780
agctccatcc cctctatagg aaatgtgttg acaatattca gaagagtaag aggatcaaga      840
cttctttgtg ctcaaatacc actgttctct tctctaccct gccctaacca ggagcttgtc      900
accccaaact ctgaggtgat ttatgcctta atcaagcaaa cttccctctt cagaaaagat      960
ggctcatttt ccctcaaaag ttgccaggag ctgccaagta ttctgccaat tcaccctgga     1020
gcacaatcaa caaattcagc cagaacacaa ctacagctac tattagaact attattatta     1080
ataaattcct ctccaaatct agccccttga cttcggattt cacgatttct cccttcctcc     1140
tagaaacttg ataagtttcc cgcgcttccc tttttctaag actacatgtt tgtcatctta     1200
taaagcaaag gggtgaataa atgaaccaaa tcaataactt ctggaatatc tgcaaacaac     1260
aataatatca gctatgccat ctttcactat tttagccagt atcgagttga atgaacatag     1320
aaaaatacaa aactgaattc ttccctgtaa attccccgtt ttgacgacgc acttgtagcc     1380
acgtagccac gcctacttaa gacaattaca aaggcgaaga aagactgact caggcttaag     1440
ctgccagcca gagagggagt catttcattg gcgtttgagt cagcaaaggt attgtcctca     1500
catctctggc tattaaagta tttctgttg ttgtttttct ctttggctgt tttctctcac      1560
attgccttct ctaaagctac agtctctcct ttcttttctt gtccctccct ggtttggtat     1620
gtgacctaga attacagtca gatttcagaa atgattctc tcattttgct gataaggact      1680
gattcgtttt actgagggac ggcagaacta gtttcctatg agggcatggg tgaatacaac     1740
tgaggcttct catgggaggg aatctctact atccaaaatt attaggagaa aattgaaaat     1800
ttccaactct gtctctctct tacctctgtg taaggcaaat accttattct tgtggtgttt     1860
ttgtaacctc ttcaaacttt cattgattga atgcctgttc tggcaataca ttaggttggg     1920
cacataagga ataccaacat aaataaaaca ttctaaaaga agtttacgat ctaataaagg     1980
agacaggtac atagcaaact aattcaaagg agctagaaga tggagaaaat gctgaatgtg     2040
gactaagtca ttcaacaaag ttttcaggaa gcacaaagag gaggggctcc cctcacagat     2100
atctggatta gaggctggct gagctgatgg tggctggtgt tctctgttgc agaagtcaag     2160
atggccaaag ttccagacat gttttgaagac ctgaagaact gttacaggta aggaataaga    2220
tttatctctt gtgatttaat gagggtttca aggctcacca gaatccagct aggcataaca     2280
gtggccagca tgggggcagg ccggcagagg ttgtagagat gtgtactagt cctgaagtca     2340
gagcaggttc agagaagacc cagaaaaact aagcattcag catgttaaac tgagattaca     2400
ttggcaggga gaccgccatt ttagaaaaat tattttttgag gtctgctgag ccctacatga    2460
atatcagcat caacttagac acagcctctg ttgagatcac atgccctgat ataagaatgg     2520
gttttactgg tccattctca ggaaaacttg atctcattca ggaacaggaa atggctccac     2580
agcaagctgg gcatgtgaac tcacatatgc aggcaaatct cactcagatg tagaagaaag     2640
gtaaatgaac acaaagataa aattacggaa catattaaac taacatgatg tttccattat     2700
ctgtagtaaa tactaacaca aactaggctg tcaaaatttt gcctggatat tttactaagt     2760
ataaattatg aaatctgttt tagtgaatac atgaaagtaa tgtgtaacat ataatctatt     2820
tggttaaaat aaaaaggaag tgcttcaaaa ccttctttt ctctaaagga gcttaacatt      2880
cttccctgaa cttcaattaa agctcttcaa tttgttagcc aagtccaatt tttacagata     2940
aagcacaggt aaagctcaaa gcctgtcttg atgactacta attccagatt agtaagatat     3000
```

-continued

```
gaattactct acctatgtgt atgtgtagaa gtccttaaat ttcaaagatg acagtaatgg    3060
ccatgtgtat gtgtgtgacc cacaactatc atggtcatta agtacattg gccagagacc     3120 acatgaaata acaacaatta cattctcatc atcttatttt gacagtgaaa atgaagaaga    3180
cagttcctcc attgatcatc tgtctctgaa tcaggtaagc aaatgactgt aattctcatg    3240
ggactgctat tcttacacag tggtttcttc atccaaagag aacagcaatg acttgaatct    3300
taaatacttt tgttttaccc tcactagaga tccagagacc tgtctttcat tataagtgag    3360
accagctgcc tctctaaact aatagttgat gtgcattggc ttctcccaga acagagcaga    3420
actatcccaa atccctgaga actggagtct cctggggcag gcttcatcag gatgttagtt    3480
atgccatcct gagaaagccc cgcaggccgc ttcaccaggt gtctgtctcc taacgtgatg    3540
tgttgtggtt gtcttctctg acaccagcat cagaggttag agaaagtctc caaacatgaa    3600
gctgagagag aggaagcaag ccagctgaaa gtgagaagtc tacagccact catcaatctg    3660
tgttattgtg tttggagacc acaaatagac actataagta ctgcctagta tgtcttcagt    3720
actggcttta aaagctgtcc ccaaaggagt atttctaaaa tattttgagc attgttaagc    3780
agatttttaa cctcctgaga gggaactaat tggaaagcta ccactcacta caatcattgt    3840
taacctattt agttacaaca tctcattttt gagcatgcaa ataaatgaaa aagtcttcct    3900
aaaaaaatca tctttttatc ctggaaggag aaggaaggt gagacaaaag ggagagaggg     3960
agggaagcct aatgaaacac cagttaccta agaccagaat ggagatcctc ctcactacct    4020
ctgttgaata cagcacctac tgaaagaact ttcattccct gaccatgaac agcctctcag    4080
cttctgtttt ccttcctcac agaaatcctt ctatcatgta agctatgcc cactccatga     4140 aggctgcatg gatcaatctg tgtctctgag tatctctgaa acctctaaaa catccaagct    4200
taccttcaag gagagcatgg tggtagtagc aaccaacggg aaggttctga agaagagacg    4260
gttgagttta agccaatcca tcactgatga tgacctggag gccatcgcca atgactcaga    4320
ggaaggtaag gggtcaagca caataatatc tttcttttac agttttaagc aagtagggac    4380
agtagaattt aggggaaaat taaacgtgga gtcagaataa caagaagaca accaagcatt    4440
agtctggtaa ctatacagag gaaaattaat ttttatcctt ctccaggagg gagaaatgag    4500 cagtggcct aatcgagaat acttgctcac agcattatt tcttagccat attgtaaagg      4560
tcgtgtgact tttagccttt caggagaaag cagtaataag accacttacg agctatgttc    4620
ctctcatact aactatgcct ccttggtcat gttacataat cttttcgtga ttcagtttcc    4680
tctactgtaa aatggagata atcagaatcc cccactcatt ggattgttgt aaagattaag    4740
agtctcaggc tttacagact gagctagctg ggccctcctg actgttataa agattaaatg    4800
agtcaacatc ccctaacttc tggactagaa taatgtctgg tacaaagtaa gcacccaata    4860
aatgttagct attactatca ttattattat tattttattt ttttttttg agatggagtc     4920 tggctctgtc acccaggctg gagtgcagtg gcacaatctc ggctcactgc aagctctgcc    4980
tcctgggttc atgccattct cctgcctcag cctcccgagt aagctgggaa tacaggcacc    5040
cgccactgtt cccggctaat ttttttgtatt tttagtagag acggagtttc accgtggtct   5100
ccatctcctc gtgatccacc caccttggcc tcccaaagtg ccgggattac aggcgtgagc    5160
caccgcgccc ggcctattat tattattatt actactacta ctacctatat gaatactacc    5220
agcaatacta attttattaat gactggatta tgtctaaacc tcacaagaat cctaccttct    5280
cattttacat aaaaggaaac taagctcatt gagataggta aactgcccaa tggcatacat    5340
ctgtaagtgg gagagcctca aatctaattc agttctacct gagtaaaaaa atcatggttt    5400
```

```
ctcctccatc cctttactgt acaagcctcc acatgaacta taaacccaat attcctgttt    5460
ttaagataat acctaagcaa taacgcatgt tcacctagaa ggttttaaaa tgtaacaaaa    5520
tataagaaaa taaaaatcac tcatatcgtc agtgagagtt tactactgcc agcactatgg    5580
tatgtttcct taaaatcttt gctatacaca tacctacatg tgaacaaata tgtctaacat    5640
caagaccaca ctatttacaa ctttatatcc agcttttctt acttagcaat gtattgagga    5700
cattttagag tgcccgtttt tcaccattat aagcaatgca acaatgaaca tctgtataaa    5760
taaatattca tttctctcac cctttatttc cttagaatat attcctagaa gtagaatttc    5820
ccagagccat gaggatttgt gacgctattg atatgtgcca ctttgcactc tctgtgacat    5880 ataataattat ttttaatgca ttcattttt tctcagagtg cattcgtttg aaaacataga    5940
cgggaaatac tggtagtctt ccttgtcagt tagaaacacc caaacaatga aaaatgaaaa    6000
agttgcacaa atagtctcta aaacaatga aactattgcc tgaggaattg aagtttaaaa    6060
agaagcacat aagcaacaac aaggataatc ctagaaaacc agttctgctg actgggtgat    6120
ttcacttctc tttgcttcct catctggatt ggaatattcc taatacccccc tccagaacta    6180 ttttccctgt ttgtactaga ctgtgtatat catctgtgtt tgtacataga cattaatctg    6240
cacttgtgat catggtttta gaaatcatca agcctaggtc atcaccttt agcttcctga    6300 gcaatgtgaa atacaacttt atgaggatca tcaaatacga attcatcctg aatgacgccc    6360
tcaatcaaag tataattcga gccaatgatc agtacctcac ggctgctgca ttacataatc    6420
tggatgaagc aggtacatta aaatggcacc agacatttct gtcatcctcc cctcctttca    6480
tttacttatt tatttatttc aatctttctg cttgcaaaaa acatacctct tcagagttct    6540
gggttgcaca attcttccag aatagcttga agcacagcac ccccataaaa atcccaagcc    6600
agggcagaag gttcaactaa atctggaagt tccacaagag agaagtttcc tatctttgag    6660
agtaaagggt tgtgcacaaa gctagctgat gtactacctc tttggttctt tcagacattc    6720
ttaccctcaa ttttaaaact gaggaaactg tcagacatat taaatgattt actcagattt    6780
acccagaagc caatgaagaa caatcactct cctttaaaaa gtctgttgat caaactcaca    6840
agtaacacca aaccaggaag atctttatta tctctgataa catatttgtg aggcaaaacc    6900
tccaataagc tacaaatatg gcttaaagga tgaagtttag tgtccaaaaa cttttatcac    6960
acacatccaa ttttcatggc ggacatgttt tagtttcaac agtatacata ttttcaaagg    7020
tccagagagg caattttgca ataaacaagc aagactttt ctgattggat gcacttcagc    7080
taacatgctt tcaactctac atttacaaat tattttgtgt tctatttttc tacttaatat    7140
tatttctgca attttcccaa tattgacatc gtgtatgtat ttgccatttt taatatcact    7200
agacaattca atcaggttgc tacgttggtc ccttgggttt actctaaata gcttgattgc    7260
aaatatcttt gtatatatta ttgttttttc tcctatcttg taatttcttt gagcacatcc    7320
caaagaggaa tgcctagatc aatgggcaca ataatttga cagctcttat taaacattat    7380
tctgtaagta aaaactgaac tacttttcag tatcactagc aacatatgag tgtatcagct    7440
tcctaaaccc ctccatgtta ggtcattatg aacttatgat ctaacaaatt acagggtctt    7500
atcccactaa tgaaattata agagattcaa cacttattca gccccgaagg attcattcaa    7560
cgtagaaaat tctaagaaca ttaaccaagt atttacctgc ctagtgagtg tggaagacat    7620
tgtgaaggac acaaagatgt atagaattcc attcctgact tccaggtatt tacaccatag    7680
gtggggacct aactacacac acacacacac acacacacac acacacacac accatgcaca    7740
```

-continued

```
cacaatctac atcaacactt gattttatac aaatacaatg aatttacttt cttttttggtt    7800
cttctcttca ccagtgaaat tgacatggg tgcttataag tcatcaaagg atgatgctaa     7860
aattaccgtg attctaagaa tctcaaaaac tcaattgtat gtgactgccc aagatgaaga    7920
ccaaccagtg ctgctgaagg tcagttgtcc tttgtctcca acttaccttc atttacatct    7980
catatgtttg taaataagcc caataggcag acacctctaa caaggtgaca ctgtcctctt    8040
tccttcctac cacagccccc acctacccac cccactccca ttgattccag aggcgtgcct    8100
aggcaggatc tatgagaaaa tataacagag agtaagagga aaattacctt ctttcttttt    8160
cctttccctg cctgacctta ttcacctccc atcccagagc atccatttat tccattgatc    8220
tttactgaca tctattatct gacctacaca atactagaca ttaggacaat gtggcctgcc    8280
tccaagaaac tcaaataagc caactgagat cagagaggat taatcacctg ccaatgggca    8340
caaagcaaca agctgggagc caagtcccaa aatgggcct gctgcttcca gttccctct     8400
ctctgcattg atgtcagcat tatccttcgt cccagtcctg tctccactac cactttcccc    8460
ctcaaacaca cacacacaca acagccttag atgttttctc cactgataag taggtgactc    8520
aatttgtaag tatataatcc aagaccttct attcccaagt agaatttatg tgcctgcctg    8580
tgcttttcta cctggatcaa gtgatgtcta cagagtaggg cagtagcttc attcatgaac    8640
tcattcaaca agcattattc actgagagcc ttgtatttt caggcatagt gccaacagca    8700
gtgtggacag tggtgcatca aagcctctag tctcatagaa cttagtcttc tggaggatat    8760
ggaaaacaga caacccaaac aaccaacaaa agagcaagat gctgcaaaaa aaaaaaaat    8820
gaataggtg ctaagataga aaaagtgggg agagtgctat ttagacaaag tggtaaaaac    8880
aaagccctt gtgagatgag agctgccgac agaggggcg ggtcatggtt gtgggttttt    8940
gggtaggaca ttcagaggag ggggcgggtc gtggttgtgg gttttttggg aggacattca    9000
gaggagggg cgggtcgtgg ttgtgggttt ttgggtagga cattcagagg aggggcgggg    9060
tcgtggttgt gggtttttgg gtaggacatt cagaggaggg ggcgggtcgt ggttgtgggt    9120
ttttgggaca ttcagaggag tctgaatgca cccaggccta caacttcaag atggtaaagg    9180
acagctccaa ggatcagaag aagcattctt ggaactgggg cattttgaga aggaggaaaa    9240
atatgcagag actagtgctt gcagagcttg catttggatt tcatttgagg tacaatgaaa    9300
acccattaat gggtttcaca cagtgcaatg gcctgacctc acttatattt cctaaaatag    9360
aaaacagatc agaaggaagg caatagagaa gcagaaagtc caatgaggag gtttcacagc    9420
agtcatgggg gtggggtaag gaaagaagt ggaaagaaac agacagaatt gggttatatt    9480
ttggagatag aaccaacaga aggaagagga gaaacaacat ttactgagaa gggaaaaagt    9540
aggagaggaa taggtttggg aaataaatcc tgctgacatt ggaaaccca aggaagcctc    9600
aaaagtatat ttacttgctt tagatttaaa agaataggaa agaagcatct caacttggaa    9660
tttgaaatct atttttccat aaaagtattg ttaaattcta ctcatactca caagaaaagt    9720
acattctaaa gagtatattg aaagagttta ctgatatact taggaattt gtgtgtatgt    9780
gtgtgtgtgt atgtgtgtgt gtgtgtttaa ccttcaattg ttgacttaaa tactgagata    9840
aatgtcatct aaatgctaaa ttgatttccc aaagtatga tttgttcact tggagatcaa    9900
aatgtttagg gggcttagaa tcactgtagt gctcagattt gatgcaaaat gtcttaggcc    9960
tatgttgaag gcaggacaga aacaatgttt ccctcctacc tgcctggata cagtaagata    10020
ctagtgtcac tgacaatctt cataactaat ttagatctct ctccaatcaa ctaaggaaat    10080
caactcttat taatagactg ggccacacat ctactaggca tgtaataaat gcttgctgaa    10140
```

-continued

```
tgaacaaatg aatgaagagc ctatagcatc atgttacagc catagtccta aagtggtgtt   10200
tctcatgaag gccaaatgct aagggattga gcttcagtcc tttttctaac atcttgttct   10260
ctaacagaat tctcttcttt tcttcatagg agatgcctga gatacccaaa accatcacag   10320
gtagtgagac caacctcctc ttcttctggg aaactcacgg cactaagaac tatttcacat   10380
cagttgccca tccaaacttg tttattgcca caaagcaaga ctactgggtg tgcttggcag   10440
gggggccacc ctctatcact gactttcaga tactggaaaa ccaggcgtag gtctggagtc   10500
tcacttgtct cacttgtgca gtgttgacag ttcatatgta ccatgtacat gaagaagcta   10560
aatcctttac tgttagtcat ttgctgagca tgtactgagc cttgtaattc taaatgaatg   10620
tttacactct ttgtaagagt ggaaccaaca ctaacatata atgttgttat ttaaagaaca   10680
ccctatattt tgcatagtac caatcatttt aattattatt cttcataaca attttaggag   10740
gaccagagct actgactatg gctaccaaaa agactctacc catattacag atgggcaaat   10800
taaggcataa gaaaactaag aaatatgcac aatagcagtt gaaacaagaa gccacagacc   10860
taggatttca tgatttcatt tcaactgttt gccttctgct tttaagttgc tgatgaactc   10920
ttaatcaaat agcataagtt tctgggacct cagtttatc attttcaaaa tggagggaat   10980
aatacctaag cctcctgcc gcaacagttt tttatgctaa tcagggaggt cattttggta   11040
aaatacttct cgaagccgag cctcaagatg aaggcaaagc acgaaatgtt atttttaat   11100 tattatttat atatgtattt ataaatatat ttaagataat tataatatac tatatttatg   11160
ggaacccctt catcctctga gtgtgaccag gcatcctcca caatagcaga cagtgtttc   11220 tgggataagt aagtttgatt tcattaatac agggcatttt ggtccaagtt gtgcttatcc   11280
catagccagg aaactctgca ttctagtact tgggagacct gtaatcatat aataaatgta   11340
cattaattac cttgagccag taattggtcc gatctttgac tcttttgcca ttaaacttac   11400
ctgggcattc ttgtttcatt caattccacc tgcaatcaag tcctacaagc taaaattaga   11460
tgaactcaac tttgacaacc atgagaccac tgttatcaaa actttctttt ctggaatgta   11520
atcaatgttt cttctaggtt ctaaaaattg tgatcagacc ataatgttac attattatca   11580
acaatagtga ttgatagagt gttatcagtc ataactaaat aaagcttgca acaaaattct   11640
ctgacacata gttattcatt gccttaatca ttattttact gcatggtaat tagggacaaa   11700
tggtaaatgt ttcataaaat aattgtattt agtgttactt tataaaatca accaagatt   11760 ttatatttt ttctcctctt tgttagctgc cagtatgcat aaatggcatt aagaatgata   11820
atatttccgg gttcacttaa agctcatatt acacatacac aaaacatgtg ttcccatctt   11880
tatacaaact cacacataca gagctacatt aaaaacaact aataggccag gcacggtggc   11940
tcagacctgt aatcccagca ctttgggagg                                    11970
```

<210> SEQ ID NO 2
<211> LENGTH: 9721
<212> TYPE: DNA
<213> ORGANISM: Homo sapiens
<220> FEATURE:
<223> OTHER INFORMATION: "n" bases throughout the sequence may be A, T, C, G, other or unknown

<400> SEQUENCE: 2

```
agaaagaaag agagagagaa agaaaagaaa gaggaaggaa ggaaggaagg aagaaagaca    60
ggctctgagg aaggtggcag ttcctacaac gggagaacca gtggttaatt tgcaaagtgg   120
atcctgtgga ggcanncaga ggagtcccct aggccaccca gacagggctt ttagctatct   180
```

-continued

```
gcaggccaga caccaaattt caggagggct cagtgttagg aatggattat ggcttatcaa      240
attcacagga aactaacatg ttgaacagct tttagatttc ctgtggaaaa tataacttac      300
taaagatgga gttcttgtga ctgactcctg atatcaagat actgggagcc aaattaaaaa      360
tcagaaggct gcttggagag caagtccatg aaatgctctt tttcccacag tagaacctat      420
ttccctcgtg tctcaaatac ttgcacagag gctcactccc ttggataatg cagagcgagc      480
acgatacctg gcacatacta atttgaataa aatgctgtca aattcccatt cacccattca      540
agcagcaaac tctatctcac ctgaatgtac atgccaggca ctgtgctaga cttggctcaa      600
aaagatttca gtttcctgga ggaaccagga gggcaaggtt tcaactcagt gctataagaa      660
gtgttacagg ctggacacgg tggctcacgc ctgtaatccc aacatttggg aggccgaggc      720
gggcagatca caaggtcagg agatcgagac catcctggct aacatggtga aaccctgtct      780
ctactaaaaa tacaaaaaat tagccgggcg ttggcggcag gtgcctgtag tcccagctgc      840
tggggaggct gaggcaggag aatggtgtga acccgggagg cggaacttgc aggggggcga      900
gatcgtgcca ctgcactcca gcctgggcga cagagtgaga ctctgtctca aaaaaaaaa      960 aaaagtgtta tgatgcagac ctgtcaaaga ggcaaaggag ggtgttccta cactccaggc     1020
actgttcata acctggactc tcattcattc tacaaatggg gggctcccct gggcagatcc     1080
ctggagcagg cactttgctg gtgtctcggt taaagagaaa ctgataactc ttggtattac     1140
caagagatag agtctcagat ggatattctt acagaaacaa tattcccact tttcagagtt     1200
caccaaaaaa tcattttagg cagagctcat ctggcattga tctggttcat ccatgagatt     1260
ggctagggta acagcacctg gtcttgcagg gttgtgtgag cttatctcca gggttgcccc     1320
aactccgtca ggagcctgaa ccctgcatac cgtatgttct ctgccccagc caagaaaggt     1380
caattttctc ctcagaggct cctgcaattg acagagagct cccgaggcag agaacagcac     1440
ccaaggtaga gacccacacc ctcaatacag acagggaggg ctattggccc ttcattgtac     1500
ccatttatcc atctgtaagt gggaagattc ctaaacttaa gtacaaagaa gtgaatgaag     1560
aaaagtatgt gcatgtataa atctgtgtgt cttccacttt gtcccacata tactaaattt     1620
aaacattctt ctaacgtggg aaaatccagt atttttaatgt ggacatcaac tgcacaacga     1680
ttgtcaggaa aacaatgcat atttgcatgg tgatacattt gcaaatgtg tcatagtttg      1740 ctactccttg cccttccatg aaccagagaa ttatctcagt ttattagtcc cctcccctaa     1800
gaagcttcca ccaatactct tttcccctt cctttaactt gattgtgaaa tcaggtattc      1860
aacagagaaa tttctcagcc tcctacttct gcttttgaaa gctataaaaa cagcgaggga     1920
gaaactggca gataccaaac ctcttcgagg cacaaggcac aacaggctgc tctgggattc     1980
tcttcagcca atcttcattg ctcaagtatg actttaatct tccttacaac taggtgctaa     2040
gggagtctct ctgtctctct gcctctttgt gtgtatgcat attctctctc tctctctctt     2100
tctttctctg tctctcctct ccttcctctc tgcctcctct ctcagctttt tgcaaaaatg     2160
ccaggtgtaa tataatgctt atgactcggg aaatattctg ggaatggata ctgcttatct     2220
aacagctgac accctaaagg ttagtgtcaa agcctctgct ccagctctcc tagccaatac     2280
attgctagtt gggggtttggt ttagcaaatg cttttctcta gacccaaagg acttctcttt     2340
cacacattca ttcatttact cagagatcat ttctttgcat gactgccatg cactggatgc     2400
tgagagaaat cacacatgaa cgtagccgtc atggggaagt cactcatttt ctccttttta     2460
cacaggtgtc tgaagcagcc atggcagaag tacctgagct cgccagtgaa atgatggctt     2520
```

-continued

| | |
|---|---|
| attacaggtc agtggagacg ctgagaccag taacatgagc aggtctcctc tttcaagagt | 2580 |
| agagtgttat ctgtgcttgg agaccagatt tttcccctaa attgcctctt tcagtggcaa | 2640 |
| acagggtgcc aagtaaatct gatttaaaga ctactttccc attacaagtc cctccagcct | 2700 |
| tgggacctgg aggctatcca gatgtgttgt tgcaagggct tcctgcagag gcaaatgggg | 2760 |
| agaaaagatt ccaagcccac aatacaagga atcccttttgc aaagtgtggc ttggagggag | 2820 |
| agggagagct cagattttag ctgactctgc tgggctagag gttaggcctc aagatccaac | 2880 |
| agggagcacc agggtgccca cctgccaggc ctagaatctg ccttctggac tgttctgcgc | 2940 |
| atatcactgt gaaacttgcc aggtgtttca ggcagctttg agaggcaggc tgtttgcagt | 3000 |
| ttcttatgaa cagtcaagtc ttgtacacag ggaaggaaaa ataaacctgt ttagaagaca | 3060 |
| taattgagac atgtccctgt ttttattaca gtggcaatga ggatgacttg ttctttgaag | 3120 |
| ctgatggccc taaacagatg aaggtaagac tatgggttta actcccaacc caaggaaggg | 3180 |
| ctctaacaca gggaaagctc aaagaaggga gttctgggcc actttgatgc catggtattt | 3240 |
| tgttttagaa agactttaac ctcttccagt gagacacagg ctgcaccact tgctgacctg | 3300 |
| gccacttggt catcatatca ccacagtcac tcactaacgt tggtggtggt ggccacactt | 3360 |
| ggtggtgaca ggggaggagt agtgataatg ttcccatttc atagtaggaa gacaaccaag | 3420 |
| tcttcaacat aaatttgatt atccttttaa gagatggatt cagcctatgc caatcacttg | 3480 |
| agttaaactc tgaaaccaag agatgatctt gagaactaac atatgtctac ccctttttgag | 3540 |
| tagaatagtt ttttgctacc tggggtgaag cttataacaa caagacatag atgatataaa | 3600 |
| caaaaagatg aattgagact tgaaagaaaa ccattcactt gctgtttgac cttgacaagt | 3660 |
| cattttaccc gctttggacc tcatctgaaa aataaagggc tgagctggat gatctctgag | 3720 |
| attccagcat cctgcaacct ccagttctga aatattttca gttgtagcta agggcatttg | 3780 |
| ggcagcaaat ggtcattttt cagactcatc cttacaaaga gccatgttat attcctgctg | 3840 |
| tcccttctgt tttatatgat gctcagtagc cttcctaggt gcccagccat cagcctagct | 3900 |
| aggtcagttg tgcaggttgg aggcagccac ttttctctgg ctttatttta ttccagtttg | 3960 |
| tgatagcctc ccctagcctc ataatccagt cctcaatctt gttaaaaaca tatttcttta | 4020 |
| gaagttttaa gactggcata acttcttggc tgcagctgtg ggaggagccc attggcttgt | 4080 |
| ctgcctggcc tttgccccccc attgcctctt ccagcagctt ggctctgctc caggcaggaa | 4140 |
| attctctcct gctcaacttt cttttgtgca cttacaggtc tctttaactg tctttcaagc | 4200 |
| ctttgaacca ttatcagcct taaggcaacc tcagtgaagc cttaatacgg agcttctctg | 4260 |
| aataagagga aagtggtaac atttcacaaa aagtactctc acaggatttg cagaatgcct | 4320 |
| atgagacagt gttatgaaaa aggaaaaaaa agaacagtgt agaaaaattg aatacttgct | 4380 |
| gagtgagcat aggtgaatgg aaaatgttat ggtcatctgc atgaaaaagc aaatcatagt | 4440 |
| gtgacagcat tagggataca aaagatata gagaaggtat acatgtatgg tgtaggtggg | 4500 |
| gcatgtacaa aaagatgaca agtagaatcg ggatttattc taaagaatag cctgtaaggt | 4560 |
| gtccagaagc cacattctag tcttgagtct gcctctacct gctgtgtgcc cttgagtaca | 4620 |
| cccttaacct ccttgagctt cagagaggga taatcttttt atttattttt attttatttt | 4680 |
| gttttgtttt gttttgtttt gttttatgag acagagtctc actctgttgc ccaggctgga | 4740 |
| gtgcagtggt acaatcttgg cttactgcat cctccacctc ctgagttcaa gcgattctcc | 4800 |
| ttcctcagtc tcctgaatag ctaggattac aggtgcaccc caccacaccc agctaatttt | 4860 |
| tgtatttttta gtagagaagg ggtttcgcca tgttggccag gctggttttg aagtcctgac | 4920 |

```
ctaaatgatt catccacctc ggcttcccaa agtgctggga ttacaggcat gagccaccac    4980
gcctggccca gagagggatg atctttagaa gctcgggatt cttcaagcc ctttcctcct    5040 ctctgagctt tctactctct gatgtcaaag catggttcct ggcaggacca cctcaccagg    5100
ctccctccct cgctctctcc gcagtgctcc ttccaggacc tggacctctg ccctctggat    5160
ggcggcatcc agctacgaat ctccgaccac cactacagca agggcttcag gcaggccgcg    5220
tcagttgttg tggccatgga caagctgagg aagatgctgg ttccctgccc acagaccttc    5280
caggagaatg acctgagcac cttctttccc ttcatctttg aagaaggtag ttagccaaga    5340
gcaggcagta gatctccact tgtgtcctct tggaagtcat caagcccag ccaactcaat    5400 tcccccagag ccaaagccct ttaaaggtag aaggcccagc ggggagacaa aacaaagaag    5460
gctggaaacc aaagcaatca tctctttagt ggaaactatt cttaaagaag atcttgatgg    5520
ctactgacat ttgcaactcc ctcactcttt ctcaggggcc tttcacttac attgtcacca    5580
gaggttcgta acctccctgt gggctagtgt tatgaccatc accattttac ctaagtagct    5640
ctgttgctcg gccacagtga gcagtaatag acctgaagct ggaacccatg tctaatagtg    5700
tcaggtccag tgttcttagc cacccactc ccagcttcat ccctactggt gttgtcatca    5760
gactttgacc gtatatgctc aggtgtcctc caagaaatca aattttgcca cctcgcctca    5820
cgaggcctgc ccttctgatt ttatacctaa acaacatgtg ctccacattt cagaacctat    5880
cttcttcgac acatgggata acgaggctta tgtgcacgat gcacctgtac gatcactgaa    5940
ctgcacgctc cgggactcac agcaaaaaag cttggtgatg tctggtccat atgaactgaa    6000
agctctccac ctccagggac aggatatgga gcaacaaggt aaatggaaac atcctggttt    6060
ccctgcctgg cctcctggca gcttgctaat tctccatgtt ttaaacaaag tagaaagtta    6120
atttaaggca aatgatcaac acaagtgaaa aaaatatta aaaaggaata tacaaacttt    6180
ggtcctagaa atggcacatt tgattgcact ggccagtgca tttgttaaca ggagtgtgac    6240
cctgagaaat tagacggctc aagcactccc aggaccatgt ccacccaagt ctcttgggca    6300
tagtgcagtg tcaattcttc cacaatatgg ggtcatttga tggacatggc ctaactgcct    6360
gtgggttctc tcttcctgtt gttgaggctg aaacaagagt gctggagcga taatgtgtcc    6420
atccccctcc ccagtcttcc ccccttgccc caacatccgt cccacccaat gccaggtggt    6480
tccttgtagg gaaattttac cgcccagcag gaacttatat ctctccgctg taacgggcaa    6540
aagtttcaag tgcggtgaac ccatcattag ctgtggtgat ctgcctggca tcgtgccaca    6600
gtagccaaag cctctgcaca ggagtgtggg caactaaggc tgctgacttt gaaggacagc    6660
ctcactcagg gggaagctat ttgctctcag ccaggccaag aaaatcctgt ttctttggaa    6720
tcgggtagta agagtgatcc cagggcctcc aattgacact gctgtgactg aggaagatca    6780
aaatgagtgt ctctctttgg agccactttc ccagctcagc ctctcctctc ccagtttctt    6840
cccatgggct actctctgtt cctgaaacag ttctggtgcc tgatttctgg cagaagtaca    6900
gcttcacctc tttcctttcc ttccacattg atcaagttgt tccgctcctg tggatgggca    6960
cattgccagc cagtgacaca atggcttcct tccttccttc cttcagcatt taaaatgtag    7020
accctctttc attctccgtt cctactgcta tgaggctctg agaaaccctc aggcctttga    7080
ggggaaaccc taaatcaaca aaatgaccct gctattgtct gtgagaagtc aagttatcct    7140
gtgtcttagg ccaaggaacc tcactgtggg ttcccacaga ggctaccaat tacatgtatc    7200
ctactctcgg ggctaggggt tggggtgacc ctgcatgctg tgtccctaac cacaagaccc    7260
```

-continued

```
ccttctttct tcagtggtgt tctccatgtc ctttgtacaa ggagaagaaa gtaatgacaa    7320
aatacctgtg gccttgggcc tcaaggaaaa gaatctgtac ctgtcctgcg tgttgaaaga    7380
tgataagccc actctacagc tggaggtaag tgaatgctat ggaatgaagc ccttctcagc    7440
ctcctgctac cacttattcc cagacaattc accttctccc cgcccccatc cctaggaaaa    7500
gctgggaaca ggtctatttg acaagttttg cattaatgta aataaattta acataatttt    7560
taactgcgtg caaccttcaa tcctgctgca gaaaattaaa tcattttgcc gatgttatta    7620
tgtcctacca tagttacaac cccaacagat tatatattgt tagggctgct ctcatttgat    7680
agacaccttg ggaaatagat gacttaaagg gtcccattat cacgtccact ccactcccaa    7740
aatcaccacc actatcacct ccagctttct cagcaaaagc ttcatttcca agttgatgtc    7800
attctaggac cataaggaaa atacaataa aaagcccctg gaaactaggt acttcaagaa    7860
gctctagctt aattttcacc cccccaaaaa aaaaaaattc tcacctacat tatgctcctc    7920
agcatttggc actaagtttt agaaaagaag aagggctctt ttaataatca cacagaaagt    7980
tgggggccca gttacaactc aggagtctgg ctcctgatca tgtgacctgc tcgtcagttt    8040
cctttctggc caacccaaag aacatctttc ccataggcat ctttgtccct tgccccacaa    8100
aaattcttct ttctctttcg ctgcagagtg tagatcccaa aaattccca agaagaaga    8160 tggaaaagcg atttgtcttc aacaagatag aaatcaataa caagctggaa tttgagtctg    8220
cccagttccc caactggtac atcagcacct ctcaagcaga aaacatgccc gtcttcctgg    8280
gagggaccaa aggcggccag gatataactg acttcaccat gcaatttgtg tcttcctaaa    8340
gagagctgta cccagagagt cctgtgctga atgtggactc aatccctagg gctggcagaa    8400
agggaacaga aaggttttg agtacggcta tagcctggac tttcctgttg tctacaccaa    8460
tgcccaactg cctgccttag ggtagtgcta agaggatctc ctgtccatca gccaggacag    8520
tcagctctct cctttcaggg ccaatcccca gcccttttgt tgagccaggc ctctctcacc    8580
tctcctactc acttaaagcc cgcctgacag aaaccacggc cacatttggt tctaagaaac    8640
cctctgtcat tcgctcccac attctgatga gcaaccgctt ccctatttat ttatttattt    8700
gtttgtttgt tttgattcat tggtctaatt tattcaaagg gggcaagaag tagcagtgtc    8760
tgtaaaagag cctagttttt aatagctatg gaatcaattc aatttggact ggtgtgctct    8820
ctttaaatca gtcctttaa ttaagactga aatatataa gctcagatta tttaaatggg    8880
aatatttata aatgagcaaa tatcatactg ttcaatggtt ctgaaataaa cttcactgaa    8940
gaaaaaaaaa aagggtctc tcctgatcat tgactgtctg gattgacact gacagtaagc    9000
aaacaggctg tgagagttct tgggactaag cccactcctc attgctgagt gctgcaagta    9060
cctagaaata tccttggcca ccgaagacta tcctcctcac ccatcccctt tatttcgttg    9120
ttcaacagaa ggatattcag tgcacatctg gaacaggatc agctgaagca ctgcagggag    9180
tcaggactgg tagtaacagc taccatgatt tatctatcaa tgcaccaaac atctgttgag    9240
caagcgctat gtactaggag ctgggagtac agagatgaga acagtcacaa gtccctcctc    9300
agataggaga ggcagctagt tataagcaga acaaggtaac atgacaagta gagtaagata    9360
gaagaacgaa gaggagtagc caggaaggag ggaggagaac gacataagaa tcaagcctaa    9420
agggataaac agaagatttc cacacatggg ctgggccaat tgggtgtcgg ttacgcctgt    9480
aatcccagca ctttgggtgg caggggcaga aagatcgctt gagcccagga gttcaagacc    9540
agcctgggca acatagtgag actcccatct ctacaaaaaa taaataaata aataaaacaa    9600
tcagccaggc atgctggcat gcacctgtag tcctagctac ttgggaagct gacactggag    9660
```

-continued

| gattgcttga gcccagaagt tcaagactgc agtgagctta tccgttgacc tgcaggtcga | 9720 |
| c | 9721 |

<210> SEQ ID NO 3
<211> LENGTH: 12565
<212> TYPE: DNA
<213> ORGANISM: Homo sapiens

<400> SEQUENCE: 3

| gtcgacctgc aggtcaacgg atctgagagg agagtagctt cttgtagata acagttggat | 60 |
| tatataccat gtcctgatcc ccttcatcat ccaggagagc agaggtggtc accctgatag | 120 |
| cagcaagcct gggggctgca gcttggtggg tagaggtact caggggtaca gatgtctcca | 180 |
| aacctgtcct gctgccttag ggagcttcta ataagttgat ggatttggtt aaaattaact | 240 |
| tggctacttg gcaggactgg gtcagtgagg accaacaaaa agaagacatc agattatacc | 300 |
| ctgggggttt gtatttcttg tgtttctttc tcttctttgt actaaaatat ttacccatga | 360 |
| ctgggaaaga gcaactggag tctttgtagc attatcttag caaaaattta caagtttgg | 420 |
| aaaacaatat tgcccatatt gtgtggtgtg tcctgtgaca ctcaggattc aagtgttggc | 480 |
| cgaagccact aaatgtgaga tgaagccatt acaaggcagt gtgcacatct gtccacccaa | 540 |
| gctggatgcc aacatttcac aaatagtgct tgcgtgacac aaatgcagtt ccaggaggcc | 600 |
| caaatgaaaa tgtttgtact gaaatttgtt aaagcttccc gacaaactag atttatcagt | 660 |
| aaggattgtt ttctgcaagg gggatgaaac ttgtggggtg agccatttgg gctgaggagg | 720 |
| agggaggttg gagctgagaa atgtggagac aatttcccct tagaaggact gaatctccct | 780 |
| gcctctctgg ggtgcggcag ccagcaggat ccaatggtgt atatgtctcc ccagctcccc | 840 |
| attcagtgat atcatgtcag tagcttgaaa ttatccgtgg tgggagtatt atgtcatgga | 900 |
| aattggcaaa tggaaacttt tattggagat tcaattgtta aacttttacc agcacaacac | 960 |
| tgccctgcct tcagagtcaa tgaccctatc caagtttaat ccatctgtcc actgtctcca | 1020 |
| acacgatctt tataaaacac acctgacaac attacccttt tattcagttt tttaaaagat | 1080 |
| aagtttccag ctcatcgggg tggctttaaa ggccatttct cctctggacc tcacccaact | 1140 |
| tttcaaatca cttttcctac ccctacctct aaatgctact caaactccag ccatcctgaa | 1200 |
| taataagact tttgaaaagt agattatggg ctgggcacag tggctcacac ctgtaatccc | 1260 |
| agcactttgg gaggccaaga tgggtggatc acctgaggtc gggagttcga gaccagcctg | 1320 |
| actaacatag tgaaaccctg tctctactaa aaatacaaaa ttagttgggg gtggtggcac | 1380 |
| aagcctgtaa tcccagctac tcaggaggtt gaggcagggg aattgcttga acctgggagg | 1440 |
| cggaggttgc ggtgagccta gattgctcca ctgcactcca gcctgggcaa caagagcgaa | 1500 |
| actccatctc aaaaaaataa ataaataaat aaagtagatt acatcagata cctctggcct | 1560 |
| aggttgttta tgaccaactc tcctgctgag aataactaga aaagctagac aaaacatatt | 1620 |
| tccaaaagat ctctttggag gcatcagaga atggccaagg ctgtaaggaa ctgcctgagc | 1680 |
| ccagagaggt ggagcccagc actggtgccc tttactcctg gggacatgtg ctggtttcaa | 1740 |
| aaacttcagc tgagcttttg agcattcatg gaacttggtg ggggagatga aatttgtacc | 1800 |
| ttaaatcctg cctacaggga gggtccctga taatccccac ccaatttgga aatctgggtc | 1860 |
| agccttcaca ggtactgaag ccctcctctg aatgatctca agtcctgcta gggtagaggt | 1920 |
| tacctgcttt tgaaaggctc ctggcctacc tgtgcagcag gagcaaaagt gaaccatctc | 1980 |

-continued

```
aggtacaga taacaatcat ccagagcctt gaatgacctc tactgtgctt aatatatagt   2040
attcagcagt cagtaaaaag gatttaggca catgcaagat gacctgtgta tcagggagaa   2100
ataggcaata aattgagatc cagcagggat ttgaatcatg gatttgaatc aggggcagcc   2160
ttcgaaagaa ctatggagaa tatactcaga tttaaaacat aagattggaa tttttggcag   2220
agaactaaca actgtacaaa aaaggaacca aatggaaatc ctagaactga agatgcaat    2280 taaccgatgt tgagaaatag ccaacatcta ttgaacactt cccatgtgga cagctgtgct   2340
aaacacttta caggcatcaa cataagatgt gtccccttac agcagtgcag tgtccctcct   2400
aagacatgga cagcctggtt tccctatctc tctgcttcat caaaacccct ttacgtgggg   2460
cttagacact cctgttgtct ctagtgtcta gtagcacagg gctcagcaca tggaagccac   2520
tagatacaat ttgatgacca ggacctccga tgaaagccat gggtgctgat tgggaaggca   2580
ttgtctttta tgtgctatgg tcttaaagct tcatccagga agcagaactc ggggggtgct   2640
gaggacccag aaccgagaat aagattagtc agagatttcc tgtgggcaga aatcataagg   2700
acgccaactg tttgggtgag ataagacgaa accaagagtg gacttgtggc cagaagcgtg   2760
aggaagaggg agagagcttc ccttgtcccc tttcttcctc tccctaagcc acagtgattg   2820 acagccccc cgctttggag tcagagcagg cttgagactg gactgggaaa ggaggtggg    2880 tcaggataca gagcaggaag gctgggagtg cagggcagga gcaaggggct ggggcattca   2940
ttgtgcctga tctctcccac tttacctggg gtaaagaagc atatgcaaaa gccacggtgt   3000
gagtatttcc caagtgccag ggtcaggca tgattcatca cgtgcagcat ttcattcaat    3060
ccttatagta accgatgatg tggcttctat tattagctct atcagataat gaaactgaga   3120
ccaagacagg ctctgcacat tgtgtgggt aatgacacag ggggattcag acctagactc    3180
cataactcct gccccaggga ccaccccac cctcaccctg tgcatgtcga caaggacag    3240 actgggccac ttctcaggac acagcgggga atgacacag agcagggagg ttccaggagc   3300
cccgagcgtc ttttctccag gagaatactc tctgaattca gactggggtc agagaaacat   3360
ttacccagga gccgcagtgt gggtggggct ttttacttga aacgctgtct gaaggcagtg   3420
gcaggatgaa ctctccaccc taccttggca agccacttct cttctgcaat ctgtaaggac   3480
attgttgaga gaattatggt cttccaattc cggagggttg aagaaagaca aataggagag   3540
aacctatcat agtcaggtgc tagctgcctt ctctttcaga gagtgtgaga ataaagtgat   3600
acacttgatt attagcaaat actttggaaa ttttaaacgc taatattcaa cacactctgg   3660
aagaggcaaa taagtagaca ggttcatata catcatctcc ttcagctagt cctcacaaaa   3720
acaaacaaat gaataaacaa aattcttctt tggccctcat aggaagacac tgtttcttga   3780
acgtgtttca aaaggatgg gtgactcact caaggtcaca ctgtttatga ggacagtaca    3840
ggaatacaga catgccattt tgcctgaaaa aatccatcac ccagggaggt gacacaattt   3900
tgcagaaatg ttctatttcc tctgaaggat acattcttta aacctttggg aaattcattc   3960
atagtcttcc tcctttgaag gattactctc tggacacaaa gtgtttgatt ctgatttgtt   4020
ggttggaaga tgtgttggtt gagagaaaga ttctgatttg ttggttgaaa atagactcat   4080
caagatcaac tgctgtagta gtaaatattt tgacattttg tctgtattcc tgtgctgccc   4140
tcacaagctg catcaccttg agtgagtcat tcatactttt ttgtttgttt ttgttttgga   4200
gatggagtct tactctgttg cctaggctgg agtgcgtgg cgtgatcttg gctcactgcg    4260
acctccatct cctgggttca gtgatcctc ctgcctcagc ctcccgagta gctgggatta    4320
caggcacatg ccaccatccc tgctaatttt tgcattttca gtagagacgg agtttcacca   4380
```

```
tgttggtcag gttggtcttg aactcctgac ctcaggtgat ccgcccacct cagcctcccc    4440
aagtgctggg attacaggtg tgagccaccg tgcccagccc agccatcatt tttgaaacac    4500
gtttgagaaa tagtgtcttc ctttgagggc caaggagaca ttttttttgt ttatttgttt    4560
gtttttgtga ggactagctg aaggggtga tgtatattaa cctgcctact tatttgcctc     4620
ttcccagagt gtgatgaata ttagggttta agtttctga agcatttgtt aataaagccc     4680
ggggctggag gtcagaagac ctggatttct ctgcatactt ttgccatcag caagctgtgt    4740
gaccttggac agatcccttt tttgtctaaa tctttctgag tcttcttgaa aacaatgcca    4800
ggttgggaca ggatgattgc caagctcccg tccagctcta aaacactgca acgtatgctt    4860
ctgcaccagc actgtccatc ctgtagatca tgcagaaatt ctcttcaact ttttcctacc    4920
cataaaatag gagcatgctt accttttttcc taatgttcca ggccccgggt ctagatattg    4980
taagtaagga agttaatgtg tatcagagcc cattatgggc cagaagttct cctcttcctt    5040
cctacacctg cttcctccct ccctccctcc ctctttccct tccttccttc catccatttg    5100
tgaagaagac atgatcaccc tcattctgag agtgaagaga cagaggctca actaatgaaa    5160
tgatttgttc aaggtcacac gggtggcaca aggcaagtgg cagaggttga atttagaccc    5220
attcctgtcc aaatgctgag tttatgtcat cgtcccgaga ccataacttt aaagatgtaa    5280
gatagtggga aaagagttga tttcaaagca cctctcagaa ggactcactt tacatcaggg    5340
gtcagcagac tcaggccaaa tccggtccat tccccgcttt tgcaaagaaa gttgtagtgg    5400
aacacagcta ggcttattga tttatggatt gccaacgtcc ttttgtgaaa cagacagctg    5460
agctgagtaa tcgtggcgca caaaacctaa aatatttact atctcgtcct ttacagaatg    5520
tttgccaatc tatggtccgg agtccaaggc tgtccatttt tcaaagaaca caaagtgaca    5580
tgagactgtc ccatgtgcag ggagccctat cattttatta tgaaaaaacg gcctttctgc    5640
tcaaatctgt tttttaaaaa gtcaacaaac agactctggg tacctgtcag gaacagtagg    5700
gagtttggtt tccattgtgc tcttcttccc aggaactcaa tgaagggaa atagaaatct     5760 taattttggg gaaattgcac aggggaaaaa ggggagggaa tcagttacaa cactccattg    5820
cgacacttag tggggttgaa agtgacaaca gcaagggttt ctcttttttgg aaatgcgagg    5880 agggtatttc cgcttctcgc agtggggcag ggtggcagac gcctagcttg ggtgagtgac    5940 tatttctttta taaccacaa ctctgggccc gcaatggcag tccactgctt gctgcagtca    6000
cagaatggaa atctgcagag gcctccgcag tcacctaatc actctcctcc tcttcctgtt    6060
ccattcagag acgatctgcc gaccctctgg gagaaaatcc agcaagatgc aagccttcag    6120
gtaaggctac cccaaggagg agaaggtgag ggtggatcag ctggagactg gaaacatatc    6180
acagctgcca gggctgccag gccagagggc ctgagaactg ggtttgggct ggagaggatg    6240
tccattattc aagaaagagg ctgttacatg catgggcttc aggacttgtg tttcaaaata    6300
tcccagatgt ggatagtgcg accggagggc tgtcttactt tcccagagac tcaggaaccc    6360
agtgagtaat agatgcatgc caaggagtgg gactgcgatt caggcctagt tgaatgtgct    6420
gacagagaag cagagagggg caccaggggc acagcccgaa ggcccagact gatatgggca    6480
aggcctgtct gtgctgacat gtcggagggt cccactctcc agggaccttg gtttccccgt    6540
ctgtgacatc tgtgacatga gagtcacgat aactccttgt gtgccttaca gggttgttgt    6600
gaaaattaaa tgcacagata atagcgtaac agtattccgt gcattgtaaa gagcctgaaa    6660
accattatga tttgaaaatg gaatcggctt tgtgagacca tcactattgt aaagatgtga    6720
```

```
tgctgataga aatgacagga ctgcttgtgc atgccctctg cagtgtgaca ttccagcagt      6780
gaaatcatgt tggggtgact tctcccccac tctgacctttt atgtttgtct gggccgaggc     6840
tgcaagtcgg gctctgtggg tgtatgagtg acaagtctct cccttccaga tatggggact     6900
gtctgcttcc ctaggttgcc tctccctgct ctgatcagct agaagctcca ggagatcctc     6960
ctggaggccc cagcaggtga tgtttatccc tccagactga ggctaaatct agaaactagg     7020
ataatcacaa acaggccaat gctgccatat gcaaagcact ttggtttgcc tggccacccc     7080
tcgtcgagca tgtgggctct tcagagcacc tgatgaggtg ggtacagtta gccacacttc     7140
acaggtgaag aggtgaggca caggtcccag gtcaggctgg ccggagctct gtttattacg     7200
tctcacagct ttgagtcctg ctctcaacca gagaggccct ttaccaagaa gaaaggattg     7260
ggacccagaa tcaggtcact ggctgaggta gagaggaagc cgggttgttc ccaagggtag     7320
ctgctcctgc aggactctga gcaggtcacc agctaatgga ggaaaggctc tagggaaaga     7380
cccttctggt ctcagactca gagcgagtta gctgcaaggt gttccgtctc ttgaaacttc     7440
tacctaggtg ctatggtagc cactagtctc aggtggctat ttaaatttat acttaaatga     7500
atgaaaatag aagaaaattt aaaatccaga cccttggtca cactatccac atttaaagag     7560
gtcaatagcc acatgtggtt agtggccacc ctattgggca gtgcagctac agaacatttt     7620
tgcatcccag aaagttcttt tggatgttgc tgctctacag catgctttgc tgaaacagaa     7680
gtgccttccc tgggaatctc agatgggaag caagtaagga ggggagtcaa atgtgggctc     7740
actgctcacc agctgtgagg gttgggcctg cctcttaacc attgtcagcc tcagtcttct     7800
catccatgca tgccgtgggt atactaaaat actataccccc tggaagagct ggatgcaaat     7860
ttgacaagtt ctgggggaca caggaaggtg ccaagcacaa ggctgggcac atggtggctg     7920
tgcactacag ctgagtcctt ttccttttca gaatctggga tgttaaccag aagaccttct     7980
atctgaggaa caaccaacta gttgctggat acttgcaagg accaaatgtc aatttagaag     8040
gtgagtggtt gccaggaaag ccaatgtatc tgggcatcac gtcactttgc ccgtctgtct     8100
gcagcagcat ggcctgcctg cacaaaccct aggtgcaatg tcctaatcct tgttgggtct     8160
ttgtattcaa gtttgaagct gggagggcct ggctactgaa gggcacatat gagggtagcc     8220
tgaagagggt gtggagaggt agagtctagg tcagaggtca gtgcctatag caagtggtc      8280 ccagggccac agctgggaag ggcaaatacc agaaggcaag gttgaccatt cccttcctca     8340
agtgcctatt aaggctccat gttcctatgt tgttcaaacc ctaactcaat cccaaattaa     8400
tccaccatgt ataaggttga gctatgtctc ttattcctgg acaccatact cagccatatc     8460
tggtccacac attaacagct ggatgacctt gaagaagctt cacccactct gttcctcagc     8520
tttcccttca gtgggatgat atcaactgga caacaggatg tgcgattctt ttagttccag     8580
ccttccagga tgttttcact cccctgtttg ttgttgtagg atggtattac ctccaccttc     8640
ccaccttccc tatgccctgg ttctgtctcc tgtgcctcgc tctgaaagtg gatgagacct     8700
acaattcctg tcctggtagt tctcctaatg aacacactga agcacgagga agctgagatt     8760
tttgttgcta catgagagca tggaggcctc ttagggagag aggaggttca gagactccta     8820
ggctcctggt ggagcccac tcatggcctt gttcattttc cctgccccctc agcaacactc     8880 ctattgacct ggagcacagg tatcctgggg aaagtgaggg aaatatggac atcacatgga     8940
acaacatcca ggagactcag gcctctagga gtaactgggt agtgtgcatc ctggggaaag     9000
tgagggaaat atggacatca catggaacaa catccaggag actcaggcct ctaggagtaa     9060
ctgggtagtg tgcatcctgg ggaaagtgag ggaaatatgg acatcacatg gaacaacatc     9120
```

-continued

```
caggagactc aggcctctag gagtaactgg gtagtgtgca tcctgggaaa agtgagggaa      9180
atatggacat cacatggaac aacatccagg agactcaggc ctctaggagt aactgggtag      9240
tgtgcttggt ttaatcttct atttacctgc agaccaggaa gatgagacct ctctgcccett    9300 ctgacctcgg gattttagtt ttgtggggac caggggagat agaaaaatac ccggggtctc     9360
ttcattattg ctgcttcctc ttctattaac ctgaccctcc cctctgttct tccccagaaa     9420
agatagatgt ggtacccatt gagcctcatg ctctgttctt gggaatccat ggagggaaga     9480
tgtgcctgtc ctgtgtcaag tctggtgatg agaccagact ccagctggag gtaaaaacat     9540
gctttggatc tcaaatcacc ccaaaaccca gtggcttgaa acaaccaaaa ttttttctta     9600
tgattctgtg ggttgaccag gattagctgg gtagttctgt tccatgtggt ggaacatgct     9660
ggggtcactt tggaagctgc attcagcaga gtgccaggct tgcgctgggc atccaaggtg     9720
gtccctcatc ctccaggctc tctttccatg tgatctctca gtgtttaaga gttagttgga     9780
gcttccttac agcatggcgg ctgacttcca aaagggatta ttccaaaaag agcctcaaca     9840
tgcaggcgct tattatgact tctgcttgca tcatcctatt ggccaaagcc agtcacgtgg     9900
ctaagtctag cccctgtga gaggagactg cataagagtg tgaacaccag gagacacggt      9960 cactggggc caccactgta accatctacc acaggacctg aatctctgtg tgctactccc     10020
ttgctcaagg gccccctac ccacgcagac ctgctgtctt ctagcaaagc ccatcctcag     10080 gaccttctc ttccaatcct tattgactca aattgattag ttggtgctcc acccagagcc     10140
ctgtgctcct ttatctcatg taatgttaat gggtttccca gccctgggaa aacatggctt    10200
tgtctcaggg gcttgctgga tgcaacctta acctcaatgt gagtgccat actgtggcac    10260 tgtcccatcc ctcaccaggg acactgttct ggagggtgac tgcctgttct gtgaggagtg    10320
gggatggcta ggacattgca tggaacacac caccacccca tcttctcaga gctcaaaccc    10380
tgacagaaca ccagctccac aggccttggc ttctgctgat ggtgccgtgt atttaccaga    10440
cttagtggtc caaggccaga gtggcagatt tcccaaagtc aaggtgtgac agtgggacag    10500 cctcttttgtg tctttgctgt cctaagaaac ctgggccagg ccaggcgcag tggctcacgc    10560
cttgtaatcc cagcactttg agaggccaag gtgggcagat cacgaggtca ggagtttgag    10620
accagcctgg ccaacattgg tgaaaccctg tctctattaa aaatagaaaa cattagacag    10680
gtgtggtggt gcatgcctgt aatcccagct actcaggagg ctgaggcagg agaatcgctt    10740
gaacccagga ggtggaggtt gcagtgagcc gagattgtgc cactgcactc cagcctaggc    10800
gacagagcaa gactccgtct cgggaaaatt aattaataaa taaataaacc taggtcccag    10860
agtcccacag aatggcagac aggagcacct gggggctttt agggtatggc atttccctg     10920 tactaactct gggctgtcca gaggcgattt catggcgtgg agtggagagg gaggcagcac    10980
aggacttcct aggcctcagc tctcacctgc ccatcttttg atttccaggc agttaacatc    11040
actgacctga gcgagaacag aaagcaggac aagcgcttcg ccttcatccg ctcagacagt    11100
ggccccacca ccagttttga gtctgccgcc tgccccggtt ggttcctctg cacagcgatg    11160
gaagctgacc agcccgtcag cctcaccaat atgcctgacg aaggcgtcat ggtcaccaaa    11220
ttctacttcc aggaggacga gtagtactgc ccaggcctgc ctgttcccat tcttgcatgg    11280
caaggactgc agggactgcc agtcccctg ccccagggct cccggctatg ggggcactga     11340
ggaccagcca ttgaggggtg gaccctcaga aggcgtcaca acaacctggt cacaggactc    11400
tgcctcctct tcaactgacc agcctccatg ctgcctccag aatggtcttt ctaatgtgtg    11460
```

-continued

```
aatcagagca cagcagcccc tgcacaaagc ccttccatgt cgcctctgca ttcaggatca      11520
aaccccgacc acctgcccaa cctgctctcc tcttgccact gcctcttcct ccctcattcc      11580
accttcccat gccctggatc catcaggcca cttgatgacc cccaaccaag tggctcccac      11640
accctgtttt acaaaaaaga aaagaccagt ccatgaggga ggttttttaag ggtttgtgga     11700 aaatgaaaat taggatttca tgattttttt ttttcagtcc ccgtgaagga gagcccttca     11760
tttggagatt atgttctttc ggggagaggc tgaggactta aaatattcct gcatttgtga     11820
aatgatggtg aaagtaagtg gtagcttttc ccttctttt cttcttttt tgtgatgtcc       11880 caacttgtaa aaattaaaag ttatggtact atgttagccc cataattttt tttttccttt     11940
taaaacactt ccataatctg gactcctctg tccaggcact gctgcccagc ctccaagctc      12000
catctccact ccagattttt tacagctgcc tgcagtactt tacctcctat cagaagtttc      12060
tcagctccca aggctctgag caaatgtggc tcctgggggt tctttcttcc tctgctgaag     12120
gaataaattg ctccttgaca ttgtagagct tctggcactt ggagacttgt atgaaagatg     12180
gctgtgcctc tgcctgtctc cccaccaggc tgggagctct gcagagcagg aaacatgact     12240
cgtatatgtc tcaggtccct gcagggccaa gcacctagcc tcgctcttgg caggtactca     12300
gcgaatgaat gctgtatatg ttgggtgcaa agttccctac ttcctgtgac ttcagctctg     12360
ttttacaata aaatcttgaa aatgcctata ttgttgacta tgtccttggc cttgacaggc     12420
tttgggtata gagtgctgag gaaactgaaa gaccaatgtg tyttycttac cccagaggct     12480
ggcgcctggc ctcttctctg agagttcttt tcttccttca gcctcactct ccctggataa     12540
catgagagca aatctctctg cgggg                                            12565
```

<210> SEQ ID NO 4
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 4
tgtacctaag cccacccttt agagc                                            25

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 5
tggcctccag aaacctccaa                                                  20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 6
gctgatattc tggtgggaaa                                                  20

<210> SEQ ID NO 7
<211> LENGTH: 20
<212> TYPE: DNA
<213> ORGANISM: Artificial Sequence

```
<220> FEATURE:
<223> OTHER INFORMATION: Description of Artificial Sequence: primer

<400> SEQUENCE: 7
ggcaagagca aaactctgtc                                              20

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 8
atgtatagaa ttccattcct g                                            21

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 9
taaaatcaag tgttgatgta g                                            21

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 10
gggatacagg cgtgagccac cgcg                                         24

<210> SEQ ID NO 11
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 11
ttagtattgc tggtagtatt catat                                        25

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 12
tgttctacca cctgaactag g                                            21

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 13
ttacatatga gccttccatg                                              20
```

<210> SEQ ID NO 14
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 14
ctcaggtgtc ctcgaagaaa tcaaa                                    25

<210> SEQ ID NO 15
<211> LENGTH: 19
<212> TYPE: DNA
<213> ORGANISM: Artificial Sequence
<220> FEATURE:
<223> OTHER INFORMATION: Description of Artificial Sequence: primer

<400> SEQUENCE: 15
gctttmgctg tgagtcccg                                           19

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 16
tggcattgat ctggttcatc                                          20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 17
gtttaggaat cttcccactt                                          20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 18
gaggcgtgag aatctcaaga                                          20

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 19
gtgtcctcaa gtggatctgg                                          20

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 20
gggcaacaga gcaatgtttc t                                              21

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 21
cagtgtgtca gtgtactgtt                                                20

<210> SEQ ID NO 22
<211> LENGTH: 17
<212> TYPE: DNA
<213> ORGANISM: Artificial Sequence
<220> FEATURE:
<223> OTHER INFORMATION: Description of Artificial Sequence: primer

<400> SEQUENCE: 22
ctcagcaaca ctcctat                                                   17

<210> SEQ ID NO 23
<211> LENGTH: 17
<212> TYPE: DNA
<213> ORGANISM: Artificial Sequence
<220> FEATURE:
<223> OTHER INFORMATION: Description of Artificial Sequence: primer

<400> SEQUENCE: 23
tcctggtctg caggtaa                                                   17

<210> SEQ ID NO 24
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 24
ttacgcagat aagaaccagt ttgg                                           24

<210> SEQ ID NO 25
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 25
tttcctggac gcttgctcac ca                                             22

<210> SEQ ID NO 26
<211> LENGTH: 29
<212> TYPE: DNA
<213> ORGANISM: Artificial Sequence
<220> FEATURE:
<223> OTHER INFORMATION: Description of Artificial Sequence: primer

<400> SEQUENCE: 26
ttctatctga ggaacaacca actagtagc                                      29

<210> SEQ ID NO 27

```
<211> LENGTH: 29
<212> TYPE: DNA
<213> ORGANISM: Artificial Sequence
<220> FEATURE:
<223> OTHER INFORMATION: Description of Artificial Sequence: primer

<400> SEQUENCE: 27
caccagactt gacacaggac aggcacatc                                      29

<210> SEQ ID NO 28
<211> LENGTH: 27
<212> TYPE: DNA
<213> ORGANISM: Artificial Sequence
<220> FEATURE:
<223> OTHER INFORMATION: Description of Artificial Sequence: primer

<400> SEQUENCE: 28
cgaccctctg ggagaaaatc cagcaag                                        27

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 29
acacaggaag gtgccaagca                                                20

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 30
tgcagacaga cgggcaaagt                                                20

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 31
ttgtggggac cagggagat                                                 20

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 32
agcctggcac tctgctgaat                                                20
```

DIAGNOSTICS AND THERAPEUTICS FOR DISEASES ASSOCIATED WITH AN IL-1 INFLAMMATORY HAPLOTYPE

CROSS-REFERENCE TO THE RELATED APPLICATION

This application in a continuation of U.S. application Ser. No. 09/345,217, filed Jun. 30, 1999, U.S. Pat. No. 6,268,142, which is a continuation and claims the benefit of PCT/GB98/01481, filed May 21, 1998, which further claims the benefit of GB Application No. 9711040.7, filed May 29, 1997. The contents of each of these priority applications are specifically incorporated herein.

1. BACKGROUND OF THE INVENTION

Genetics of the IL-1 Gene Cluster

The IL-1 gene cluster is on the long arm of chromosome 2 (2q13) and contains at least the genes for IL-1α (IL-1A), IL-1β (IL-1B), and the IL-1 receptor antagonist (IL-1RN), within a region of 430 Kb (Nicklin, et al. (1994 Genomics, 19: 382–4); The agonist molecules, IL-1α and IL-1β, have potent pro-inflammatory activity and are at the head of many inflammnatory cascades. Their actions, often via the induction of other cytolines such as IL-6 and IL-8, lead to activation and recruitment of leukocytes into damaged tissue, local production of vasoactive agents, fever response in the brain and hepatic acute phase response. All three IL-1 molecules bind to type I and to type II IL-1 receptors, but only the type I receptor transduces a signal to the interior of the cell. In contrast, the type II receptor is shed from the cell membrane and acts as a decoy receptor. The receptor antagonist and the type II receptor, therefore, are both anti-inflammatory in their actions.

Inappropriate production of IL-1 plays a central role in the pathology of many autoimmune and inflammatory diseases, including rheumatoid arthritis, inflammatory bowel disorder, psoriasis, and the like. In addition, there are stable inter-individual differences in the rates of production of IL-1, and some of this variation may be accounted for by genetic differences at IL-1 gene loci. Thus, the IL-1 genes are reasonable candidates for determining part of the genetic susceptibility to inflammatory diseases, most of which have a multifactorial etiology with a polygenic component.

Certain alleles from the IL-1 gene cluster are known to be associated with particular disease states. For example, IL-1RN (VNTR) allele 2 has been shown to be associated with osteoporosis (U.S. Pat. No. 5,698,399), nephropathy in diabetes mellitus (Blaklemore, et al. (1996) Hum. Genet. 97(3): 369–74), alopecia areata (Cork, et al., (1995) J. Invest. Dermatol. 104(5 Supp.): 15S–16S Cork et al. (1996) Dermatol Clin 14: 671–8), Graves disease (Blakemore, et al. (1995) J. Clin. Endocrinol. 80(1): 111–5), systemic lupus erythematosus (Blakemore, et al. (1994) Artritis Rheum. 37: 1380–85), lichen sclerosis (Clay, et al. (1994) Hum. Genet 94: 407–10), and ulcerative colitis (Mansfield, et al. (1994) Gastoenterol. 106(3):637–42)).

In addition, the IL-1A allele 2 from marker –889 and IL-1B (TaqI) allele 2 from marker +3954 have been found to be associated with periodontal disease (U.S. Pat. No. 5,686,246; Konmman and diGiovine (1998) Ann Periodont 3: 327–38; Hart and Kornman (1997) Periodontol 2000 14: 202–15; Newman (1997) Compend Contin Educ Dent 18: 881–4; Kornman et al. (1997) J. Clin Periodontol 24: 72–77). The IL-1A allele 2 from marker –889 has also been found to be associated with juvenile chronic arthritis, particularly chronic iridocyclitis (McDowell, et al. (1995) Arthritis Rheum. 38: 221–28). The IL-1B (TaqI) allele 2 from marker +3954 of IL-1B has also been found to be associated with psoriasis and insulin dependent diabetes in DR3/4 patients (di Giovine, et al. (1995) Cytokine 7: 606; Pociot, et al. (1992) Eur J. Clin. Invest. 22: 396–402). Additionally, the IL-1RN (VNTR) allele 1 has been found to be associated with diabetic retinopathy (see U.S. Ser. No. 09/037472, and PCT/GB97/02790). Furthermore allele 2 of IL-1RN (VNTR) has been found to be associated with ulcerative colitis in Caucasian populations from North America and Europe (Mansfield, J. et al., (1994) Gastroenterology 106: 637–42). Interestingly, this association is particularly strong within populations of ethnically related Ashkenazi Jews (PCT WO97125445).

Genotype Screening

Traditional methods for the screening of heritable diseases have depended on either the identification of abnormal gene products (e.g., sickle cell anemia) or an abnormal phenotype (e.g., mental retardation). These methods are of limited utility for heritable diseases with late onset and no easily identifiable phenotypes such as, for example, vascular disease. With the development of simple and inexpensive genetic screening methodology, it is now possible to identify polymorphisms that indicate a propensity to develop disease, even when the disease is of polygenic origin. The number of diseases that can be screened by molecular biological methods continues to grow with increased understanding of the genetic basis of multifactorial disorders.

Genetic screening (also called genotyping or molecular screening), can be broadly defined as testing to determine if a patient has mutations (alleles or polymorphisms) that either cause a disease state or are "linked" to the mutation causing a disease state. Linkage refers to the phenomenon th DNA sequences which are close together in the genome have a tendency to be inherited together. Two sequences may be linked because of some selective advantage of co-inheritance. More typically, however, two polymorphic sequences are co-inherited because of the relative infrequency with which meiotic recombination events occur within the region between the two polymorphisms. The co-inherited polymorphic alleles are said to be in linkage disequilibrium with one another because, in a given human population, they tend to either both occur together or else not occur at all in any particular member of the population Indeed, where multiple polymorphisms in a given chromosomal region are found to be in linkage disequilibrium with one another, they define a quasi-stable genetic "haplotype." In contrast, recombination events occurring between two polymorphic loci cause them to become separated onto distinct homologous chromosomes. If meiotic recombination between two physically linked polymorphisms occurs frequently enough, the two polymorphisms will appear to segregate independently and are said to be in linkage equilibrium.

While the frequency of meiotic recombination between two markers is generally proportional to the physical distance between them on the chromosome, the occurrence of "hot spot" as well as regions of repressed chromosomal recombination can result in discrepancies between the physical and recombinational distance between two markers. Thus, in certain chromosomal regions, multiple polymorphic loci spanning a broad chromosomal domain may be in linkage disequilibrium with one another, and thereby define a broad-spanning genetic haplotype. Furthermore, where a disease-causing mutation is found within or in linkage with this haplotype, one or more polymorphic alleles of the haplotype can be used as a diagnostic or prognostic indicator of the likelihood of developing the disease. This association between otherwise benign polymorphisms and a disease-causing polymorphism occurs if the disease mutation arose in the recent past, so that sufficient time has not elapsed for equilibrium to be achieved through recombination events. Therefore identification of a human haplotype which spans or is linked to a disease-causing mutational change, serves as a predictive measure of an individual's likelihood of having inherited that disease-causing mutation Importantly, such prognostic or diagnostic procedures can be utilized without necessitating the identification and isolation of the actual disease-causing lesion. This is significant because the precise determination of the molecular defect involved in a disease process can be difficult and laborious, especially in the case of multifactorial diseases such as inflammatory disorders.

Indeed, the statistical correlation between an inflammatory disorder and an IL-1 polymorphism does not necessarily indicate that the polymorphism directly causes the disorder. Rather the correlated polymorphism may be a benign allelic variant which is linked to (i.e. in linkage disequilibrium with) a disorder-causing mutation which has occurred in the recent human evolutionary past, so that sufficient time has not elapsed for equilibrium to be achieved through recombination events in the intervening chromosomal segment. Thus, for the purposes of diagnostic and prognostic assays for a particular disease, detection of a polymorphic allele associated with that disease can be utilized without consideration of whether the polymorphism is directly involved in the etiology of the disease. Furthermore, where a given benign polymorphic locus is in linkage disequilibrium with an apparent disease-causing polymorphic locus, still other polymorphic loci which are in linkage disequilibrium with the benign polymorphic locus are also likely to be in linkage disequilibrium with the disease-causing polymorphic locus. Thus these other polymorphic loci will also be prognostic or diagnostic of the likelihood of having inherited the disease-causing polymorphic locus. Indeed, a broad-spanning human haplotype (describing the typical pattern of co-inheritance of alleles of a set of linked polymorphic markers) can be targeted for diagnostic purposes once an association has been drawn between a particular disease or condition and a corresponding human haplotype. Thus, the determination of an individual's likelihood for developing a particular disease of condition can be made by characterizing one or more disease-associated polymorphic alleles (or even one or more disease-associated haplotypes) without necessarily determining or characterizing the causative genetic variation.

2. SUMMARY OF THE INVENTION

In one aspect, the present invention provides novel methods and kits for determining whether a subject has or is predisposed to developing a disease or condition that is associated with an IL-1 polymorphism. In one embodiment, the method comprises determining whether the subject's nucleic acids contain a marker or allele comprising an IL-1 inflammatory haplotype. In a preferred embodiment, the IL-1 inflammatory haplotype is indicative of increased I1-1 agonist (e.g. IL-1 (44112332)). In another preferred embodiment, the IL-1 inflammatory haplotype is indicative of decreased IL-1 receptor antagonist activity (e.g. IL-1 (33441461)).

An allele comprising an IL-1 inflammatory haplotype can be detected by any of a variety of available techniques, including: 1) performing a hybridization reaction between a nucleic acid sample and a probe that is capable of hybridizing to the allele; 2) sequencing at least a portion of the allele; or 3) determining the electrophoretic mobility of the allele or fragments thereof (e.g., fragments generated by endonuclease digestion). The allele can optionally be subjected to an amplification step prior to performance of the detection step. Preferred amplification methods are selected from the group consisting of: the polymerase chain reaction (PCR), the ligase chain reaction (LCR), strand displacement amplification (SDA), cloning, and variations of the above (e.g. RT-PCR and allele specific amplification). Oligonucleotides necessary for amplification may be selected, for example, from within the IL-1 gene loci, either flanking the marker of interest (as required for PCR amplification) or directly overlapping the marker (as in ASO hybridization). In a particularly preferred embodiment, the sample is hybridized with a set of primers, which hybridize 5' and 3' in a sense or antisense sequence to the vascular disease associated allele, and is subjected to a PCR amplification.

An allele comprising an IL-1 inflammatory haplotype may also be detected indirectly, e.g. by analyzing the protein product encoded by the DNA. For example, where the marker in question results in the translation of a mutant protein, the protein can be detected by any of a variety of protein detection methods. Such methods include immunodetection and biochemical tests, such as size fractionation, where the protein has a change in apparent molecular weight either through truncation, elongation, altered folding or altered post-translational modifications.

In another aspect, the invention features kits for performing the above-described assays. The kit can include a nucleic acid sample collection means and a means for determining whether a subject carries at least one allele comprising an IL-1 inflammnatory haplotype. The kit may also contain a control sample either positive or negative or a standard and/or an algorithmic device for assessing the results and additional reagents and components including: DNA amplification reagents, DNA polymerase, nucleic acid amplification reagents, restrictive enzymes, buffers, a nucleic acid sampling device, DNA purification device, deoxynucleotides, oligonucleotides (e.g. probes and primers) etc.

As described above, the control may be a positive or negative control. Further, the control sample may contain the positive (or negative) products of the allele detection technique employed. For example, where the allele detection technique is PCR amplification, followed by size fractionation, the control sample may comprise DNA fragments of the appropriate size. Likewise, where the allele detection technique involves detection of a mutated protein, the control sample may comprise al sample of mutated protein. However, it is preferred that the control sample comprises the material to be tested. For example, the controls may be a sample of genomic DNA or a cloned portion of the IL-1 gene cluster. Preferably, however, the control sample is a highly purified sample of genomic DNA where the sample to be tested is genomic DNA.

The oligonucleotides present in said kit may be used for amplification of the region of interest or for direct allele specific oligonucleotide (ASO) hybridization to the markers in question. Thus, the oligonucleotides may either Bank the marker of interest (as required for PCR amplification) or directly overlap the marker (as in ASO hybridization).

Information obtained using the assays and kits described herein (alone or in conjunction with information on another genetic defect or environmental factor, which contributes to the disease or condition that is associated with an IL-1 inflammatory haplotype) is useful for determining whether a non-symptomatic subject has or is likely to develop the particular disease or condition. In addition, the information can allow a more customized approach to preventing the onset or progression of the disease or condition. For example, this information can enable a clinician to more effectively prescribe a therapy that will address the molecular basis of the disease or condition.

In yet a further aspect, the invention features methods for treating or preventing the development of a disease or condition that is associated with an IL-1 inflammnatory haplotype in a subject by administering to the subject an appropriate therapeutic of the invention. In still another aspect, the invention provides in vitro or in vivo assays for screening test compounds to identify therapeutics for treating or preventing the development of a disease or condition that is associated with an IL-1 inflammatory haplotype. In one embodiment, the assay comprises contacting a cell transfected with a causative mutation that is operably linked to an appropriate promoter with a test compound and determining the level of expression of a protein in the cell in the presence and in the absence of the test compound. In a preferred embodiment, the causative mutation results in decreased production of IL-1 receptor antagonist, and increased production of the IL-1 receptor antagonist in the presence of the test compound indicates that the compound is an agonist of IL-1 receptor antagonist activity. In another preferred embodiment, the causative mutation results in increased production of IL-1α or IL-1β, and decreased production of IL-1α or IL-1β in the presence of the test compound indicates that the compound is an antagonist of IL-1α or IL-1β activity. In another embodiment, the invention features transgenic non-human animals and their use in identifying antagonists of IL-1α or IL-1β activity or agonists of IL-1Ra activity.

Other embodiments and advantages of the invention are set forth in the following detailed description and claims.

3. BRIEF DESCRIPTION OF THE FIGURES

FIG. 3 shows the nucleic acid sequence for IL-1A (GEN X03833; SEQ ID No. 1).

FIG. 4 shows the nucleic acid sequence for IL-1B (GEN X04500; SEQ ID No. 2).

FIG. 5 shows the nucleic acid sequence for the secreted IL-1RN (GEN X64532;

Figure 1:
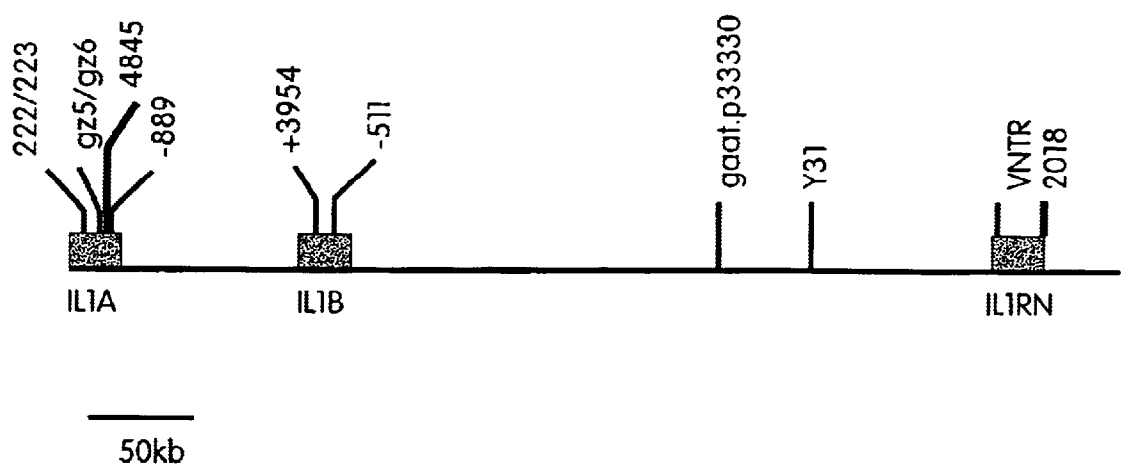
FIG. 1 is a schematic depiction of the IL-1 gene cluster including a few polymorphic markers.

SEQ ID No. 3).

4. DETAILED DESCRIPTION OF THE INVENTION

4.1 Definitions

For convenience, the meaning of certain terms and phrases employed in the specification, examples, and appended claims is provided below.

The term "allele" refers to the different sequence variants found at different polymorphic regions. For example, IL-1RN (VNTR) has at least five different alleles. The sequence variants may be single or multiple base changes, including without limitation insertions, deletions, or substitutions, or may be a variable number of sequence repeats.

The term "allelic pattern" refers to the identity of an allele or alleles at one or more polymorphic regions. For example, an allelic pattern may consist of a single allele at a polymorphic site, as for IL-1RN (VNTR) allele 1, which is an allelic pattern having at least one copy of IL-1RN allele 1 at the VNTR of the IL-1RN gene loci. Alternatively, an allelic pattern may consist of either a homozygous or heterozygous state at a single polymorphic site. For example, IL1-RN (VNTR) allele 2,2 is an allelic pattern in which there are two copies of the second allele at the VNTR marker of IL-1RN that corresponds to the homozygous IL-RN (VNTR) allele 2 state. Alternatively, an allelic pattern may consist of the identity of alleles at more than one polymorphic site.

The term "antibody" as used herein is intended to refer to a binding agent including a whole antibody or a binding fagment thereof which is specifically reactive with an IL-1 polypeptide. Antibodies can be fragmented using conventional techniques and the fragments screened for utility in the same manner as described above for whole antibodies. For example, F(ab)$_2$ fragments can be generated by treating an antibody with pepsin The resulting F(ab)$_2$ fragment can be treated to reduce disulfide bridges to produce Fab fragments. The antibody of the present invention is further intended to include bispecific, single-chain, and chimeric and humanized molecules having affinity for an IL-1B polypeptide conferred by at least one CDR region of the antibody.

"Biological activity" or "bioactivity" or "activity" or "biological function", which are used interchangeably, for the purposes herein means an effector or antigenic function that is directly or indirectly performed by an IL-1 polypeptide (whether in its native or denatured conformation), or by any subsequence thereof. Biological activities include binding to a target peptide, e.g., an IL-1 receptor. An IL-1 bioactivity can be modulated by directly affecting an IL-1 polypeptide. Alternatively, an IL-1 bioactivity can be modulated by modulating the level of an IL-1 polypeptide, such as by modulating expression of an IL-1 gene.

As used herein the term "bioactive fragment of an IL-1 polypeptide" refers to a fragment of a full-length IL-1 polypeptide, wherein the fragment specifically mimics or antagonizes the activity of a wild-type IL-1 polypeptide. The bioactive fragment preferably is a fragment capable of interacting with an interleukin receptor.

The term "an aberrant activity", as applied to an activity of a polypeptide such as IL-1, refers to an activity which differs from the activity of the wild-type or native polypeptide or which differs from the activity of the polypeptide in a healthy subject. An activity of a polypeptide can be aberrant because it is stronger than the activity of its native counterpart. Alternatively, an activity can be aberrant because it is weaker or absent relative to the activity of is its native counterpart. An aberrant activity can also be a change in an activity. For example an aberrant polypeptide can interact with a different target peptide. A cell can have an aberrant IL-1 activity due to overexpression or underexpression of an IL-1 locus gene encoding an IL-1 locus polypeptide.

"Cells", "host cells" or "recombinant host cells" are terms used interchangeably herein to refer not only to the particular subject cell, but to the progeny or potential progeny of such a cell. Because certain modifications may occur in succeeding generations due to either mutation or environmental influences, such progeny may not, in fact be identical to the parent cell, but are still included within the scope of the term as used herein.

A "chimera," "mosaic," "chimeric mammal" and the like, refers to a transgenic mammal with a knockout or knock-in construct in at least some of its genome-containing cells.

The terms "control" or "control sample" refer to any sample appropriate to the detection technique employed. The control sample may contain the products of the allele detection technique employed or the material to be tested. Further, the controls may be positive or negative controls. By way of example, where the allele detection technique is PCR amplification, followed by size fractionation, the control sample may comprise DNA fragments of an appropriate size. Likewise, where the allele detection technique involves detection of a mutated protein, the control sample may comprise a sample of a mutant protein. However, it is preferred that the control sample comprises the material to be tested. For example, the controls may be a sample of genomic DNA or a cloned portion of the IL-1 gene cluster. However, where the sample to be tested is genomic DNA, the control sample is preferably a highly purified sample of genomic DNA.

The phrase "diseases and conditions associated with IL-1 polymorphisms" refers to a variety of diseases or conditions, the susceptibility to which can be indicated in a subject based on the identification of one or more alleles within the IL-1 complex. Examples include: inflammatory or degenerative disease, including: Systemic Inflammatory Response (SIRS); Alzheimer's Disease (and associated conditions and symptoms including: chronic neuroinflammation, glial activation; increased microglia; neuritic plaque formation; and response to therapy); Amylotropic Lateral Sclerosis (ALS), arthritis (and associated conditions and symptoms including: acute joint inflammation, antigen-induced arthritis, neuritis associated with chronic lymphocytic thyroiditis, collagen-induced arthitis, juvenile chronic arthritis; juvenile rheumatoid arthritis, osteoarthritis, prognosis and streptococcus-induced arthritis), asthma (and associated conditions and symptoms, including: bronchial asthma; chronic obstructive airway disease; chronic obstructive pulmonary disease, juvenile asthma and occupational asthma); cardiovascular diseases (and associated conditions and symptoms, including atherosclerosis; autoimmune myocarditis, chronic cardiac hypoxia, congestive heart failure, coronary artery disease, cardiomyopathy and cardiac cell dysfunction, including: aortic smooth muscle cell activation; cardiac cell apoptosis; and immunomodulation of cardiac cell function; diabetes and associated conditions and symptoms, including autoimmune diabetes, insulin-dependent (Type 1) diabetes, diabetic periodontitis, diabetic retinopathy, and diabetic nephropathy); gastrointestinal inflammations (and related conditions and symptoms, including celiac disease, associated osteopenia, chronic colitis, Crohn's disease, inflammatory bowel disease and ulcerative colitis); gastric ulcers; hepatic inflammations, cholesterol gallstones and hepatic fibrosis, HIV infection (and associated conditions and symptoms, including degenerative responses, neurodegenerative responses, and HIV associated Hodgkin's Disease), Kawasaki's Syndrome (and associated diseases and conditions, including mucocutaneous lymph node syndrome, cervical lymphadenopathy, coronary artery lesions, edema, fever, increased leukocytes, mild anemia, skin peeling, rash, conjunctiva redness, thrombocytosis; multiple sclerosis, nephropathies (and associated diseases and conditions, including diabetic nephropathy, endstage renal disease, glomerulonephritis, Goodpasture's syndrome, hemodialysis survival and renal ischemic reperfusion injury), neurodegenerative diseases (and associated diseases and conditions, including acute neurodegeneration, induction of IL-1 in aging and neurodegenerative disease, IL-1 induced plasticity of hypothalamus neurons and chronic stress hyperresponsiveness), Ophthalmopathies (and associated diseases and conditions, including diabetic retinopathy, Graves' Ophthalmopathy, and uveitis, osteoporosis (and associated diseases and conditions, including alveolar, femoral, radial, vertebral or wrist bone loss or fracture incidence, postmenopausal bone loss, mass, fracture incidence or rate of bone loss), otitis media (adult or pediatric), pancreatis or pancreatic acinitis, periodontal disease (and associated diseases and conditions, including adult, early onset and diabetic); pulmonary diseases, including chronic lung disease, chronic sinusitis, hyaline membrane disease, hypoxia and pulmonary disease in SIDS; restenosis; rheumatism including rheumatoid arthritis, rheumatic aschoff bodies, rheumatic diseases and rheumatic myocarditis; thyroiditis including chronic lymphocytic thyroiditis;urinary tract infections including chronic prostatitis, chronic pelvic pain syndrome and urolithiasis. Immunological disorders, including autoimmune diseases, such as alopecia aerata, autoimmune myocarditis, Graves' disease, Graves ophthalmopathy, lichen sclerosis, multiple sclerosis, psoriasis, systemic lupus erythematosus, systemic sclerosis, thyroid diseases (e.g. goiter and stnuma lymphomatosa (Hashimoto's thyroiditis, lymphadenoid goiter), sleep in disorders and chronic fatigue syndrome and obesity (non-diabetic or associated with diabetes). Resistance to infectious diseases, such as Leishmaniasis, Leprosy, Lyme Disease, Lyme Carditis, malaria, cerebral malaria, meningititis, tubulointestitial nephritis associated with malaria), which are caused by bacteria, viruses (e.g. cytomegalovirus, encephalitis, Epstein-Barr Virus, Human Immunodeficiency Virus, Influenza Virus) or protozoans (e.g., Plasmodium falciparum, trypanosomes). Response to trauma, including cerebral trauma (including strokes and ischemias, encephalitis, encephalopathies, epilepsy, perinatal brain injury, prolonged febrile seizures, SIDS and subarachnoid hemorrhage), low birth weight (e.g. cerebral palsy), lung injury (acute hemorrhagic lung injury, Goodpastue's syndrome, acute ischemic reperfiusion), myocardial dysfunction, caused by occupational and environmental pollutants (e.g. susceptibility to toxic oil syndrome silicosis), radiation trauma, and efficiency of wound healing responses (e.g. burn or thermal wounds, chronic wounds, surgical.:wounds and spinal cord injuries). Susceptibility to neoplasias, including breast cancer associated osteolytic metastasis, cachexia, colorectal cancer, hyperproliferative diseases, Hodgkin's disease, leukemias, lymphomas, metabolic diseases and tumors, metastases, myelomas, and various cancers (including breast prostate ovarian, colon, lung, etc), anorexia and cachexia. Hormonal regulation including fertility/fecundity, likelihood of a pregnancy, incidence of preterm labor, prenatal and neonatal complications including preterm low birth weight, cerebral palsy, septicemia, hypothyroxinernia, oxygen dependence, cranial abnormality, early onset menopause. A subject's response to transplant (rejection or acceptance), acute phase response (e.g. febrile response), general inflammatory response, acute respiratory distress response, acute systemic inflammatory response, wound healing, adhesion, immunoinflammatory response, neuroendocrine response, fever development and resistance, acute-phase response, stress response, disease susceptibility, repetitive motion stress, tennis elbow, and pain management and response.

The phrases "disruption of the gene" and "targeted disruption" or any similar phrase refers to the site specific interruption of a native DNA sequence so as to prevent expression of that gene in the cell as compared to the wild-type copy of the gene. The interruption may be caused by deletions, insertions or modifications to the gene, or any combination thereof.

The term "haplotype" as used herein is intended to refer to a set of alleles that are inherited together as a group (are in linkage disequilibrium) at statistically significant levels ($P_{corr}$ <0.05). As used herein, the phrase "an IL-1 haplotype" refers to a haplotype in the IL-1 loci. An IL-1 inflammatory or proinflammatory haplotype refers to a haplotype that is indicative of increased agonist and/or decreased antagonist activities.

The terms "IL-1 gene cluster" and "IL-1 loci" as used herein include all the nucleic acid at or near the 2q13 region of chromosome 2, including at least the IL-1A, IL-1B and IL-1RN genes and any other linked sequences. (Nicklin et al., *Genomics* 19: 382–84, 1994). The terms "IL-1A", "IL-1B", and "IL-1RN" as used herein refer to the genes coding for IL-1, IL-1, and IL-1 receptor antagonist, respectively. The gene accession number for IL-1A, IL-1B, and IL-1RN are X03833, X04500, and X64532, respectively.

"IL-1 functional mutation" refers to a mutation within the IL-1 gene cluster that results in an altered phenotype (i.e. effects the function of an IL-1 gene or protein). Examples include: IL-1A(+4845) allele 2, IL-1B (+3954) allele 2, IL-1B (+6912) allele 2 and IL-1RN (+2018) allele 2.

"IL-1X (Z) allele Y" refers to a particular allelic form, designated Y, occurring at an IL-1 locus polymorphic site in gene X, wherein X is IL-1A, B, or RN and positioned at or near nucleotide Z, wherein nucleotide Z is numbered relative to the major transcriptional start site, which is nucleotide +1, of the particular IL-1 gene X As further used herein, the term "IL-1X allele (Z)" refers to all alleles of an IL-1 polymorphic site in gene X positioned at or near nucleotide Z. For example, the term "IL-1 IRN (+2018) allele" refers to alternative forms of the IL-1RN gene at marker +2018. "IL-1RN (+2018) allele 1" refers to a form of the IL-1RN gene which contains a cytosine (C) at position +2018 of the sense strand. Clay et al., *Hum. Genet.* 97:723–26, 1996. "IL-1RN (+2018) allele 2" refers to a form of the IL-1RN gene which contains a thymine (T) at position +2018 of the plus strand. When a subject has two identical IL-1RN alleles, the subject is said to be homozygous, or to have the homozygous state. When a subject has two different IL-1RN alleles, the subject is said to be heterozygous, or to have the heterozygous state. The term "IL-1RN (+2018) allele 2,2" refers to the homozygous IL-1 RN (+2018) allele 2 state. Conversely, the term "IL-1RN (+2018) allele 1,1" refers to the homozygous IL-1 RN (+2018) allele 1 state. The term "IL-1RN (+2018) allele 1,2" refers to the heterozygous allele 1 and 2 state.

"IL-1 related" as used herein is meant to include all genes related to the human IL-1 locus genes on human chromosome 2 (2q 12–14). These include IL-1 genes of the human IL-1 gene cluster located at chromosome 2 (2q 13–14) which include: the IL-1A gene which encodes interleukin-1α, the IL-1B gene which encodes interleukin-1β, and the IL-1RN (or IL-1ra) gene which encodes the interleukin-1 receptor antagonist. Furthermore these IL-1 related genes include the type I and type II human IL-1 receptor genes located on human chromosome 2 (2q12) and their mouse homologs located on mouse chromosome 1 at position 19.5 cM. Interleukin-1α, interleukin-1β, and interleukin-1RN are related in so much as they all bind to IL-1 type I receptors, however only interleukin-1α and interleukin-1β are agonist ligands which activate IL-1 type I receptors, while interleukin-1RN is a naturally occurring antagonist ligand. Where the term "IL-1" is used in reference to a gene product or polypeptide, it is meant to refer to all gene products encoded by the interleukin-1 locus on human chromosome 2 (2q 12–14) and their corresponding homologs from other species or functional variants thereof. The term IL-1 thus includes secreted polypeptides which promote an inflammatory response, such as IL-1α and IL-1β, as well as a secreted polypeptide which antagonize inflammatory responses, such as IL-1 receptor antagonist and the IL-1 type II (decoy) receptor.

An "IL-1 receptor" or "IL-1R" refers to various cell membrane bound protein receptors capable of binding to and/or transducing a signal from an IL-1 locus-encoded ligand. The term applies to any of the proteins which are capable of binding interleukin-1 (IL-1) molecules and, in their native configuration as mammalian plasma membrane proteins, presumably play a role in transducing the signal provided by IL-1 to a cell. As used herein, the term includes analogs of native proteins with IL-1-binding or signal transducing activity. Examples include the human and murine IL-1 receptors described in U.S. Pat. No. 4,968,607. The term "IL-1 nucleic acid" refers to a nucleic acid encoding an IL-1 protein.

Figure 2:
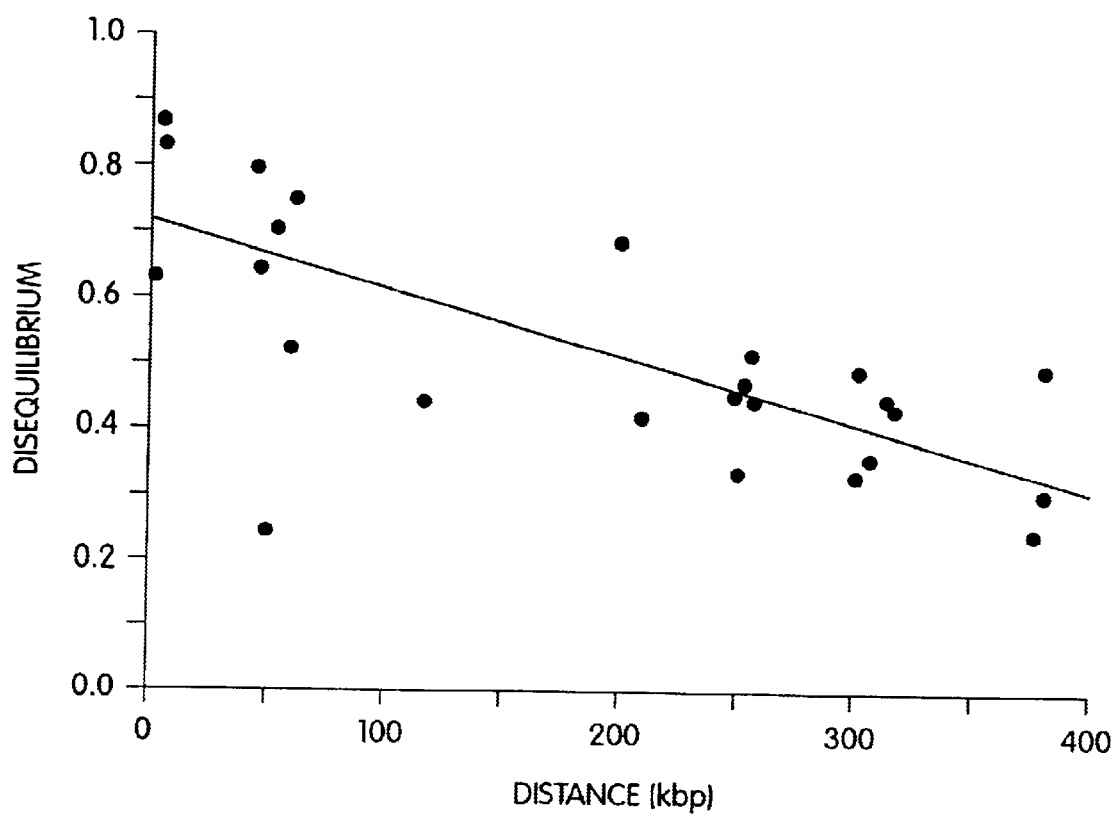
FIG. 2 is a graph which plots the correlation between disequilibrium values and physical distance as described herein.

An "IL-1 polypeptide" and "IL-1 protein" are intended to encompass polypeptides comprising the amino acid sequence encoded by the IL-1 genomic DNA sequences shown in FIGS. 1, 2, and 3, or fragments thereof, and homologs thereof and include agonist and antagonist polypeptides.

"Increased risk" refers to a statistically higher frequency of occurrence of the disease or condition in an individual carrying a particular polymorphic allele in comparison to the frequency of occurrence of the disease or condition in a member of a population that does not carry the particular polymorphic allele.

The term "interact" as used herein is meant to include detectable relationships or associations (e.g. biochemical interactions) between molecules, such as interactions between protein-protein, protein-nucleic acid, nucleic acid-nucleic acid and protein-small molecule or nucleic acid-small molecule in nature.

The term "isolated" as used herein with respect to nuclei c acids, such as DNA or RNA,refers to molecules separated from other DNAs, or RNAs, respectively, tatare present in the natural source of the macromolecule. For example, an isolated nucleic acid encoding one of the subject IL-1 polypeptides preferably includes no more than 10 kilobases (kb) of nucleic acid sequence which naturally immnediately flanks the IL-1 gene in genomic DNA, more, preferably no more than 5 kb of such naturally occurring flanking sequences, and most preferably less than 1.5 kb of such naturally occurring flanking sequence. The term isolated as used herein also refers to a nucleic acid or peptide that is substantially free of cellular material, viral material or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state. The term "isolated" is also used herein to refer to polypeptides which are isolated from other cellular proteins and is meant to encompass both purified and recombinant polypeptides.

A "knock-in" transgenic animal refers to an animal that has had a modified gene introduced into its genome and the modified gene can be of exogenous or endogenous origin.

A "knock-out" transgenic animal refers to an animal in which there is partial or complete suppression of the expression of an endogenous gene (e.g., based on deletion of at least a portion of the gene, replacement of at least a portion of the gene with a second sequence, introduction of stop codons, the mutation of bases encoding critical amino acids, or the removal of an intron junction, etc.).

A "knock-out construct" refers to a nucleic acid sequence that can be used to decrease or suppress expression of a protein encoded by endogenous DNA sequences in a cell. In a simple example, the knockout construct is comprised of a gene, such as the IL-1RN gene, with a deletion in a critical portion of the gene, so that active protein cannot be expressed therefrom. Alternatively, a number of termination codons can be added to the native gene to cause early termination of the protein or an intron junction,can be inactivated. In a typical knock-out construct, some portion of the gene is replaced with a selectable marker (such as the neo gene) so that the gene can be represented as follows: IL-1RN 5'/neo/IL-1RN 3', where IL-1RN5' and IL-1RN 3', refer to genomic or cDNA sequences which are, respectively, upstream and downstream relative to a portion of the IL-1RN gene and where neo refers to a neomycin resistance gene. In another knock-out construct, a second selectable marker is added in a flanking position so that the gene can be represented as: IL-1RN/neo/IL-1RN/TK, where TK is a thyridine kinase gene which can be added to either the IL-1RN5' or the IL-1RN3' sequence of the preceding construct and which further can be selected against (i.e. is a negative selectable marker) in appropriate media This two-marker construct allows the selection of homologous recombiriation events, which removes the flanking TK marker, from non-homologous recombination events which typically retain the TK sequences. The gene deletion and/or replacement can be from the exons, introns, especially intron junctions, and/or the regulatory regions such as promoters.

"Linkage disequilibrium" refers to co-inheritance of two alleles at frequencies greater than would be expected from the separate frequencies of occurrence of each allele in a given control population. The expected frequency of occurrence of two alleles that are inherited independently is the frequency of the first allele multiplied by the frequency of the second allele. Alleles that co-occur at expected frequencies are said to be in "linkage disequilibrium". The cause of linkage disequilibrium is often unclear. It can be due to selection for certain allele combinations or to recent admixture of genetically heterogeneous populations. In addition, in the case of markers that are very tightly linked to a disease gene, an association of an allele (or group of linked alleles) with the disease gene is expected if the disease mutation occurred in the recent past, so that sufficient time has not elapsed for equilibrium to be achieved through recombination events in the specific chromosomal region. When referring to allelic patterns that are comprised of more than one allele, a first allelic pattern is in linkage disequilibrium with a second allelic pattern if all the alleles that comprise the first allelic pattern are in linkage disequilibrium with at least one of the alleles of the second allelic pattern. An example of linkage disequilibrium is that which occurs between the alleles at the IL-1RN (+2018) and IL-1RN (VNTR) polymorphic sites. The two alleles at IL-1RN (+2018) are 100% in linkage disequilibrium with the two most frequent alleles of IL-1RN (VNTR), which are allele 1 and allele 2.

The term "marker" refers to a sequence in the genome that is known to vary among individuals. For example, the IL-1RN gene has a marker that consists of a variable number of tandem repeats (VNTR).

A "mutated gene" or "mutation" or "functional mutation" refers to an allelic form of a gene, which is capable of altering the phenotype of a subject having the mutated gene relative to a subject which does not have the mutated gene. The altered phenotype caused by a mutation can be corrected or compensated for by certain agents. If a subject must be homozygous for this mutation to have an altered phenotype, the mutation is said to be recessive, If one copy of the mutated gene is sufficient to alter the phenotype of the subject, the mutation is said to be dominant. If a subject has one copy of the mutated gene and has a phenotype that is intermediate between that of a homozygous and that of a heterozygous subject (for that gene), the mutation is said to be co-dominant A "non-human animal" of the invention includes mammals such as rodents, non-human primates, sheep, dogs, cows, goats, etc. amphibians, such a s members of the Xenopus genus, and transgenic avians (e.g. chickens, birds, etc.). The term "chimeric animal" is used herein to refer to animals in which the recombinant gene is found, or in which the recombinant gene is expressed in some but not all cells of the animal. The term "tissue-specific chimeric animal" indicates that one of the recombinant IL-1 genes is present and/or expressed or disrupted in some tissues but not others. The term "non-human mammal" refers to any member of the class Mammalia, except for humans.

As used herein, the term "nucleic acid" refers to polynucleotides or oligonucleotides such as deoxyribonucleic acid (DNA), and, where appropriate, ribonucleic acid (RNA). The term should also be understood to include, as equivalents, analogs of either RNA or DNA made from nucleotide analogs (e.g. peptide nucleic acids) and as applicable to the embodiment being described, single (sense or antisense) and double-stranded polynucleotides.

The term "polymorphism" refers to the coexistence of more than one form of a gene or portion (e.g., allelic variant) thereof. A portion of a gene of which there are at least two different forms, i.e., two different nucleotide sequences, is referred to as a "polymnorphic region of a gene". A specific genetic sequence at a polymorphic region of a gene is an allele. A polymorphic region can be a single nucleotide, the identity of which differs in different alleles. A polymorphic region can also be several nucleotides long.

The term "propensity to disease," also "predisposition" or "susceptibility" to disease or any similar phrase, means that certain alleles are hereby discovered to be associated with or predictive of a subjert's incidence of developing a particular disease (e.g. a vascular disease). The alleles are thus over-represented in frequency in individuals with disease as compared to healthy individuals. Thus, these alleles can be used to predict disease even in pre-symptomatic or pre-diseased individuals.

"Small molecule" as used herein, is meant to refer to a composition, which has a molecular weight of less than about 5 kD and most preferably less than about 4 kD. Small molecules can be nucleic acids, peptides, peptidomimetics, carbohydrates, lipids or other organic to or inorganic molecules.

As used herein, the term "specifically hybridizes" or "specifically detects" refers to the ability of a nucleic acid molecule to hybridize to at least approximately 6 consecutive nucleotides of a sample nucleic acid.

"Transcriptional regulatory sequence" is a generic term used throughout the specification to refer to DNA sequences, such as initiation signals, enhancers, and promoters, which induce or control transcription of protein coding sequences with which they are operably linked.

As used herein, the term "transgene" means a nucleic acid sequence (encoding, e.g., one of the IL-1 polypeptides, or an antisense transcript thereto) which has been introduced into a cell. A transgene could be partly or entirely heterologous, i.e., foreign, to the transgenic animal or cell into which it is introduced, or, is homologous to an endogenous gene of the transgenic animal or cell into which it is introduced, but which is designed to be inserted, or is inserted, into the animal's genome in such a way as to alter the genome of the cell into which it is inserted, (e.g., it is inserted at a location which differs from that of the natural gene or its insertion results in a knockout). A transgene can also be present in a cell in the form of an episome. A transgene can include one or more transcriptional regulatory sequences and any other nucleic acid, such as introns, that may be necessary for optimal expression of a selected nucleic acid.

A "transgenic animal" refers to any animal, preferably a non-human mammal, bird or an amphibian, in which one or more of the cells of the animal contain heterologous nucleic acid introduced by way of human intervention, such as by transgenic techniques well known in the art. The nucleic acid is introduced into the cell, directly or indirectly by introduction into a precursor of the cell, by way of deliberate genetic manipulation; such as by microinjection or by infection with a recombinant virus. The term genetic manipulation does not include classical cross-breeding, or in vitro fertilization, but rather is directed to the introduction of a recombinant DNA molecule. This molecule may be integrated within a chromosome, or it may be extrachromosomally replicating DNA. In the typical transgenic animals described herein, the transgene causes cells to express a recombinant form of one of an IL-1 polypeptide, e.g. either agonistic or antagonistic forms. However, transgenic animals in which the recombinant gene is silent are also contemplated, as for example, the FLP or CRE recombinase dependent constructs described below. Moreover, "transgenic animal" also includes those recombinant animals in which gene disruption of one or more genes is caused by human intervention, including both recombination and antisense techniques. The term is intended to include all progeny generations. Thus, the founder animal and all F1, F2, F3, and so on, progeny thereof are included.

The term "treating" as used herein is intended to encompass curing as well as ameliorating at least one symptom of a condition or disease.

The term "vector" refers to a nucleic acid molecule, which is capable of transporting another nucleic acid to which it has been linked. One type of preferred vector is an episome, i.e., a nucleic acid capable of extra-chromosomal replication. Preferred vectors are those capable of autonomous replication and/or expression of nucleic acids to which they are linked. Vectors capable of directing the expression of genes to which they are operatively linked are referred to herein as "expression vectors". In general, expression vectors of utility in recombinant DNA techniques are often in the form of "plasmids" which refer generally to circular double stranded DNA loops which, in their vector form are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

The term "wild-type allele" refers to an allele of a gene which, when present in two copies in a subject results in a wild-type phenotype. There can be several different wild-type alleles of a specific gene, since certain nucleotide changes in a gene may not affect the phenotype of a subject having two copies of the gene with the nucleotide changes.

4.2 Predictive Medicine 4.2.1. IL-1 Inflammatory Haplotypes and Their Association with Certain Diseases or Conditions.

The present invention is based at least in part, on the identification of certain inflammatory haplotype patterns and the association (to a statistically significant extent) of these patterns with the development of certain diseases or conditions. Therefore, detection of the alleles comprising a haplotype, alone or in conjunction with another means in a subject can indicate that the subject has or is predisposed to the development of a particular disease or condition. However, because these alleles art in linkage disequilibrium with other alleles, the detection of such other linked alleles can also indicate that the subject has or is predisposed to the development of a particular disease or condition. For example, the 44112332 haplotype comprises the following genotype:

allele 4 of the 222/223 marker of IL-1A
allele 4 of the gz5/gz6 marker of IL-1A
allele 1 of the −889 marker of IL-1A
allele 1 of the +3954 marker of IL-1B
allele 2 of the −511 marker of IL-1B
allele 3 of the gaat.p33330 marker
allele 3 of the Y31 marker
allele 2 of +2018 of IL-1RN
allele 1 of +4845 of IL-1A
allele 2 of the VNTR marker of IL-1RN Three other polymorphisms in an IL-1RN alternative exon (Exon lic, which produces an intracellular form of the gene product) are also in linkage disequilibrium with allele 2 of IL-1RN (VNTR) (Clay et al., (1996) Hum Genet 97:723–26). These include: IL-1RN exon lic (I812) (GenBank:X77090 at 1812); the IL-1RN exon lic (1868) polymorphism (GenBank:X77090 at 1868); and the IL-1RN exon lic (1887) polymorphism (GenBank:X77090 at 1887). Furthermore yet another polymorphism in the promoter for the alternatively spliced intracellular form of the gene, the Pic (I731) polymorphism (GenBank:X77090 at 1731), is also in linkage disequilibrium with allele 2 of the IL-1RN (VNTR) polymorphic locus. For each of these polymorphic loci, the allele 2 sequence variant has been determined to be in linkage disequilibrium with allele 2 of the IL-1RN (VNTR) locus (Clay et al., (1996) Hum Genet 97:723–26).

The 33221461 haplotype comprises the following genotype:

allele 3 of the 222/223 marker of IL-1A
allele 3 of the gz5/gz6 marker of IL-1A
allele 2 of the −889 marker of IL-1A
allele 2 of the +3954 marker of IL-1B
allele 1 of the −511 marker of IL-1B
allele 4 of the gaat.p33330 marker
allele 6 of the Y31 marker
allele 1 of +2018 of IL-1RN
allele 2 of +4845 of IL-1A
allele 1 of the VNTR marker of IL-1RN Individuals with the 44112332 haplotype are typically overproducers of both IL-1α and IL-1β proteins, upon stimulation. In contrast, individuals with the 33221461 haplotype are typically underproducers of IL-1ra. Each haplotype results in a net proinflammatory response. Each allele within a haplotype may have an effect, as well as a composite genotype effect. In addition, particular diseases may be associated with both haplotype patterns.

The following Table 1 sets forth a number of genotype markers and various diseases and conditions to which these markers have been found to be associated to a statistically significant extent.

TABLE 1

Association Of IL-1 Haplotype Gene Markers With Certain Diseases

| GENOTYPE | IL-1A (−889) | IL-1A (+4845) | IL-1B (−511) | IL-1B (+3954) | IL-1RN (+2018) |
|---|---|---|---|---|---|
| DISEASE | | | | | |
| Periodontal Disease | (*2) | *2 | | *2 | |
| Coronary Artery Disease | | | *2 | | *2 |
| Atherosclerosis | | | | | |
| Osteoporosis | | | | | *2 |
| Insulin dependent diabetes | | | | *2 | |
| Diabetic retinopathy | | | | | *1 |
| Endstage renal diseases | | | | | (+) |
| Diabetic nephropathy | | | | | *2 |
| Hepatic fibrosis (Japanese alcoholics) | | | | | (+) |
| Alopecia areata | | | | | *2 |
| Graves' disease | | | | | *2 |
| Graves' ophthalmopathy | | | | | (−) |
| Extrathyroid disease | | | | | (+) |
| Systemic Lupus Erythematosus | | | | | *2 |
| Licben Sclerosis | | | | | *2 |
| Arthritis | | | | | (+) |
| Juvenile chronic arthritis | *2 | | | | |
| Rheumatoid arthritis | | | | | (+) |
| Insulin dependent diabetes | | | | *2 | *2 |
| Ulcerative colitis | | | | | VNTR *2 |
| Asthma | | | *2 | *2 | |
| Multiple sclerosis | | | | (*2) | *2 VNTR |
| Menopause, early onset | | | | | *2 |

In addition to the allelic patterns described above, as described herein, one of skill in the art can readily identify other alleles (including polymorphisms and mutations) that are in linkage disequilibrium with an allele associated with a disease or disorder. For example, a nucleic acid sample from a first group of subjects without a particular disorder can be collected, as well as DNA from a second group of subjects with the disorder. The nucleic acid sample can then be compared to identify those alleles that are over-represented in the second group as compared with the first group, wherein such alleles are presumably associated with a disorder, which is caused or contributed to by inappropriate interleukin 1 regulation Alternatively, alleles that are in linkage disequilibrium with an allele that is associated with the disorder can be identified, for example, by genotyping a large population and performing statistical analysis to determine which alleles appear more commonly together than expected. Preferably the group is chosen to be comprised of genetically related individuals. Genetically related individuals include individuals from the same race, the same ethnic group, or even the same family. As the degree of genetic relatedness between a control group and a test group increases, so does the predictive value of polymorphic alleles which are ever more distantly linked to a disease-causing allele. This is because less evolutionary time has passed to allow polymorphisms which are linked along a chromosome in a founder population to redistribute through genetic cross-over events. Thus race-specific, ethnic-specific, and even family-specific diagnostic genotyping assays can be developed to allow for the detection of disease alleles which arose at ever more recent times in human evolution, e.g., after divergence of the major human races, after the separation of human populations into distinct ethnic groups, and even within the recent history of a particular family line.

Linkage disequilibrium between two polymorphic markers or between one polymorphic marker and a disease-causing mutation is a meta-stable state. Absent selective pressure or the sporadic linked reoccurrence of the underlying mutational events, the polymorphisms will eventually become disassociated by chromosomal recombination events and will thereby reach linkage equilibrium through the course of human evolution. Thus, the likelihood of finding a polymorphic allele in linkage disequilibrium with a disease or condition may increase with changes in at least two factors: decreasing physical distance between the polymorphic marker and the disease-causing mutation, and decreasing number of meiotic generations available for the dissociation of the linked pair. Consideration of the latter factor suggests that, the more closely related two individuals are, the more likely they will share a common parental chromosome or chromosomal region containing the linked polymorphisms and the less likely that this linked pair will have become unlinked through meiotic cross-over events occurring each generation. As a result, the more closely related two individuals are, the more likely it is that widely spaced polymorphisms may be co-inheritec Thus, for individuals related by common race, ethnicity or family, the reliability of ever more distantly spaced polymorphic loci can be relied upon as an indicator of inheritance of a linked disease-causing mutation.

Appropriate probes may be designed to hybridize to a specific gene of the IL-1 locus, such as IL-1A, IL-1B or IL-1RN or arelated gene. These genoric DNA sequences are shown in FIGS. 3, 4 and 5, respectively, and further correspond to SEQ ID Nos. 1, 2 and 3, respectively. Alternatively, these probes may incorporate other regions of the relevant genomic locus, including intergenic sequences. Indeed the IL-1 region of human chromosome 2 spans some 400,000 base pairs and, assuming an average of one single nucleotide polymorphism every 1,000 base pairs, includes some 400 SNPs loci alone. Yet other polymorphisms available for use with the immediate invention are obtainable from various public sources. For example, the human genome database collects intragenic SNPs, is searchable by sequence and currently contains approximately 2,700 entries (http://hgbase.interactiva.de). Also available is a human polymorphism database maintained by the Massachusetts Institute of Technology (MIT SNP database (http://www.genome.wi.mit.edu/SNP/human/index.html)). From such sources SNPs as well as other human polymorphisms may be found.

For example, examination of the IL-1 region of the human genome in any one of these databases reveals that the IL-1 locus genes are flanked by a centromere proximal polymorphic marker designated nicrosatellite marker AFM220ze3 at 127.4 cM (centiMorgans) (see GenBank Acc. No. Z17008) and a distal polymorphic marker designated microsatellite anchor marker AFM087xal at 127.9 cM. (see GenBank Acc. No. Z16545). These human polymorphic loci are both CA dinucleotide repeat microsatellite polymorphisms, and, as such, show a high degree of heterozygosity inhuman populations. For example, one allele of AFM220ze3 generates a 211 bp PCR amplification product with a 5' primer of the sequence TGTACCTAAGCCCACCCTTTAGAGC (SEQ ID No.4) and a 3' primer of the sequence TGGCCTCCAGAAACCTCCAA (SEQ ID No. 5). Furthermore, one allele of AFM087xal generates a 177 bp PCR amplification product with a 5' primer of the sequence GCTGATATTCTGGTGGGAAA (SEQ ID No. 6) and a 3' primer of the sequence GGCAAGAGCAAAACTCTGTC (SEQ ID No. 7). Equivalent primers corresponding to unique sequences occurring 5' and 3' to these human chromosome 2 CA dinucleotide repeat polymorphisms will-be apparent to one of sill in the art. Reasonable equivalent primers include those which hybridize within about 1 kb of the designated primer, and which further are anywhere from about 17 bp to about 27 bp in length. A general guideline for designing primers for amplification of unique human chromosomal genomic sequences is that they possess a melting temperature of at least about 50° C., wherein an approximate melting temperature can be estimated using the formula $T_{melt}=[2 \times (\# \text{ of A or T}) + 4 \times (\# \text{ of G or C})]$.

A number of other human polymorphic loci occur between these two CA dinucleotide repeat polymorphisms and provide additional targets for determination of a prognostic allele in a family or other group of genetically related individuals. For example, the National Center for Biotechnology Information web site (www.ncbi.nlm.nih.gov/genemap/) lists a number of polymorphism markers in the region of the IL-1 locus and provides guidance in designing appropriate primers for amplification and analysis of these markers.

Accordingly, the nucleotide segments of the invention may be used for their ability to selectively form duplex molecules with complementary stretches of human chromosome 2 q 12–13 or cDNAs from that region or to provide primers for amplification of DNA or cDNA from this region. The design of appropriate probes for this purpose requires consideration of a number of factors. For example, fragments having a length of between 10, 15, or 18 nucleotides to about 20, or to about 30 nucleotides, will find particular utility. Longer sequences, e.g., 40, 50, 80, 90, 100, even up to full length, are even more preferred for certain embodiments. Lengths of oligonucleotides of at least about 18 to 20 nucleotides are well accepted by those of skill in the art as sufficient to allow sufficiently specific hybridization so as to be useful as a molecular probe. Furthermore, depending on the application envisioned, one will desire to employ varying conditions of hybridization to achieve varying degrees of selectivity of probe towards target sequence. For applications requiring high selectivity, one will typically desire to employ relatively stringent conditions to form the hybrids. For example, relatively low salt and/or high temperature conditions, such as provided by 0.02 M–0.15M NaCl at temperatures of about 50° C. to about 70° C. Such selective conditions may tolerate little, if any, mismatch between the probe and the template or target strand.

Other alleles or other indicia of a disorder can be detected or monitored in a subject in conjunction with detection of the alleles described above, for example, identifying vessel wall thickness (e.g. as measured by ultrasound), or whether the subject smokes, drinks is overweight, is under stress or exercises.

4.2.2 Detection of Alleles

Many methods are available for detecting specific alleles at human polymorphic loci. The preferred method for detecting a specific polymorphic allele will depend, in part, upon the molecular nature of the polymorphism. For example, the various allelic forms of the polymorphic locus may differ by a single base-pair of the DNA. Such single nucleotide polymorphisms (or SNPs) are major contributors to genetic variation, comprising some 80% of all known polymorphisms, and their density in the human genome is estimated to be on average 1 per 1,000 base pairs. SNPs are most frequently biallelic-occurring in only two different forms (although up to four different forms of an SNP, corresponding to the four different nucleotide bases occurring in DNA, are theoretically possible). Nevertheless, SNPs are mutationally more stable than other polymorphisms, making them suitable for association studies in which linkage disequilibriumn between markers and an unknown variant is used to map disease-causing mutations. In addition, because SNPs typically have only two alleles, they can be genotyped by a simple plus/minus assay rather than a length measurement, making them more amenable to automation.

A variety of methods are available for detecting the presence of a particular single nucleotide polymorphic allele in an individual. Advancements in this field have provided accurate, easy, and inexpensive large-scale SNP genotyping. Most recently, for example, several new techniques have been described including dynamic allele-specific hybridization (DASH), microplate array diagonal gel electrophoresis (MADGE), pyrosequencing, oligonucleotide-specific ligation, the TaqMan system as well as various DNA "chip" technologies such as the Afymetrix SNP chips. These methods require amplification of the target genetic region, typically by PCR. Still other newly developed methods, based on the generation of small signal molecules by invasive cleavage followed by mass spectrometry or immobilized padlock probes and rolling-circle amplification, might eventually eliminate the need for PCR. Several of the methods known in the art for detecting specific single nucleotide polyrnorphisms are summarized below. The method of the present invention is understood to include all available methods.

Several methods have been developed to facilitate analysis of single nucleotide polymorphisms. In one embodiment, the single base polymorphism can be detected by using a specialized exonuclease-resistant nucleotide, as disclosed, e.g., in Mundy, C. R. (U.S. Pat. No.4,656,127). According to the method, a primer complementary to the allelic sequence immediately 3' to the polymorphic site is permitted to hybridize to a target molecule obtained from a particular animal or human. If the polymorphic site on the target molecule contains a nucleotide that is complementary to the particular exonuclease-resistant nucleotide derivative present, then that derivative will be incorporated onto the end of the hybridized primer. Such incorporation renders the primer resistant to exonuclease, and thereby permits its detection. Since the identity of the exonuclease-resistant derivative of the sample is known, a finding that the primer has become resistant to exonuclease reveals that the nucleotide present in the polymorphic site of the target molecule was complementary to that of the nucleotide derivative used in the reaction. This method has the advantage that it does not require the determination of large amounts of extraneous sequence data In another embodiment of the invention, a solution-based method is used for determining the identity of the nucleotide of a polymorphic site. Cohen, D. et al. (French Patent 2,650,840; PCT Appln. No. WO91/02087). As in the Mundy method of U.S. Pat. No. 4,656,127, a primer is employed that is complementary to allelic sequences immediately 3' to a polymorphic site. The method determines the identity of the nucleotide of that site using labeled dideoxynucleotide derivatives, which, if complementary to the nucleotide of the polymorphic site will become incorporated onto the terminus of the primer.

An alternative method, known as Genetic Bit Analysis or GBA™ is described by Goelet, P. et al. (PCT Appln. No. 92/15712). The method of Goelet, P. et al. uses mixtures of labeled terminators and a primer that is complementary to the sequence 3' to a polymorphic site. The labeled terminator that is incorporated is thus determined by, and complementary to, the nucleotide present in the polymorphic site of the target molecule being evaluated. In contrast to the method of Cohen et al. (French Patent 2,650,840; PCT Appln. No. WO91/02087) the method of Goelet, P. et al. is preferably a heterogeneous phase assay, in which the primer or the target molecule is immobilized to a solid phase.

Recently, several primer-guided nucleotide incorporation procedures for assaying polymorphic sites in DNA have been described (Komher, J. S. et al., Nucl. Acids. Res. 17:7779–7784 (1989); Sokolov, B. P., Nucl. Acids Res. 18:3671 (1990); Syvanen, A-C., et al., Genomics 8:684–692 (1990); Kuppuswamy, M. N. et al., Proc. Natl. Acad. Sci. (U.S.A.) 88:1 143–1147 (1991); Prezant, T. R. et al., Hum. Mutat. 1:159–164 (1992); Ugozzoli, L. et al., GATA 9:107–112 (1992); Nyren, P. et al., Anal. Biochem. 208 171–175 (1993)). These methods differ from GBA™ in that they all rely on the incorporation of labeled deoxynucleotides to discriminate between bases at a polymorphic site. In such a format, since the signal is proportional to the number of deoxynucleotides incorporated polymorphisms that occur in runs of the same nucleotide can result in signals that are proportional to the length of the run (Syvanen, A. -C., et al., Amer. J. Hum. Genet. 52:4659 (1993)).

For mutations that produce premature termination of protein translation, the protein truncation test (PTT) offers an efficient diagnostic approach (Roest, et. al., (1993) *Hum. Mol. Genet.* 2:1719–21; van der Luijt et. al., (1994) *Genomics* 20:14). For PIT, RNA is initially isolated from available tissue and reverse-transcribed, and the segment of interest is amplified by PCR. The products of reverse ranscription PCR are then used as a template for nested PCR amplification with a primer that contains an RNA polymerase promoter and a sequence for initiating eukaryotic translation. After amplification of the region of interest, the unique motifs incorporated into the primer permit sequential in vitro transcription and translation of the PCR products. Upon sodium dodecyl sulfate-polyacrylamide gel electrophoresis of translation products, the appearance of truncated polypeptides signals the presence of a mutation that causes premature termination of translation In a variation of this technique, DNA (as opposed to RNA) is used as a PCR template when the target region of interest is derived from a single exon.

Any cell type or tissue may be utilized to obtain nucleic acid samples for use in the diagnostics described herein. In a preferred embodiment, the DNA sample is obtained from a bodily fluid, e.g., blood, obtained by known techniques (e.g. venipuncture) or saliva. Alternatively, nucleic acid tests can be performed on dry samples (e.g. hair or skin). When using RNA or protein, the cells or tissues that may be utilized must express an IL-1 gene.

Diagnostic procedures may also be performed in situ directly upon tissue sections (fixed and/or frozen) of patient tissue obtained from biopsies or resections, such that no nucleic acid purification is necessary. Nucleic acid reagents may be used as probes and/or primers for such in situ procedures (see, for example, Nuovo, G. J., 1992, PCR in situ hybridization: protocols and applications, Raven Press, NY).

In addition to methods which focus primarily on the detection of one nucleic acid sequence, profiles may also be assessed in such detection schemes. Fingerprint profiles may be generated, for example, by utilizing a differential display procedure, Northern analysis and/or RT-PCR.

A preferred detection method is allele specific hybridization using probes overlapping a region of at least one allele of an IL-1 proinflammatory haplotype and having about 5, 10, 20, 25, or 30 nucleotides around the mutation or polymorphic region. In a preferred embodiment of the invention, several probes capable of hybridizing specifically to other allelic variants involved in a restenosis are attached to a solid phase support, e.g., a "chip" (which can hold up to about 250,000 oligonucleotides). Oligonucleotides can be bound to a solid support by a variety of processes, including lithography. Mutation detection analysis using these chips comprising oligonucleotides, also termed "DNA probe arrays" is described e.g., in Cronin et al. (1996) Human Mutation 7:244. In one embodiment, a chip comprises all the allelic variants of at least one polymorphic region of a gene. The solid phase support is then contacted with a test nucleic acid and hybridization to the specific probes is detected Accordingly, the identity of numerous allelic variants of one or more genes can be identified in a simple hybridization experiment.

These techniques may also comprise the step of amplifying the nucleic acid before analysis. Amplification techniques are known to those of skill in the art and include, but are not limited to cloning, polymerase chain reaction (PCR), polymerase chain reaction of specific alleles (ASA), ligase chain reaction (LCR), nested polymerase chain reaction, self sustained sequence replication (Guatelli, J. C. et al., 1990, Proc. Natl. Acad. Sci. USA 87:1874–1878), transcriptional amplification system, (Kwoh, D. Y. et al., 1989, Proc. Natl. Acad. Sci. USA 86:1173–1177), and Q- Beta Replicase (Lizardi, P. M. et al., 1988, Bio/Technology 6:1197).

Amplification products may be assayed in a variety of ways, including size analysis, restriction digestion followed by size analysis, detecting specific tagged oligonucleotide primers in the reaction products, allele-specific oligonucleotide (ASO) hybridization, allele specific 5' exonuclease detection, sequencing, hybridization, and the like.

PCR based detection means can include multiplex amplification of a plurality of markers simultaneously. For example, it is well known in the art to select PCR primers to generate PCR products that do not overlap in size and can be analyzed simultaneously. Alternatively, it is possible to amplify different markers with primers that are differentially labeled and thus can each be differentially detected. Of course, hybridization based detection means allow the differential detection of multiple PCR products in a sample. Other techniques are known in the art to allow multiplex analyses of a plurality of markers.

In a merely illustrative embodiment, the method includes the steps of (i) collecting a sample of cells from a patient, (ii) isolating nucleic acid (e.g., genomic, mRNA or both) from the cells of the sample, (iii) contacting the nucleic acid sample with one or more primers which specifically hybridize 5' and 3' to at least one allele of an IL-1 proinflammatory haplotype under conditions such that hybridization and amplification of the allele occurs, and (iv) detecting the amplification product. These detection schemes are especially useful for the detection of nucleic acid molecules if such molecules are present in very low numbers.

In a preferred embodiment of the subject assay, the allele of an IL-1 proinflammatory haplotype is identified by alterations in restriction enzyme cleavage patterns. For example, sample and control DNA is isolated, amplified (optionally), digested with one or more restriction endonucleases, and fragment length sizes are determined by gel electrophoresis.

In yet another embodiment, any of a variety of sequencing reactions known in the art can be used to directly sequence the allele. Exemplary sequencing reactions include those based on techniques developed by Maxim and Gilbert ((1977) Proc. Natl Acad Sci USA 74:560) or Sanger (Sanger et al (1977) Proc. Nat. Adad. Sci USA 74:5463). It is also contemplated that any of a variety of automated sequencing procedures may be utilized when performing the subject assays (see, for example Biotechniques (1995) 19:448), including sequencing by mass spectrometry (see, for example PCr publication WO 94/16101; Cohen et al. (1996) Adv Chromatogr 36:127–162; and Griffin et al. (1993) Appl Biochem Biotechnol 38:147–159). It will be evident to one of skill in the art that, for certain embodiments, the occurrence of only one, two or three of the nucleic acid bases need be determined in the sequencing reaction. For instance, A-track or the like, e.g., where only one nucleic acid is detected, can be carried out.

In a further embodiment, protection from cleavage agents (such as a nuclease, hydroxylanine or osmium tetroxide and with piperidine) can be used to detect mismatched bases in RNA/RNA or RNA/DNA or DNA/DNA heteroduplexes (Myers, et al. (1985) Science 230:1242). In general, the art technique of "mismatch cleavage" starts by providing heteroduplexes formed by hybridizing (labeled) RNA or DNA containing the wild-type allele with the sample. The double-stranded duplexes are treated with an agent which cleaves single-stranded regions of the duplex such as which will exist due to base pair mismatches between the control and sample strands. For instance, RNA/DNA duplexes can be treated with RNase and DNA/DNA hybrids treated with S1 nuclease to enzymatically digest the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al (1988) Proc. Natl Acad Sci USA 85:4397; and Saleeba et al (1992) Methods Enzymol. 217:286–295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes). For example, the mutY enzyme of E. coli cleaves A at G/A mismatches and the thymidine DNA glycosylase from HeLa cells cleaves T at G/T mismatches (Hsu et al. (1994) Carcinogenesis 15:1657–1662). According to an exemplary embodiment, a probe based on an allele of an IL-1 locus haplotype is hybridized to a cDNA or other DNA product from a test cell(s). The duplex is treated with a DNA mismatch repair enzyme, and the cleavage products, if any, can be detected from electrophoresis protocols or the like See, for example, U.S. Pat. No. 5,459,039.

In other embodiments, alterations in electrophoretic mobility will be used to identify an IL-1 locus allele. For example, single strand conformation polymorphism (SSCP) may be used to detect differences in electrophoretic mobility between mutant and wild type nucleic acids (Orita et al. (1989) Proc. Natl. Acad. Sci USA 86:2766, see also Cotton (1993) Mutat Res 285:125–144; and Hayashi (1992) Genet Anal Tech Appl 9:73–79). Single-stranded DNA fragments of sample and control IL-1 locus alleles are denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) Trends Genet 7:5).

In yet another embodiment, the movement of alleles in polyacrylamide gels containing a gradient of denaturant is assayed using denaturing gradient gel electrophoresis (DGGE) (Myers et al. (1985) Nature 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing agent gradient to identify differences in the mobility of control and sample DNA (Rosenbaum and Reissner (1987) Biophys Chem 265:12753).

Examples of other techniques for detecting alleles include, but are not limited to, selective oligonucleotide hybridization, selective amplification, or selective primer extension For example, oligonucleotide primers may be prepared in which the known mutation or nucleotide difference (e.g., in allelic variants) is placed centrally and then hybridized to target DNA under conditions which permit hybridization only if a perfect match is found (Saiki et al. (1986) Nature 324:163); Saiki et al (1989) Proc. Natl Acad. Sci USA 86:6230). Such allele specific oligonucleotide hybridization techniques may be used to test one mutation or polymorphic region per reaction when oligonucleotides are hybridized to PCR amplified target DNA or a number of different mutations or polymorphic regions when the oligonucleotides are attached to the hybridizing membrane and hybridized with labelled target DNA.

Alternatively, allele specific amplification technology which depends on selective PCR amplification may be used in conjunction with the instant invention. Oligonucleotides used as primers for specific amplification may carry the mutation or polymorphic region of interest in the center of the molecule (so that amplification depends on differential hybridization) (Gibbs et al (1989) Nucleic Acids Res. 17:2437–2448) or at the extreme 3' end of one primer where, under appropriate conditions, mismatch can prevent, or reduce polymerase extension (Prossner (1993) Tibtech 11:238. In addition it may be desirable to introduce a novel restriction site in the region of the mutation to create cleavage-based detection (Gasparini et al (1992) Mol. Cell Probes 6:1). It is anticipated that in certain embodiments amplification may also be performed using Taq ligase for amplification (Barany (1991) Proc. Natl. Acad. Sci USA 88:189). In such cases, ligation will occur only if there is a perfect match at the 3' end of the 5' sequence making it possible to detect the presence of a known mutation at a specific site by looking for the presence or absence of amplification.

In another embodiment, identification of the allelic variant is carried out using an oligonucleotide ligation assay (OLA), as described, e.g., in U.S. Pat. No. 4,998,617 and in Landegren, U. et al. ((1988) Science 241:1077–1080). The OLA protocol uses two oligonucleotides which are designed to be capable of hybridizing to abutting sequences of a single strand of a target. One of the oligonucleotides is linked to a separation marker, e.g.,. biotinylated, and the other is detectably labeled. If the precise complementary sequence is found in a target molecule, the oligonucleotides will hybridize such that their tennini abut, and create a ligation substrate. Ligation then permits the labeled oligonucleotide to be recovered using avidin, or another biotin ligand. Nickerson, D. A. et al. have described a nucleic acid detection assay that combines attributes of PCR and OLA (Nickerson, D. A. et al. (1990) Proc. Natl. Acad. Sci. USA 87:8923–27). In this method, PCR is used to achieve the exponential amplification of target DNA, which is then detected using OLA.

Several techniques based on this OLA method have been developed and can be used to detect alleles of an IL-1 locus haplotype. For example, U.S. Pat. No. 5,593,826 discloses an OLA using an oligonucleotide having 3'-amino group and a 5'-phosphorylated oligonucleotide to form a conjugate having a phosphoramidate linkage. In another variation of OLA described in Tobe et al. ((1996) Nucleic Acids Res 24: 3728), OLA combined with PCR permits typing of two alleles in a single microtiter well. By marking each of the allele-specific primers with a unique hapten, i.e. digoxigenin and fluorescein, each OLA reaction can be detected by using hapten specific antibodies that are labeled with different enzyme reporters, alkaline phosphatase or horseradish peroxidase. This system permits the detection of the two alleles using a high throughput format that leads to the production of two different colors.

Another embodiment of the invention is directed to kits for detecting a predisposition for developing a restenosis. This kit may contain one or more oligonucleotides, including 5' and 3' oligonucleotides that hybridize 5' and 3' to at least one allele of an IL-1 locus haplotype. PCR amplification oligonucleotides should hybridize between 25 and 2500 base pairs apart, preferably between about 100 and about 500 bases apart, in order to produce a PCR product of convenient size for subsequent analysis.

Particularly preferred primers for use in the diagnostic method of the invention include SEQ ID Nos. 8–32.

The design of additional oligonucleotides for use in the amplification and detection of IL-1 polymorphic alleles by the method of the invention is facilitated by the availability of both updated sequence information from human chromosome 2q13—which contains the human IL-1 locus, and updated human polymorphism information available for this locus. For example, the DNA sequence for the IL-1A, IL-1B and IL-1RN is shown in FIG. 1 (GenBank Accession No. X03833), 2 (GenBank Accession No. X04500) and 3 (GenBank Accession No. X64532) respectively. Suitable primers for the detection of a human polymorphism in these genes can be readily designed using this sequence information and standard techniques known in the art for the design and optimization of primers sequences. Optimal design of such primer sequences can be achieved, for example, by the use of commercially available primer selection programs such as Primer 2.1, Primer 3 or GeneFisher (See also, Nicklin M. H. J., Weith A. Duff G. W., "A Physical Map of the Region Encompassing the Human Interleukin-1α, interleukin-1β, and Interleukin-1 Receptor Antagonist Genes" Genomics 19: 382 (1995); Nothwang H. G., et al. "Molecular Cloning of the Interleukin-1 gene Cluster Construction of an Integrated YAC/PAC Contig and a partial transcriptional Map in the Region of Chromosome 2q13" Genomics:41: 370 (1997); Clark, et al. (1986) Nucl. Acids. Res., 14:7897–7914 [published erratum appears in Nucleic Acids Res., 15:868(1987) and the Genome Database (GDB) project at the URL http://www.gdb.org).

For use in a kit, oligonucleotides may be any of a variety of natural and/or synthetic compositions such as synthetic oligonucleotides, restriction fragments, cDNAs, synthetic peptide nucleic acids (PNAs), and the like. The assay kit and method may also employ labeled oligonucleotides to allow ease of identification in the assays. Examples of labels which may be employed include radio-labels, enzymes, fluorescent compounds, streptavidin, avidin, biotin, magnetic moieties, metal binding moieties, antigen or antibody moieties, and the like.

The kit may, optionally, also include DNA sampling means. DNA sampling means are well known to one of skill in the art and can include, but not be limited to substrates, such as filter papers, the AmpliCard™ (University of Sheffield, Sheffield, England S10 2JF; Tarlow, J W, et al., *J. of Invest. Dermatol.* 103:387–389 (1994)) and the like; DNA purification reagents such as Nucleon™ kits, lysis buffers, proteinase solutions and the like; PCR reagents, such as 10×reaction buffers, thermostable polymerase, dNTPs, and the like; and allele detection means such as the HinfI restriction enzyme, allele specific oligonucleotides, degenerate oligonucleotide primers for nested PCR from dried blood.

4.2.3. Pharmacogenomics

Knowledge of the particular alleles associated with a susceptibility to developing a particular disease or condition, alone or in conjunction with information on other genetic defects contributing to the particular disease or condition allows a customization of the prevention or treatment in accordance with the individual's genetic profile, the goal of "pharmacogenomics". Thus, comparison of an individual's IL-1 profile to the population profile for a vascular disorder, permits the selection or design of drugs or other therapeutic regimens that are expected to be safe and efficacious for a particular patient or patient population (i.e., a group of patients having the same genetic alteration).

In addition, the ability to target populations expected to show the highest clinical benefit, based on genetic,profile can enable: 1) the repositioning of already marketed drugs; 2) the rescue of drug candidates whose clinical development has been discontinued as a result of safety or efficacy limitations, which are patient subgroup-specific; and 3) an accelerated and less costly development for candidate therapeutics and more optimal drug labeling (e.g. since measuring the effect of various doses of an agent on the causative mutation is useful for optimizing effective dose).

The treatment of an individual with a particular therapeutic can be monitored by determining protein (e.g. IL-1α, IL-1β, or IL-1Ra), mRNA and/or transcriptional level. Depending on the level detected, the therapeutic regimen can then be maintained or adjusted (increased or decreased in dose). In a preferred embodiment, the effectiveness of treating a subject with an agent comprises the steps of: (i) obtaining a preadministration sample from a subject prior to administration of the agent; (ii) detecting the level or amount of a protein, mRNA or genomic DNA in the preadministration sample; (iii) obtaining one or more post-administration samples from the subject; (iv) detecting the level of expression or activity of the protein, mRNA or genomic DNA in the post-administration sample; (v) comparing the level of expression or activity of the protein, mRNA or genomic DNA in the preadministration sample with the corresponding protein, mRNA or genomic DNA in the postadministration sample, respectively; and (vi) altering the administration of the agent to the subject accordingly.

Cells of a subject may also be obtained before and after administration of a therapeutic to detect the level of expression of genes other than an IL-1 gene to verify that the therapeutic does not increase or decrease the expression of genes which could be deleterious. This can be done, e.g., by using the method of transcriptional profiling. Thus, mRNA from cells exposed in vivo to a therapeutic and mRNA from the same type of cells that were not exposed to the therapeutic could be reverse transcribed and hybridized to a chip containing DNA from numerous genes, to thereby compare the expression of genes in cells treated and not treated with the therapeutic.

4.3 Therapeutics for Diseases and Conditions Associated With IL-1 Polymorphisnis Therapeutic for diseases or conditions associated with an IL-1 polymorphism or haplotype refers to any agent or therapeutic regimen (including pharmaceuticals, nutraceuticals and surgical means) that prevents or postpones the development of or alleviates the symptoms of the particular disease or condition in the subject. The therapeutic can be a polypeptide, peptidomimetics, nucleic acid or other inorganic or organic molecule, preferably a "small molecule" including vitamins, minerals and other nutrients. Preferably the therapeutic can modulate at least one activity of an IL-1 polypeptide, e.g., interaction with a receptor, by mimicking or potentiating (agonizing) or inhibiting (antagonizing) the effects of a naturally-occurring polypeptide. An agonist can be a wild-type protein or derivative thereof having at least one bioactivity of the wild-type, e.g., receptor binding activity. An agonist can also be a compound that upregulates expression of a gene or which increases at least one bioactivity of a protein. An agonist can also be a compound which increases the interaction of a polypeptide with another molecule, e.g., a receptor. An antagonist can be a compound which inhibits or decreases the interaction between a protein and another molecule, e.g., a receptor or an agent that blocks signal transduction or post-translation processing (e.g., IL-1 converting enzyme (ICE) inhibitor). Accordingly, a preferred antagonist is a compound which inhibits or decreases binding to a receptor and thereby blocks subsequent activation of the receptor. An antagonist can also be a compound that downregulates expression of a gene or which reduces the amount of a protein present. The antagonist can be a dominant negative form of a polypeptide, e.g., a form of a polypeptide which is capable of interacting with a target peptide, e.g., a receptor, but which does not promote the activation of the receptor. The antagonist can also be a nucleic acid encoding a dominant negative form of a polypeptide, an antisense nucleic acid, or a ribozyme capable of interacting specifically with an RNA. Yet other antagonists are molecules which bind to a polypeptide and inhibit its action. Such molecules include peptides, e.g., forms of target peptides which do not have biological activity, and which inhibit binding to receptors. Thus, such peptides will bind to the active site of a protein and prevent it from interacting with target peptides. Yet other antagonists include antibodies that specifically interact with an epitope of a molecule, such that binding interferes with the biological function of the polypeptide. In yet another preferred embodiment, the antagonist is a small molecule, such as a molecule capable of inhibiting the interaction between a polypeptide and a target receptor. Alternatively, the small molecule can function as an antagonist by interacting with sites other than the receptor binding site.

Modulators of IL-1 (e.g. IL-1α, IL-1β or IL-1 receptor antagonist) or a protein encoded by a gene that is in linkage disequilibrium with an IL-1 gene can comprise any type of compound, including a protein, peptide, peptidomimetics, small molecule, or nucleic acid. Preferred agonists include nucleic acids (e.g. encoding an IL-1 protein or a gene that is up- or down-regulated by an IL-1 protein), protein's (e.g. IL-1 proteins or a protein that is up- or down-regulated thereby) or a small molecule (e.g. that regulates expression or binding of an IL-1 protein). Preferred antagonists, which can be identified, for example, using the assays described herein, include nucleic acids (e.g. single (antisense) or double stranded (triplex) DNA or PNA and ribozymes), protein (e.g. antibodies) and small molecules that act to suppress or inhibit IL-1 transcription and/or protein activity.

4.3.1. Effective Dose

Toxicity and therapeutic efficacy of such compounds can be determined by standard pharmaceutical procedures in cell cultures or experimental animals, e.g., for determining The $LD_{50}$ (the dose lethal to 50% of the population) and the $Ed_{50}$ (the dose therapeutically effective, in 50% of the population). The dose ratio between toxic and therapeutic effects is the therapeutic index and it can be expressed as the ratio $LD_{50}(ED_{50})$. Compounds which exhibit large therapeutic indices are preferred. While compounds that exhibit toxic side effects may be used, care should be taken to design a delivery system that targets such compounds to the site of affected tissues in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

4.3.2. Formulation and Use

Compositions for use in accordance with the present invention may be formulated in a conventional manner using one or more physiologically acceptable carriers or excipients. Thus, the compounds and their physiologicailly acceptable salts and solvates may be formulated for administration by, for example, injection, inhalation or insufflation (either through the mouth or the nose) or oral, buccal, parenteral or rectal administration.

For such therapy, the compounds of the invention can be formulated for a variety of loads of administration, including systemic and topical or localized administration. Techniques and formulations generally may be found in Rermmington's Pharmaceutical Sciences, Meade Publishing Co., Easton, Pa. For systemic administration, injection is preferred, including intramuscular, intravenous, intraperitoneal, and subcutaneous. For injection, the compounds of the invention can be formulated in liquid solutions, preferably in physiologically compatible buffers such as Hank's solution or Ringer's solution. In addition, the compounds may be formulated in solid form and redissolved or suspended immediately prior to use. Lyophilized forms are also included.

For oral administration, the compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., ationd oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound. For buccal administration the compositions may take the form of tablets or lozenges formulated in conventional manner. For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluorometbane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulating agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection.

Thus, for example, the compounds may be formulated with suitable polymeric or hydrophobic materials (for example as an emulsion in an acceptable oil) or ion exchange resins, or as sparingly soluble derivatives, for example, as a sparingly soluble salt. Other suitable delivery systems include microspheres which offer the possibility of local noninvasive delivery of drugs over an extended period of time. This technology utilizes microspheres of precapillary size which can be injected via a coronary catheter into any selected part of the e.g. heart or other organs without causing inflammation or ischemia. The administered therapeutic is slowly released from these microspheres and taken up by surrounding tissue cells (e.g. endothelial cells).

Systemic administration can also be by transmucosal or transdermal means. For transmucosal or transdermal admninistration, penetrants appropriate to the barrier to be permeated are used in the formulation. Such penetrants are generally known in the art, and include, for example, for transmucosal administration bile salts and fusidic acid derivatives. In addition, detergents may be used to facilitate permeation. Transmucosal administration may be through nasal sprays or using suppositories. For topical administration, the oligomers of the invention are formulated into ointments, salves, gels, or creams as generally known in the art. A wash solution can be used locally to treat an injury or inflammation to accelerate healing.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

4.4 Assays to Identify Terapeutics

Based on the identification of mutations that cause or contribute to the development of a disease or disorder that is associated with an IL-1 polymorphism or haplotype, the invention further features cell-based or cell free assays for identifying therapeutics. In one embodiment, a cell expressing an IL-1 receptor, or a receptor for a protein that is encoded by a gene which is in linkage disequilibrium with an IL-1 gene, on the outer surface of its cellular membrane is incubated in the presence of a test compound alone or in the presence of a test compound and another protein and the interaction between the test compound and the receptor or between the protein (preferably a tagged protein) and the receptor is detected, e.g., by using a microphysiometer (McConnell et al. (1992) Science 257:1906). An interaction between the receptor and either the test compound or the protein is detected by the microphysiometer as a change in the acidification of the medium. This assay system thus provides a means of identifying molecular antagonists which, for example, function by interfering with protein-receptor interactions, as well as molecular agonist which, for example, function by activating a receptor.

Cellular or cell-free assays can also be used to identify compounds which modulate expression of an IL-1 gene or a gene in linkage disequilibrium therewith, modulate translation of an mRNA, or which modulate the stability of an mRNA or protein. Accordingly, in one embodiment, a cell which is capable of producing an IL-1, or other protein is incubated with a test compound and the amount of protein produced in the cell medium is measured and compared to that produced from a cell which has not been contacted with the test compound. The specificity of the compound vis a vis the protein can be confirmed by various control analysis, e.g., measuring the expression of one or more control genes. In particular, this assay can be used to determine the efficacy of antisense, ribozyme and triplex compounds.

Cell-free assays can also be used to identify compounds which are capable of interacting with a protein, to thereby modify the activity of the protein. Such a compound can, e.g., modify the structure of a protein thereby effecting its ability to bind to a receptor. In a preferred embodiment, cell-free assays for identifying such compounds consist essentially in a reaction mixture containing a protein and a test compound or a library of test compounds in the presence or absence of a binding partner. A test compound can be, e.g., a derivative of a binding partner, e.g., a biologically inactive target peptide, or a small molecule.

Accordingly, one exemplary screening assay of the present invention includes the steps of contacting a protein or functional fragment thereof with a test compound or library of test compounds and detecting the formation of complexes. For detection purposes, the molecule can be labeled with a specific marker and the test compound or library of test compounds labeled with a different marker. Interaction of a test compound with a protein or fragment thereof can then be detected by determining the level of the two labels after an incubation step and a washing step. The presence of two labels after the washing step is indicative of an interaction.

An interaction between molecules can also be identified by using real-time BIA (Biomolecular Interaction Analysis, Pharmacia Biosensor AB) which detects surface plasmon resonance (SPR), an optical phenomenon. Detection depends on changes in the mass concentration of macromolecules at the biospecific interface, and does not require any labeling of interactants. In one embodiment, a library of test compounds can be immobilized on a sensor surface, e.g., which forms one wall of a micro-flow cell. A solution containing the protein or functional fragment thereof is then flown continuously over the sensor surface. A change in the resonance angle as shown on a signal recording, indicates that an interaction has occurred. This technique is further described, e.g., in BIAtechnology Handbook by Pharmacia.

Another exemplary screening assay of the present invention includes the steps of (a) forming a reaction mixture including. (i) an IL-1 or other protein, (ii) an appropriate receptor, and (iii) a test compound; and (b) detecting interaction of the protein and receptor. A statistically significant change (potentiation or inhibition) in the interaction of the protein and receptor in the presence of the test compound, relative to the interaction in the absence of the test compound, indicates a potential antagonist (inhibitor). The compounds of this assay can be contacted simultaneously. Alternatively, a protein can first be contacted with a test compound for an appropriate amount of time, following which the receptor is added to the reaction mixture. The efficacy of the compound can be assessed by generating dose response curves from data obtained using various concentrations of the test compound. Moreover, a control assay can also be performed to provide a baseline for comparison.

Complex formation between a protein and receptor may be detected by a variety of techniques. Modulation of the formation of complexes can be quantitated using, for example, detectably labeled proteins such as radiolabeled, fluorescently labeled, or enzymatically labeled proteins or receptors, by immnunoassay, or by chromatographic detection.

Typically, it will be desirable to immobilize either the protein or the receptor to facilitate separation of complexes from uncomplexed forms of one or both of the proteins, as well as to accommodate automation of the assay. Binding of protein and receptor can be accomplished in any vessel suitable for containing the reactants. Examples include microtitre plates, test tubes, and micro-centrifuge tubes: In one embodiment, a fusion protein can be provided which adds a domain that allows the protein to be bound to a matrix. For example, glutathione-S-transferase fusion proteins can be adsorbed onto glutathione sepharose beads (Sigma Chemical, St. Louis, Mo.) or glutathione derivatized microtitre plates, which are then combined with the receptor, e.g. an $^{35}$S-labeled receptor, and the test compound, and the mixture incubated under conditions conducive to complex formation, e.g. at physiological conditions for salt and pH, though slightly more stringent conditions may be desired. Following incubation, the beads are washed to remove any unbound label, and the matrix immobilized and radiolabel determined directly (e.g. beads placed in scintillant), or in the supernatant after the complexes are subsequently dissociated. Alternatively, the complexes can be dissociated from the matrix, separated by SDS-PAGE, and the level of protein or receptor found in the bead fraction quantitated from the gel using standard electrophoretic techniques such as described in the appended examples. Other techniques for immobilizing proteins on matrices are also available for use in the subject assay. For instance, either protein or receptor can be immobilized utilizing conjugation of biotin and streptavidin. Transgenic animals can also be made to identify agonists and antagonists or to confirm the safety and efficacy of a candidate therapeutic. Transgenic animals of the invention can include non-human animals containing a restenosis causative mutation under the control of an appropriate endogenous promoter or under the control of a heterologous promoter.

The transgenic animals can also be animals containing a transgene, such as reporter gene, under the control of an appropriate promoter or fragment thereof. These animals are useful, e.g., for identifying drugs that modulate production of an IL-1 protein, such as by modulating gene expression. Methods for obtaining transgenic non-human animals are well known in the art. In preferred embodiments, the expression of the restenosis causative mutation is restricted to specific subsets of cells, tissues or developmental stages utilizing, for example, to cis-acting sequences that control expression in the desired pattern. In the present invention, such mosaic expression of a protein can be essential for many forms of lineage analysis and can additionally provide a means to assess the effects of, for example, expression level which might grossly alter development in small patches of tissue within an otherwise normal embryo. Toward this end, tissue-specific regulatory sequences and conditional regulatory sequences can be used to control expression of the mutation in certain spatial patterns. Moreover, temporal patterns of expression can be provided by, for example, conditional recombination systems or prokaryotic transcriptional regulatory sequences. Genetic techniques, which allow for the expression of a mutation can be regulated via site-specific genetic manipulation in vivo, are known to those skilled in the art.

The transgenic animals of the present invention all include within a plurality of their cells a causative mutation transgene of the present invention, which transgene alters the phenotype of the "host cell". In an illustrative embodiment, either the, cre/loxP recombinase system of bacteriophage P1 (Lakso et al. (1992) *PNAS* 89:6232–6236; Orban et al. (1992) *PNAS* 89:6861–6865) or the FLP recombinase system of *Saccharomyces cerevisiae* (O'Gonnan et al. (1991) *Science* 251:1351–1355; PCT publication WO 92/15694) can be used to generate in vivo site-specific genetic recombination systems. Cre recombinase catalyzes the site-specific recombination of an intervening target sequence located between loxp sequences loxP sequences are 34 base pair nucleotide repeat sequences to which the Cre recombinase binds and are required for Cre recombinase mediated genetic recombination. The orientation of loxP sequences determines whether the intervening target sequence is excised or inverted when Cre recombinase is present (Abremski et al. (1984) *J. Biol. Chem.* 259:1509–1514); catalyzing the excision of the target sequence when the loxP sequences are oriented as direct repeats and catalyzes inversion of the target sequence when loxP sequences are oriented as inverted repeats.

Accordingly, genetic recombination of the target sequence is dependent on expression of the Cre recombinase. Expression of the recombinase can be regulated by promoter elements which are subject to regulatory control, e.g., tissue-specific, developmental stage-specific, inducible or repressible by externally added agents. This regulated control will result in genetic recombination of the target sequence only in cells where recombinase expression is mediated by the promoter element. Thus, the activation of expression of the causative mutation transgene can be regulated via control of recombinase expression.

Use of the crelloxP recombinase system to regulate expression of a causative mutation transgene requires the construction of a transgenic animal containing transgenes encoding both the Cre recombinase and the subject protein. Animals containing both the Cre recombinase and the restenosis causative mutation transgene can be provided through the construction of "double" transgenic animals. A convenient method for providing such animals is to mate two transgenic animals each containing a transgene.

Similar conditional transgenes can be provided using prokaryotic promoter sequences which require prokaryotic proteins to be simultaneous expressed in order to facilitate expression of the transgene. Exemplary promoters and the corresponding trans-activating prokaryotic proteins are given in U.S. Pat. No. 4,833,080.

Moreover, expression of the conditional transgenes can be induced by gene therapy-like methods wherein a gene encoding the transactivating protein, e.g. a recombinase or a prokaryotic protein, is delivered to the tissue and caused to be expressed, such as in a cell-type specific manner. By this method, the transgene could remain silent into adulthood until "turned on" by the introduction of the transactivator.

In an exemplary embodiment, the "transgenic non-human animals" of the invention are produced by introducing transgenes into the germline of the non-human animal. Embryonal target cells at various developmental stages can be used to introduce transgenes. Different methods are used depending on the stage of development of the embryonal target cell. The specific line(s) of any animal used to practice this invention are selected for general good health, good embryo yields, good pronuclear visibility in the embryo, and good reproductive fitness. In addition, the haplotype is a significant factor. For example, when transgenic mice are to be produced, strains such as C57BL/6 or FVB lines are often used (Jackson Laboratory, Bar Harbor, Me.). Preferred strains are those with H-$2^b$, H-$2^d$ or H-$2^q$ haplotypes such as C57BL/6 or DBA/1. The line(s) used to practice this invention may themselves be transgenics, and/or may be knock-outs (i.e., obtained from animals which have one or more genes partially or completely suppressed).

In one embodiment, the transgene construct is introduced into a single stage embryo. The zygote is the best target for microinjection. In the mouse, the male pronucleus reaches the size of approximately 20 micrometers in diameter which allows reproducible injection of 1–2 pl of DNA solution. The use of zygotes as a target for gene transfer has a major advantage in that in most cases the injected DNA will be incorporated into the host gene before the first cleavage (Brinster et al. (1985) *PNAS* 82:4438–4442). As a consequence, all cells of the transgenic animal will carry the incorporated transgene. This will in general also be reflected in the efficient transmission of the transgene to offspring of the founder since 50% of the germ cells will harbor the transgene.

Normally, fertilized embryos are incubated in suitable media until the pronuclei appear. At about this time, the nucleotide sequence comprising the transgene is introduced into the female or male pronucleus as described below. In some species such as mice, the male pronucleus is preferred. It is most preferred that the exogenous genetic material be added to the male DNA complement of the zygote prior to its being processed by the ovum nucleus or the zygote female pronucleus. It is thought that the ovum nucleus or female pronucleus release molecules which affect the male DNA complement, perhaps by replacing the protamines of the male DNA with histones, thereby facilitating the combination of the female and male DNA complements to form the diploid zygote. Thus, it is preferred that the exogenous genetic material be added to the male complement of DNA or any other complement of DNA prior to its being affected by the female pronucleus. For example, the exogenous genetic material is added to the early male pronucleus, as soon as possible after the formation of the male pronucleus, which is when the male and female pronuclei are well separated and both are located close to the cell membrane. Alternatively, the exogenous genetic material could be added to the nucleus of the sperm after it has been induced to undergo decondensation. Sperm containing the exogenous genetic material can then be added to the ovum or the decondensed sperm could be added to the ovum with the transgene constructs being added as soon as possible thereafter.

Introduction of the transgene nucleotide sequence into the embryo may be accomplished by any means known in the art such as, for example, microinjection, electroporation, or lipofection. Following introduction of the transgene nucleotide sequence into the embryo, the embryo may be incubated in vitro for varying amounts of time, or reimplanted into the surrogate host, or both. In vitro incubation to maturity is within the scope of this invention. One common method in to incubate the embryos in vitro for about 1–7 days, depending on the species, and then reimplant them into the surrogate host.

For the purposes of this invention a zygote is essentially the formation of a diploid cell which is capable of developing into a complete organism. Generally, the zygote will be comprised of an egg containing a nucleus formed, either naturally or artificially, by the fusion of two haploid nuclei from a gamete or gametes. Thus, the gamete nuclei must be ones which are naturally compatible, i.e., ones which result in a viable zygote capable of undergoing differentiation and developing into a functioning organism. Generally, a euploid zygote is preferred. If an aneuploid zygote is obtained, then the number of chromosomes should not vary by more than one with respect to the euploid number of the organism from which either gamete originated.

In addition to similar biological considerations, physical ones also govern the amount (e.g., volume) of exogenous genetic material which can be added to the nucleus of the zygote or to the genetic material which forms a part of the zygote nucleus. If no genetic material is removed, then the amount of exogenous genetic material which can be added is limited by the amount which will be absorbed without being physically disruptive. Generally, the volume of exogenous genetic material inserted will not exceed about 10 picoliters. The physical effects of addition must not be so great as to physically destroy the viability of the zygote. The biological limit of the number and variety of DNA sequences will vary depending upon the particular zygote and functions of the exogenous genetic material and will be readily apparent to one skilled in the art, because the genetic material, including the exogenous genetic material, of the resulting zygote must be biologically capable of initiating and maintaining the differentiation and development of the zygote into a functional organism.

The number of copies of the tansgene constructs which are added to the zygote is dependent upon the total amount of exogenous genetic material added and will be the amount which enables the genetic transformation to occur. Theoretically only one copy is required; however, generally, numerous copies are utilized, for example, 1,000–20,000 copies of the transgene construct, in order to insure that one copy is functional. As regards the present invention, there will often be an advantage to having more than one functioning copy of each of the inserted exogenous DNA sequences to enhance the phenotypic expression of the exogenous DNA sequences.

Any technique which allows for the addition of the exogenous genetic material into nucleic genetic material can be utilized so long as it is not destructive to the cell, nuclear membrane or other existing cellular or genetic structures. The exogenous genetic material is preferentially inserted into the nucleic genetic material by microinjection. Microinjection of cells and cellular structures is known and is used in the art Reimplantation is accomplished using standard methods. Usually, the surrogate host is anesthetized, and the embryos are inserted into the oviduct. The number of embryos implanted into a particular host will vary by species, but will usually be comparable to the number of off spring the species naturally produces.

Transgenic offspring of the surrogate host may be screened for the presence and/or expression of the transgene by any suitable method. Screening is often accomplished by Southern blot or Northern blot analysis, using a probe that is complementary to at least a portion of the transgene. Western blot analysis using an antibody against the protein encoded by the transgene may be employed as an alternative or additional method for screening for the presence of the transgene product. Typically, DNA is prepared from tail tissue and analyzed by Southern analysis or PCR for the transgene. Alternatively, the tissues or cells believed to express the transgene at the highest levels are tested for the presence and expression of the transgene using Southern analysis or PCR, although any tissues or cell types may be used for this analysis.

Alternative or additional methods for evaluating the presence of the transgene include, without limitation, suitable biochemical assays such as enzyme and/or immnunological assays, histological stains for particular marker or enzyme activities, flow cytometric analysis, and the like. Analysis of the blood may also be useful to detect the presence of the transgene product in the blood, as well as to evaluate the effect of the transgene on the levels of various types of blood cells and other blood constituents.

Progeny of the transgenic animals may be obtained by mating the transgenic animal with a suitable partner, or by in vitro fertilization of eggs and/or sperm obtained from the transgenic animal. Where mating with a partner is to be performed, the partner may or may not be transgenic and/or a knockout; where it is transgenic, it may contain the same or a different transgene, or both. Alternatively, the partner may be a parental line. Where in vitro fertilization is used, the fertilized embryo may be implanted into a surrogate host or incubated in vitro, or both. Using either method, the progeny may be evaluated for the presence of the transgene using methods described above, or other appropriate methods.

The transgenic animals produced in accordance with the present invention will include exogenous genetic material. Further, in such embodiments the sequence will be attached to a transcriptional control element, e.g., a promoter, which preferably allows the expression of the transgene product in a specific type of cell.

Retroviral infection can also be used to introduce the transgene into a non-human animal. The developing non-human embryo can be cultured in vitro to the blastocyst stage. During this time, the blastomeres can be targets for retroviral infection (Jaenich, R. (1976) *PNAS* 73:1260–1264). Efficient infection of the blastomeres is obtained by enzymatic treatment to remove the zona pellucida (*Manipulating the Mouse Embryo*, Hogan eds. (Cold Spring Harbor Laboratory Press, Cold Spring Harbor, 1986). The viral vector system used to introduce the transgene is typically a replication-defective retrovirus carrying the transgene (Jahner et al. (1985) *PNAS* 82:6927–6931; Van der Putten et al. (1985) *PNAS* 82:6148–6152). Transfection is easily and efficiently obtained by culturing the blastomeres on a monolayer of virus-producing cells (Van der Putten, supra; Stewart et al. (1987) *EMBO J.* 6:383–388). Alternatively, infection can be performed at a later stage. Virus or virus-producing cells can be injected into the blastocoele (Jahner et al. (1982) *Nature* 298:623–628). Most of the founders will be mosaic for the transgene since incorporation occurs only in a subset of the cells which formed the transgenic non-human animal. Further, the founder may contain various retroviral insertions of the transgene at different positions in the genome which generally will segregate in the offspring. In addition, it is also possible to introduce transgenes into the germ line by intrauterine retroviral infection of the midgestation embryo (Jahner et al. (1982) supra).

A third type of target cell for transgene introduction is the embryonal stem cell (ES). ES cells are obtained from pre-implantation embryos cultured in vitro and fused with embryos (Evans et al. (1981) *Nature* 292:154–156; Bradley et al. (1984) *Nature* 309:255–258; Gossler et al. (1986) *PNAS* 83: 9065–9069; and Robertson et al. (1986) *Nature* 322:445–448). Transgenes can be efficiently introduced into the ES cells by DNA transfection or by retrovirus-mediated transduction. Such transformed ES cells can thereafter be combined with blastocysts from a non-human animal. The ES cells thereafter colonize the embryo and contribute to the germ line of the resulting chimeric animal. For review see Jaenisch, R. (1988) *Science* 240:1468–1474.

The present invention is further illustrated by the following examples which should not be construed as limiting in any way. The contents of all cited references (including literature references, issued patents, published patent applications as cited throughout this application) are hereby expressly incorporated by reference. The practice of the present invention will employ, unless otherwise indicated, conventional techniques that are within the skill of the art. Such techniques are explained fully in the literature. See, for example, Molecular Cloning A Laboratory Manual, (2nd ed., Sambrook, Fritsch and Maniatis, eds., Cold Spring Harbor Laboratory Press: 1989); DNA Cloning, Volumes I and II (D. N. Glover ed., 1985); Oligonucleotide Synthesis (M. J.

Gait ed., 1984); U.S. Pat. No. 4,683,195; U.S. Pat. No. 4,683,202; and Nucleic Acid Hybridization (B. D. Hames & S. J. Higgins eds., 1984).

5. EXAMPLES

Example 1

Genotyping

All human subjects were unrelated, Caucasian, healthy blood donors from Sheffield (n=112). Subjects were typed at the loci indicated in Table 1.

TABLE 2

Markers Used in Haplotype Study

| Marker | Gene | Reference |
|---|---|---|
| 2221223 | IL1A | Todd & Naylor, Nucleic Acids Res. 19: 3756(1991) |
| gz5/gz6 | IL1A | Zuliani, et. al., Am. J. Hum. Genet. 46: 963–69 (1990) |
| −889 | IL1A | McDowell, et al., Anth. & Rheum. 38: 221–8(1995) |
| +3954 | IL1B | di Giovine, et al., Cytokine 7(6): 606 (1995) |
| −511 | IL1B | di Giovine, Hum. Molec. Genet. 1(6): 450 (1992) |
| gaat.p33330 | between IL1B and IL1RN | Murray, et al., Coop. Hum. Link. Center, unpublished |
| Y31 | between IL1B and IL1RN | Spurr, et al., Cytogenet. & Cell Genet. 73: 255–73 (1996) |
| VNTR | IL1RN | Tarlow, et al. Hum. Genet. 91: 403–4 (1993) |

The primer sequences and fluorescent labels used in PCR amplification of markers were as in Table 3.

TABLE 2

Primer Sequence and Flourescent Label for Genotyping

| Marker | Label | Primer Sequence |
|---|---|---|
| 2221223 | HEX | ATGTATAGAATTCCATTCCTG (SEQ ID NO. 8) |
| | | TAAAATCAAGTGTTGATGTAG (SEQ ID NO. 9) |
| gz51gz6 | FAM | GGGA7TACAGGCGTGAGCCACCGCG (SEQ ID NO. 10) |
| | | TTAGTATTGCTGGTAGTATTCATAT (SEQ ID NO. 11) |
| −889 | NONE | TGTTCTACCACCTGAACTAGG (SEQ ID NO. 12) |
| | | TTACATATGAGCCTTCCATG (SEQ ID NO. 13) |
| +3954 | NONE | CTCAGGTGTCCTCGAAGAAATCAAA (SEQ ID NO. 14) |
| | | GCTTTMGCTGTGAGTCCCG (SEQ ID NO. 15) |
| −511 | NONE | TGGCATTGATCTGGTTCATC (SEQ ID NO. 16) |
| | | GTTTAGGAATCTTCCCACTT (SEQ ID NO. 17) |
| gaat.p33330 | FAM | GAGGCGTGAGAATCTCAAGA (SEQ ID NO. 18) |
| | | GTGTCCTCAAGTGGATCTGG (SEQ 10 NO. 19) |
| Y31 | HEX | GGGCAACAGAGCAATGTTTCT (SEQ ID NO. 20) |
| | | CAGTGTGTCAGTGTACTGTT (SEQ ID NO. 21) |
| VNTR | NONE | CTCAGCAACACTCCTAT (SEQ ID NO. 22) |
| | | TCCTGGTCTGCAGGTAA (SEQ ID NO. 23) |

Reaction conditions were as described in Table 4.

TABLE 4

Reaction Conditions

| Marker | Conditions |
|---|---|
| 222/223 | 50 mM KCI, 10 mM Tris-HCI pH 9.0, 1.5 mM $MgCl_2$, 200:mM dNTPs, 25 ng primers, 50 ng template, 0.004% W-1 (Gibco-BRL) 0.2 u Taq, PCR was done at 30 cycles of 94° C. for 1". 55° C. for 1", 72° C. for 1" |
| gz5/gz6 | as per marker 2221223, except 1 u of Perfect Match (StrataGene) was added |
| −889 | per marker 222/223, except PCR was done for 1 cycle at 96° C. for 1", 40 cycles of 94° C. for 1", 46° C. for 1" 72° C. for 1" and 1 cycle of 72° C. for 4", products were cleaved with Ncol for analysis |
| +3954 | as per marker 222/223, except PCR was done for 35 cycles with annealing at 67.5° C., products were cleaved with Taq 1 for analysis |
| −511 | as per marker 2221223, except PCR was done for 1 cycle at 95° C. for 2", 35 cycles of 95° C. for 1", 53° C. for 1" 74° C. for 1" and 1 cycle of 74° C. for 4", products were cleaved with Aval and Bsu36I for analysis |
| gaat.p33330 | per marker 222/223 |
| Y31 | per marker 222/223 |
| VNTR | per marker 222/223 except with 1.7 mM $MgCl_2$, 1 cycle at 96° C. for 1"; 30 cycles of 94° C. for 1", 60° C. for 1", 70° C. for 1" and 1 cycle at 70° C. for 2" |

2221223, gz5/gz6, gaat.p33330 and Y31 PCR products were examined by agarose gel electrophoresis and the remainder of the PCR products were pooled according to the intensity of ethidium bromide staining 2 gl of the pool was analyzed on an ABI 373A automated sequencer and allee sizes were determined using the Genescan and Genotyper software. Alleles were globally binned using a simple computer program and numbered in order of size.

−889 PCR products were digested with NcoI and the resulting fragments sized on 8% PAGE. Allele 1 produces 83 and 16 bp fragments. Allele 2 produces a 99 bp fragment.

+3954 PCR products were digested with restriction enzyme Taq I. Allele 1 produces fragments of 97, 85 and 12 bp, and allele 2 produces fragments of 182 and 12 bp.

−511 PCR products were digested with Aval and Bsu36I and the fragments were sized by 8% PAGE. Allele 1 produces 190 and 114 bp fragments when digested with AvaI and a 304 bp fragment when digested with Bsu36I. Allele 2 produces a 304 bp fragment when digested with AvaI and 190 and 114 bp fragments when digested with Bsu36I.

VNTR PCR products were sized by electrophoresis on 2% agarose gel at 90V for 45 minutes. Allele 1 has 4 repeats and the PCR product is 412 bp, allele 2 has 2 repeats and the PCR product is 240 bp, allele 3 has 3 repeats and the PCR product is 326 bp, allele 4 has 4 repeats and the PCR product is 498 bp, allele 5 has 6 repeats and the PCR product is 584 bp.

Intergenic distances were determined by estimation based on the insert sizes of relevant PAC clones from a contig spanning the IL-1 gene cluster (Nicklin, et al., *Genomics* 19:38-24 (1994)). Intragenic distances were determined from the relevant nucleotide sequence obtained form the GENBANK database.

Example 2

Method for Estimating Linkage Disequilibrium

Because four of the markers studied herein are multiallelic, a preliminary analysis was carried out to determine which allelic combinations between pairs of loci contributed to the greatest disequilibrium, in order that the disequilibrium would not be masked when the alleles were grouped into biallelic systems. The E.H. program of Xie and Ott (Handbook of Human Genetic Link-age, 1994, John Hopkins University Press, 188–98), incorporated by reference herein, was used to estimate haplotype frequencies under H$_0$ (no linkage) and H$_1$ (allelic linkage allowed). It was found that the elaborate allele grouping, strategy had some advantages over commonly used methods, in that disequilibrium was detected between almost all pairwise combinations of markers examined and there was good correlation between disequilibrium and physical distance.

More specifically, the E.H. program of Xie and Ott was used to determine maximum likelihood estimates of disequilibriumn ($D_j$) between each pairwise combination of alleles, where $D_{ij}=h_{ij}-p_iq_j$ are the frequencies for allele i at locus 1 and allele j at locus 2 respectively, and $h_{ij}$ is the frequency of the haplotype ij. The program calculated maximum likelihood values for the haplotype frequencies (and hence allele frequencies) under H$_0$ (no association) and haplotype frequencies under H$_1$ (allelic association allowed). For markers with greater than two alleles, the E. H. estimate for allele frequencies correlated poorly with the allele frequencies as estimated directly from the sample population, and therefore gave no confidence to the $D_{ij}$ estimates given. It was therefore necessary to group alleles of the multi-allelic markers into a biallelic system. Analysis of the markers in a biallelic format has the added advantages that the notation $\hat{D}_{ij}$, $p_j$, $q_j$ and can be simplified to $\hat{D}$, p, and q respectively, where p and q are defined to be the frequencies of the rarer alleles at both loci (such that without loss of generality $p \leq q \leq 0.5$), and $\hat{D}$ is the estimated disequilibrium between those alleles.

Under a biallelic system, power is also much simpler to determine using equations as detailed by Hill (Hill, *Heredity*, 33: 229–39 (1974)). In addition, the sign of $\hat{D}$ becomes informative, such that $\hat{D}>0$ when the rarer alleles at each of the two loci are associated, and $\hat{D}<0$ when the rare allele at one locus is associated with the common allele at the other locus.

Because the method of allele grouping clearly affected the power to detect disequilibrium (Zouros, et al., *Genet*. 85: 543–50 (1977); Weir, et al., *Genet*. 88:633–42 (1976)), a preliminary analysis was conducted to ensure that the grouping did not mask disequilibrium between subsets of alleles. In this analysis, $\delta_{ij}=(O'_{ij}-E_{ij})/\sqrt{E_{ij}}$ was calculated for each haplotype, where $E_{ij}$ is the expected number of haplotpes ij assuming equilibrium ($E_{ij}=2n\ p_iq_j$, where n=number of individuals in the study), and $O'_{ij}$ is a basic estimate for the observed haplotpe count determined as follows. All genotypes that could be unambiguously resolved were haplotype counted. Bach double heterozygote ($i_1i_2/j_1j_2$) could be resolved into two possible haplotype sets, [$i_1J_1,i_2j_2$] or [$i_1J_2,i_2j_1$]. Using the haplotype frequencies as estimated from the unambiguous haplotype count, the probability of each set was calculated and used as a "partial" count. In this way the ambiguous genotypes were also haplotype counted, and the total counts (ambiguous plus unambiguous) constituted the $O'_{ij}$'s used in $\delta_{ij}$. Once establishecl, the magnitude and sign of the $\delta_{ij}$'s were used to determine which allelic combinations showed greatest deviation from the null hypothesis of no association. This information was used to group alleles at the multiallelic loci into biallelic systems to enable efficient use of the E.H. program.

In order to compare the degree of disequilibrium between different pairwise combinations of loci, a frequency independent measure of disequilibrium $\tilde{D}$, the proportion of maximum possible disequilibrium in the given direction) was calculated, where $\tilde{D}=\hat{D}/|D_{max}|$ (Thompson, et al., *Am. J. Hum. Genet*. 42: 113–24 (1988)). The relationship between p and q are such that $p \leq q \leq 0.5$, and it can therefore be written that $-pq \leq D \leq p(1-q)$ such that when $\hat{D}<0$, $D_{max}=-pq$ and when $\hat{D}>0$, $D_{max}=p(1-q)$. Output from the E.H. program included log-likelihoods for the maximum likelihood parameter values under H$_0$ and H$_1$, and since $-2\ln(L_0/L_1) \sim X_1^2$. where $L_0$ and $L_1$ are the likelihoods under H$_0$ and H$_1$, p- values could then be determined for each test.

The asymptotic variance for $\hat{D}$, under H$_0$: D=0 and H$_1$ were computed using the formula as defined by Hill (*Heredity* 33: 229–39 (1974)) for genotypic data. Using these, the power for each pairwise comparison could be calculated.

Common haplotypes containing all 8 loci were identified from the preliminary analysis of $\delta_{ij}$ described above, and backed up by the magnitude and sign of the disequilibria once the alleles at the multiallelic loci had, been grouped. For these loci, the allele in the group which contributed most to the disequilibrium has been identified on the haplotype. To estimate the population haplotype frequencies, rates of carriage of at least one copy of the relevant alleles in the population were determined. These do not represent true haplotypes since phase is unknown. Monte Carlo simulation techniques were used to test for significant deviation from a simulated null distribution for these combined carriages under the assumption of no association.

Example 3

Estimation of Linkage Disequilibrium in the IL-1 Gene Cluster

A number of biallelic and multiallelic markers in and around the IL-1 genes have been identified. However, the extent of linkage disequilibrium between the markers, and the prevalence of multimarker haplotypes in the general population have not until now been identified.

FIG. 1 shows the relative positions of the 8 marker loci used in this study. DNA samples from 212 unrelated healthy volunteers were genotyped for each of these markers, and the resulting estimates of allele frequencies are shown in Table 5.

TABLE 5

| Estimated frequencies of marker alleles | | | | | | | |
|---|---|---|---|---|---|---|---|
| 222/223 | freq. | gz5/gz6 | freq. | −889 | freq. | +3953 | freq |
| 1 (126 bp) | 0.005 | 1 (79 bp) | 0.003 | 1 (Ncol) | 0.714 | 1 (2 Taq1) | 0.812 |
| 2 (128 bp) | 0.018 | 2 (82 bp) | 0.005 | 2 | 0.286 | 2 | 0.188 |
| 3 (130 bp) | 0.378 | 3 (88 bp) | 0.676 | | | | |
| 4 (132 bp) | 0.299 | 4 (91 bp) | 0.316 | | | | |
| 5 (134 bp) | 0.016 | | | | | | |
| 6 (136 bp) | 0.208 | | | | | | |

TABLE 5-continued

Estimated frequencies of marker alleles

| | |
|---|---|
| 7 (138 bp) | 0.055 |
| 8 (140 bp) | 0.003 |
| 9 (142 bp) | 0.010 |
| 10 (144 bp) | 0.008 |
| *total 384 | 392   398   398 |

| −511 | freq. | gaat.p33330 | freq. | Y31 | freq. | VNTR | freq. |
|---|---|---|---|---|---|---|---|
| 1 | 0.618 | 1 (189 bp) | 0.658 | 1 (148 bp) | 0.092 | 1 | 0.744 |
| 2 (Bsu36I) | 0.382 | 2 (193 bp) | 0.002 | 2 (158 bp) | 0.008 | 2 | 0.256 |
| | | 3 (197 bp) | 0.255 | 3 (160 bp) | 0.454 | | |
| | | 4 (201 bp) | 0.084 | 4 (162 bp) | 0.062 | | |
| | | | | 5 (164 bp) | 0.003 | | |
| | | | | 6 (166 bp) | 0.122 | | |
| | | | | 7 (168 bp) | 0.035 | | |
| | | | | 8 (170 bp) | 0.030 | | |
| | | | | 9 (172 bp) | 0.095 | | |
| | | | | 10 (174 bp) | 0.087 | | |
| | | | | 11 (176 bp) | 0.003 | | |
| | | | | 12 (178 bp) | 0.011 | | |
| | 398 | | 404 | | 370 | | 398 |

*number of chromosomes analyzed
Note - Allele names (and sizes) are given in boldface.

To determine the linkage disequilibria between pairwise combinations of loci, the computer program of Xie and Ott was used. This program was found to be most efficient when used with biallelic systems, therefore alleles at the multiallelic loci were grouped in the most appropriate way for each pairwise comparison, such that disequilibrium between subsets of alleles was not masked.

In Table 6, the disequilibria between pairs of loci are expressed as $\tilde{D}$, the ratio of $\hat{D}$ to its maximum value $D_{max}$ and are shown together with the approximate physical distances between the loci in kilobase pairs.

TABLE 6

Disequilibrium ($\tilde{D} = \hat{D}/|D_{max}|$) and physical distances between markers

| | 222/223 | gz5/gz6 | −889 | +3953 |
|---|---|---|---|---|
| 222/223 | — | +0.872 | +0.829 | +0.710 |
| gz5/gz6 | 2.5 | — | −0.889 | −0.695 |
| −889 | 7 | 4.5 | — | +0.804 |
| +3953 | 55 | 55 | 50 | — |
| −511 | 60 | 60 | 55 | 4.5 |
| gaat.p33330 | 260 | 260 | 255 | 205 |
| Y31 | 310 | 310 | 305 | 255 |
| VNTR | 380 | 380 | 375 | 325 |

| | −511 | gaat.p33330 | Y31 | VNTR |
|---|---|---|---|---|
| 222/223 | +0.535 | +0433 | +0.364 | −0.499 |
| gz5/gz6 | +0.540 | +0.517 | −0.503 | +0.286 |
| −889 | −0.264 | +0.337 | +0.318 | −0.207 |
| +3954 | −0.617 | +0.409 | −0.475 | 0.439 |
| −511 | — | +0.691 | −0.456 | +0.448 |
| gaat.p33330 | 200 | — | +0.639 | +0.442 |
| Y31 | 250 | 50 | — | −0.765 |
| VNTR | 320 | 120 | 70 | — |

Note - disequilibrium values are shown at the top right, approximate physical distances in Kb are shown at the bottom left. Intergenic distances are given to the nearest 5 Kb.

Table 7 shows the power to detect 50% $D_{max}$ for each locus combination, and the p values for each corresponding D.

TABLE 7

Power to detect 50% $D_{max}$ and p values of $-2Ln\ (L_0L_1)$

| | 222/223 | gz5/gz6 | −889 | +3953 |
|---|---|---|---|---|
| 22/223 | — | −100(+) | −100(+) | 98(+) |
| gz5/gz6 | $<1 \times 10^{-10}$ | — | 87(−) | 60(−) |
| −889 | $<1 \times 10^{-10}$ | $<3 \times 10^{-8}$ | — | −100(+) |
| +3954 | $-1 \times 10^{-7}$ | $*-9 \times 10^{-3}$ | $<1 \times 10^{-10}$ | — |
| −511 | $-9 \times 10^{-10}$ | $-4 \times 10^{-10}$ | $*-9.4 \times 10^{-2}$ | $*-2.6 \times 10^{-2}$ |
| gaat.p33330 | $-9 \times 10^{-8}$ | $-2 \times 10^{-9}$ | $*-1.7 \times 10^{-2}$ | $-5 \times 10^{-4}$ |
| Y31 | $-1 \times 10^{-4}$ | $-4 \times 10^{-4}$ | $-6 \times 10^{-4}$ | $-1 \times 10^{-7}$ |
| VNTR | $-1 \times 10^{-3}$ | $-1 \times 10^{-3}$ | $*-3 \times 10^{-1}$ | $*-1.2 \times 10^{-1}$ |

| | −511 | gaat.p33330 | Y31 | VNTR |
|---|---|---|---|---|
| 22/223 | ~100(+) | ~100(+) | ~100(+) | 93(−) |
| gz5/gz6 | ~100(+) | ~100(+) | 98(−) | ~100(+) |
| −889 | 96(−) | 89(+) | ~100(+) | 78(−) |
| +3954 | 79(−) | 97(+) | ~100(+) | 52(−) |
| −511 | — | ~100(+) | ~100(−) | ~100(+) |
| gaat.p33330 | $<1 \times 10^{-10}$ | — | 49(+) | ~100(+) |
| Y31 | $~2 \times 10^{-4}$ | $*~7 \times 10^{-3}$ | — | 89(−) |
| VNTR | $~8 \times 10^{-6}$ | $~1 \times 10^{-9}$ | $2 \times 10^{-7}$ | — |

Note - Power is shown at the top right with the sign of disequilibrium in brackets; pointwise p-values are shown (uncorrected) at the bottom left. For an overall significance level of p = 0.05, pointwise significance level is 0.0018 for 28 comparisons.
*Not significant at p = 0.0018 threshhold Significant linkage disequilibrium ($p_{corr}<0.05$) was detected between most combinations of loci, with only a few exceptions. These include the comparisons between the VNTR and the more distant biallelic markers, +3954, and −889, in which the disequilibrium is in the negative direction and consequently the power is reduced (Table 7). The correlation between disequilibrium D and physical distance was r=−0.752 (p<0.0001, one tailed) (FIG., 2).

In order to compare different grouping methods for the multiallelic markers, D was calculated for all the comparisons involving 222/223 using two additional grouping strategies. The first of these was a "common allele versus the rest" approach, and the second was a grouping based on allele size, using the bimodal distribution of allele frequency versus size which was observed for all the multiallelic markers examined. The results of this analysis are shown in Table 8, where D values for the three grouping methods are compared.

TABLE 8

D values for three methods of grouping alleles at the multiallelic marker loci

| | $\delta_{ij}^-$ | common vs. rest | allele size |
|---|---|---|---|
| gz5/gz6 | 0.87 | 0.79 | 0.77 |
| −899 | 0.83 | 0.81 | 0.98 |
| +3954 | 0.71 | *0.74 | 0.77 |
| −511 | 0.54 | *0.15 | 0.61 |
| gaat.p33330 | 0.43 | *0.03 | 0.53 |
| Y31 | 0.36 | *0.12 | 0.16 |
| VNTR | 0.5 | 0.48 | *0.04 |

Note- Values re given for the disequilibrium between 222/223 and the other markers listed.
*indicates not significant at p = 0.05 level, even before correction for multiple testing.

It can be seen that the disequilibrium is not detected in several instances using these other grouping strategies, notably 222/223 with −511 and gaat.p33330 in the common versus rest approach, 222/223 with Y31 in both the common versus rest and allele size approaches, and 222/223 with VNTR in the allele size approach.

Examination of which alleles of the multiallelic loci were contributing greatest to the disequilibrium, from the determination of $\delta_{ij}$ revealed the existence of 2 haplotypes containing alleles of all 8 loci. These were confirmed by examination of the haplotype frequencies and disequilibrium values obtained after the grouping. The first haplotype: alleles 44112332 (expressed in chromosome order, see FIG. 1) is the most common (carriage of 34/198), and is present 7 times more frequently than expected (expected=4.5/198) (p<0.000001). The second haplotype: alleles 33221461 (carriage of 2/206) was present 4 times more frequently than expected (expected 0.5/206), but this was not statistically significant (p~0.106). However, examination of a larger sample size might assist in increasing the statistical significance of this finding.

The data presented indicate a significant degree of linkage disequilibrium across an approximately 400 Kb stretch of chromosome 2q13. The disequilibrium was strong both for the three markers within the IL-1α gene, as might be expected, but was also strong between some of the more distantly separated markers (−899/+3954;D=+0.804, physical distance=50 Kb) (Table 6). However, D was considerably diminished between the extreme ends of the cluster. Within the IL-1β gene, a moderate value of D (+3954/−511; D=−0.617) was obtained, although this was not significant when corrected for multiple comparisons, probably reflecting the reduction in power when disequilibrium is in the negative direction (Thompson, et al, *Am J Hum. Genet.* 42: 113–24 (1988)).

Overall, there is a good correlation between physical distance and linkage disequilibrium (FIG. 2); r=−0.752. The reliability of r itself depends partly on the reliability of the estimates of both physical distance and D. Over the short distances, the physical distances are accurate since they are determined from known DNA sequence, whereas the longer range estimates are less precise. The power can be taken tentatively as one indicator of the reliability of D, since if power is low this indicates that the sample size was too small, and with low sample sizes the estimates for D may be unreliable.

The success of the elaborate grouping strategy is indicated by Table 8, which shows several instances where disequilibrium between particular loci is apparently low or not detected when other commonly used grouping methods are employed. The disadvantages of the grouping strategy used here are that it is rather laborious since the information used for the grouping was based on an approximate estimate of the "observed" haplotype frequencies (see Example 2). For the more polymorphic markers the higher heterozygote meant that the estimate of $\delta_{ij}$ was less precise since there was a higher proportion of ambiguous haplotypes. Notwithstanding this drawback, care was taken to take into account both the sign and magnitude of $\delta_{ij}$, and the frequencies of the alleles concerned.

The method could be simplified, in a sufficiently large study, by just considering the unambiguous haplotypes when determining the grouping. The determination of $\delta_{ij}$ uses the maximum amount of prior knowledge for the grouping of the multiallelic markers, and this may be the reason why disequilibrium between almost all pairwise combinations of markers was detected.

The two haplotypes containing all 8 markers, as well as other shorter haplotypes, are of particular interest since it is likely that particular combinations of alleles of the IL-1 genes may act in concert to determine an overall inflammatory phenotype. An understanding of which markers are in strong linkage disequilibrium not only allows for more rational design of genetic studies but also may provide clues to disease mechanism. Therefore, in addition to the alleles identified herein, the IL-1 (44112332) haplotype may contain the following alleles:

allele 2 of the 1731 marker of the IL1RN gene (A at position 173 1);

allele 2 of the 1812 marker of the IL1RN gene (A at position 1812);

allele 2 of the 1868 marker of the IL1RN gene (G at position 1868);

allele 2 of the 1887 marker of the IL1RN gene (C at position 1887);

allele 2 of the 8006 marker of the IL1RN gene (contains a HpaII or MspI site)

allele 2 of the 8061 marker of the IL1RN gene (lacks a MwoI site)

allele 2 of the 9589 marker of the IL1RN gene (contains an SspI site)

Furthermore, the following PCR primers may be used to amplify these alleles:

TTACGCAGATAAGAACCAGTTTGG (SEQ ID NO. 24)

TTTCCTGGACGCTTGCTCACCA (SEQ ID NO. 25)

(used for 1731, 1812, 1868, and 1887)

TTCTATCTGAGGAACAACCAACTAGTAGC (SEQ ID NO. 26)

CACCAGACTTGACACAGGACAGGCACATC (SEQ ID NO. 27)

(used for 8006)

CGACCCTCTGGGAGAAAATCCAGCAAG (SEQ ID NO. 28)

(used with SEQ ID NO. 20 for 8006)

ACACAGGAAGGTGCCAAGCA (SEQ ID NO. 29)

TGCAGACAGACGGGCAAAGT (SEQ ID NO. 30)

(used for 8006 and 9S89)

TTGTGGGGACCAGGGGAGAT (SEQ ID NO. 31), and

AGCCTGGCACTCTGCTGAAT (SEQ ID NO. 32)

(used for 9589).

Example 4

The IL-1 (441123–32) Haplotype is Associated with Diabetic Nephropathy

The presence of the two haplotypes described herein was investigated in healthy and diseased populations to determine if the haplotypes were associated with inflammatory disease. 81 non-insulin dependant diabetes mellitus (NIDDM) patients with nephropathy were compared with 198 ethnically matched healthy subjects in example 3 and 147 NIDDM patients without nephropathy. Genotyping was carried out as in example 1.

The IL-1 (44112332) haplotype was carried by 24 of 79 of the NIDDM nephropathy patients and 25 of 141 NIDDM without nephropathy patients. However, the second haplotype (3322146 1) was not found in the nephropathy patients (0/8 1). The IL-1 (44112332) haplotype was significantly over represented in the patient group compared with the healthy control group (24/79 vs. 34/198; p=0.015) and the NIDDM without nephropathy group (24/79 vs. 25/141; p=0.03).

Example 5
An IL-1 Haplotype is Associated with Inflammatory Disease

This is a prophetic example. Other diseases are examined as per Example 4. The IL-1 (44112332) haplotype is found to be associated with coronary artery disease, osteoporosis, nephropathy in diabetes mellitus, alopecia areata, Graves disease, systemic lupus erythematosus, lichen sclerosis and ulcerative colitis.

Likewise, the IL-1 (33221461) haplotype is associated with periodontal disease, juvenile chronic arthritis, psoriasis, insulin dependant diabetes and diabetic retinopathy.

Example 6
Novel Markers are Linked to an, IL-1 Haplotype

This is a prophetic example. Additional markers are identified by sequence and restriction enzyme analysis of the 2q13–14 region. These new markers are identified as belonging to an IL-1 haplotype in the manner described in Examples 2 and 3.

Example 7
The IL-1 (44112332) Haplotype is Used to Predict Disease Susceptibility This is a prophetic example. A patient with a family history of ulcerative colitis is genotyped for the presence of the IL-1 (44112332) haplotype. Genotyping is performed as in Example I and the patient is determined to carry one or more alleles of the haplotype. The patient is thus treated with IL-1 antagonists to prevent disease.

A second patient with a family history of coronary artery disease is genotyped at the IL-1 gene cluster. The patient is found to carry one or more alleles; of the IL-1 (44112332) haplotype and be homozygous for the VNTR allele 2. Thus, the patient is 5.4 times as likely to develop coronary artery disease as the general population and is treated vigorously to prevent disease.

Example 8
Additional Haplotypes are Statistically Significant

This is a prophetic example. An additional 400 chromosomes are typed as per Example 1 and linkage disequilibrium assessed as per Example 2. The IL-1 (33221461) haplotype is found to be present about 4 times more frequently than expected (p–0.05).

In a similar manner, the following markers are determined to be present in the IL-1 (44112332) haplotype ($p<<0.05$).

allele 2 of the 1731 marker of the IL1RN gene
allele 2 of the 1812 marker of the IL1RN gene
allele 2 of the 1868 marker of the IL1RN gene
allele 2 of the 1887 marker of the IL1RN gene
allele 2 of the 8006 marker of the IL1RN gene
allele 2 of the 8061 marker of the IL1RN gene
allele 2 of the 9589 marker of the IL1RN gene

What is claimed is:

1. A method for detecting whether a subject is suffering from or is perdisposed to developing a disease or condition associated with an IL-1 inflammatory haplotype, comprising detecting one or more alleles selected from the group consisting of: allele 4 of the 222/223 marker of IL-1A, allele 4 of the gz5/gz6 marker of IL-1A, allele 1 of the −889 marker of IL-1A, allele 1 of the +3954 marker of IL-1B, allele 2 of the −511 marker of IL-1B, allele 3 of the gaat.p33330 marker, allele 3 of the Y31 marker, allele 2 of +2018 of IL-1RN, allele 1 of +4845 of IL-1A, allele 3 of the 222/223 marker of IL-1A, allele 3 of the gz5/gz6 market of IL-1A, allele 2 of the −889 marker of IL-1A, allele 2 of the +3954 marker of IL-1B, allele 1 of the −511 marker of IL-1B, allele 4 of the gaat.p33330 marker, allele 6 of the Y31 marker, allele 1 of +2018 of IL-1RN, allele 2 of +4845 of IL-1A, and allele 1 of the VNTR marker of IL-1R, wherein the presence of said one or more alleles indicates that the subject is predisposed to the development of or has the disease or condition.

2. A method of claim 1, wherein the disease of condition is selected from the group consisting of an inflammatory disease, a degenerative dimase m immunological disorder, an infectious disexs; a trauma induced disease, and a cancer.

3. A method of claim 1, wherein said detecting step is selected from the group consisting of:
 a) allele specific oligonucleotide hybridization;
 b) size analysis;
 c) sequencing;
 d) hybridization;
 e) 5' nuclease digestion;
 f) single-stranded conformation polymorphism;
 g) allele specific hybridization;
 h) primer specific extension; and
 j) oligonucleotide ligation assay.

4. A method of claim 1, wherein prior to or in conjunction with detection, the nucleic acid sample is subject to an amplification step.

5. A method of claim 4, wherein said amplification step employs a primer selected from the group consisting of any of SEQ ID Nos.8–32.

6. A method of claim 3, wherein said size analysis is preceded by a restriction enzyme digestion.

7. A method for selecting an appropriate therapeutic for an individual that is suffering from or is predisposed to developing a disease or disorder associated with an IL-1 polymorphism, comprising the steps of: detecting one or more alleles selected from the group consisting of; allele 4 of the 222/223 marker of IL-1A, allele 4 of the gz5/gz6 marker of IL-1A, allele 1 of the –889 marker of IL-1A, allele 1 of the +3954 marker of IL-1B, allele 2 of the –511 marker of IL-1B, allele 3 of the gaat.p33330 marker, allele 3 of the Y31 marker, allele 2 of +2018 of IL-1RN, allele 1 of +4845 of IL-1A, allele 3 of the 222/223 marker of IL-1A, allele 3 of the gz5/gz6 marker of IL-1A, allele 2 of the –889 marker of IL-1A, allele 2 of the +3954 marker of IL-1B, allele 1 of the –511 marker of IL-1B, allele 4 of the gaat.p33330 marker, allele 6 of the Y31 marker, allele 1 of +2018 of IL-1RN, allele 2 of +4845 of IL-1A, and allele 1 of the VNTR marker of IL-1RN, and selecting a therapeutic that compensates for a causative functional mutation that is in linkage disequilibrium with the IL-1 alleles.

8. A method of claim 7, wherein said detecting is performed using a technique selected from the group consisting of:
 a) allele specific oligonucleotide hybridization;
 b) size analysis;
 c) sequencing;
 d) hybridization;
 e) 5' nuclease digestion;
 f) single-stranded conformation polymorphism;
 g) allele specific hybridization;
 h) primer specific extension; and
 j) oligonucleotide ligation assay.

9. A method of claim 7, wherein prior to or in conjunction with detecting, the nucleic acid sample is subjected to an amplification step.

10. A method of claim 9, wherein said amplification step employs a primer selected from the group consisting of SEQ ID Nos. 8–32.

11. A method of claim 8, wherein said size analysis is preceded by a restriction enzyme digestion.

12. A method of claim 8, wherein the disease or condition is selected from the group consisting of: an inflammatory disease, a degenerative disease an immunological disorder, an infectious disease, a trauma induced disease, and a cancer.

13. A method of claim 8, wherein the therapeutic is a modulator of an IL-1 activity.

14. A method of claim 13, wherein the IL-1 activity is IL-1α.

15. A method of claim 13, wherein the IL-1 activity is IL-1β.

16. A method of claim 13, wherein the IL-1 activity is IL-1RN.

17. A method of claim 13, wherein the modulator of as IL-1 activity is a protein, peptide, peptidomimetics, small molecule, nucleic acid or a nutraceutical.

18. A method of claim 13, wherein the modulator is an agonist.

19. A method of claim 13, wherein the modulator is an antagonist.

20. A method for treating or preventing the development of a disease or condition associated with an IL-1 polymorphism in a subject comprising the steps of: detecting one or more alleles selected from the group consisting of: allele 4 of the 222/223 market of IL-1A allele 4 of the gz5/gz6 marker of IL-1A, allele 1 of the –889 marker of IL-1A, allele 1 of the +3954 marker of IL-1B, allele 2 of the –511 marker of IL-1B, allele 3 of the gaat.p33330 marker, allele 3 of the Y31 marker, allele 2 of +2019 of IL-1RN, allele 1 of +4845 of IL-1A, allele 3 of the 222/223 marker of IL-1A, allele 3 of the gz5/gz6 marker of IL-1A, allele 2 of the –889 marker of IL-1A, allele 2 of the +3954 maker of IL-1B, allele 1 of the –511 marker of IL-1B, allele 4 of the gaat.p33330 marker, allele 6 of the Y31 marker, allele 1 of +2018 of IL-1RN, allele 2 of +4845 of IL-1A, and allele 1 of the VNTR marker of IL-1RN; and administering to the subject a therapeutic that compensates for a causative mutation that is in linkage disequilibrium with the IL-1 inflammatory haplotype.

21. A method of claim 20, wherein the detecting step is selected from the group consisting of:
 a) allele specific oligonucleotide hybridization;
 b) size analysis;
 c) sequencing;
 d) hybridization;
 e) 5' nuclease digestion;
 f) single-stranded conformation polymorphism;
 g) allele specific hybridization;
 h) primer specific extension; and
 j) oligonucleotide ligation assay.

22. A method of claim 20, wherein prior to or in conjunction with detecting, the nucleic acid sample is subjected to an amplification step.

23. A method of claim 20, wherein said amplification step employs a primer selected from the group consisting of any of SEQ ID Nos. 8–32.

24. A method of claim 21, wherein said size analysis is preceded by a restriction enzyme digestion.

25. A method of claim 21, wherein the therapeutic is selected from the group coasting of: a modulator of an IL-1 activity.

26. A method of claim 25, wherein the IL-1 activity is IL-1α.

27. A method of claim 25, wherein the IL-1 activity is IL-1β.

28. A method of claim 25, wherein the IL-1 activity is IL-1Ra.

29. A method of claim 25, wherein the therapeutic is a protein, peptide, peptidomimetics, small molecule or a nucleic acid.

30. A method of claim 25, wherein the modulator is an agonist.

31. A method of claim 25, wherein the modulator is an antagonist.

32. The method of claim 1, further comprising detecting allele 2 of the VNTR marker of IL-1RN.

33. The method of claim 7, further comprising detecting allele 2 of the VNTR marker of IL-1RN.

34. The method of claim 20, further comprising detecting allele 2 of the VNTR marker of IL-1RN.

35. A method for detecting whether a subject is suffering from or is predisposed to developing a cardiovascular disease, comprising detecting one or more alleles selected from the group consisting of: allele 4 of the 222/223 marker of IL-1A, allele 4 of the gz5/gz6 marker of IL-1A, allele 1 of the −889 marker of IL-1A, allele 1 of the +3954 marker of IL-1B, allele 2 of the −511 marker of IL-1B, allele 3 of the gaat.p33330 marker, allele 3 of the Y31 marker, allele 2 of +2018 of IL-1RN, allele 1 of +4845 of IL-1A, allele 3 of the 222/223 marker of IL-1A, allele 3 of the gz5/gz6 marker of IL-1A, allele 2 of the −889 marker of IL-1A, allele 2 of the +3954 marker of IL-1B, allele 1 of the −511 marker of IL-1B, allele 4 of the gaat.p33330 market, allele 6 of the Y31 marker, allele 1 of +2018 of IL-1RN, allele 2 of +4845 of IL-1A, and allele 1 of the VNTR marker of IL-1RN, wherein the presence of said one or mom alleles indicates that the subject is predisposed to the development of or has a cardiovascular disease.

36. A method for detecting whether a subject is suffering from or is predisposed to developing osteoporosis, comprising detecting one or more alleles selected from the group consisting of: allele 4 of the 222/223 marker of IL-1A, allele 4 of the gz5/gz6 marker of IL-1A, allele 1 of the −889 marker of IL-1A, allele 1 of the +3954 marker of IL-1B, allele 2 of the −511 marker of IL-1B, allele 3 of the gaat.p33330 marker, allele 3 of the Y31 marker, allele 2 of +2018 of IL-1RN, allele 1 of +4845 of IL-1A, allele 3 of the 222/223 marker of IL-1A, allele 3 of the gz5/gz6 marker of IL-1A, allele 2 of the −889 marker of IL-1A, allele 2 of the +3954 marker of IL-1B, allele 1 of the −511 marker of IL-1B, allele 4 of the gaat.p33330 marker, allele 6 of the Y31 marker, allele 1 of +2018 of IL-1RN, allele 2 of +4845 of IL-1A, and allele 1 of the VNTR marker of IL-1RN, wherein the presence of said one or more alleles indicates that the subject is predisposed to the development of or has osteoporosis.

37. A method for selecting an appropriate therapeutic for an individual that is suffering from or is predisposed to developing a cardiovascular disease, comprising the steps of: detecting one or more alleles selected from the group consisting of: allele 4 of the 222/223 marker of IL-1A, allele 4 of the gz5/gz6 marker of IL-1A, allele 1 of the −889 marker of IL-1A, allele 1 of the +3954 marker of IL-1B, allele 2 of the −511 marker of IL-1B, allele 3 of the gaat.p33330 marker, allele 3 of the Y31 marker, allele 2 of +2018 of IL-1B, allele 1 of +4845 of IL-1A, allele 3 of the 222/223 marker of IL-1A, allele 3 of the gz5/gz6 marker of IL-1A, allele 2 of the −889 marker of IL-1A, allele 2 of the +3954 marker of IL-1B, allele 1 of the −511 marker of IL-1B, allele 4 of the gaat.p33330 marker, allele 6 of the Y31 marker, allele 1 of +2018 of IL-1RN, allele 2 of +4845 of IL-1A, and allele 1 of the VNTR marker of IL-1RN, and selecting a therapeutic that compensates for a causative functional mutation that is in linkage disequilibrium with the IL-1 alleles.

38. A method for selecting an appropriate therapeutic for an individual that is suffering from or is predisposed to developing osteoporosis, comprising the steps of: detecting one or more alleles selected from the group consisting of: allele 4 of the 222/223 marker of IL-1A, allele 4 of the gz5/gz6 marker of IL-1A, allele 1 of the −889 marker of IL-1A, allele 1 of the +3954 marker of IL-1B, allele 2 of the −511 marker of IL-1B, allele 3 of the gaat.p33330 marker, allele 3 of the Y31 marker, allele 2 of +2018 of IL-1RN, allele 1 of +4845 of IL-1A, allele 3 of the 222/223 marker of IL-1A, allele 3 of the gz5/gz6 marker of IL-1A, allele 2 of the −889 marker of IL-1A, allele 2 of the +3954 marker of IL-1B, allele 1 of the −511 marker of IL-1B, allele 4 of the gaat.p33330 marker, allele 6 of the Y31 marker, allele 1 of +2019 of IL-1RN, allele 2 of +4845 of IL-1A, and allele 1 of the VNTR marker of IL-1RN, and selecting a therapeutic that compensates for a causative functional mutation that is in linkage disequilibrium with the IL-1 alleles.

39. A method for treating or preventing the development of a cardiovascular disease in a subject comprising the steps of: detecting one or more alleles selected from the group consisting of: allele 4 of the 222/223 marker of IL-1A, allele 4 of the gz5/gz6 marker of IL-1A, allele 1 of the −889 marker of IL-1A, allele 1 of the +3954 marker of IL-1B, allele 2 of the −511 marker of IL-1B, allele 3 of the gaat.p33330 marker, allele 3 of the Y31 marker, allele 2 of +2018 of IL-1RN, allele 1 of +4845 of IL-1A, allele 3 of the 222/223 marker of IL-1A, allele 3 of the gz5/gz6 marker of IL-1A, allele 2 of the −889 marker of IL-1A, allele 2 of the +3954 marker of IL-1B, allele 1 of the −511 marker of IL-1B, allele 4 of the gaat.p33330 marker, allele 6 of the Y31 marker, allele 1 of +2018 of IL-1RN, allele 2 of +4845 of IL-1A, and allele 1 of the VNTR marker of IL-1RN; and administering to the subject a therapeutic that compensates for a causative mutation that is in linkage disequilibrium with the IL-1 inflammatory haplotype.

40. A method for treating or preventing the development of osteoporosis in a subject comprising the steps of: detecting one or mare alleles selected from the group consisting of: allele 4 of the 222/223 marker of IL-1A, allele 4 of the gz5/gz6 marker of IL-1A, allele 1 of the −889 marker of IL-1A, allele 1 of the +3954 marker of IL-1B, allele 2 of the −511 marker of IL-1B, allele 3 of the gaat.p33330 marker, allele 3 of the Y31 marker, allele 2 of +2018 of IL-1RN, allele 1 of +4845 of IL-1A, allele 3 of the 222/223 marker of IL-1A, allele 3 of the gz5/gz6 marker of IL-1A, allele 2 of the −889 marker of IL-1A, allele 2 of the +3954 marker of IL-1B, allele 1 of the −511 marker of IL-1B, allele 4 of the gaat.p33330 marker, allele 6 of the Y31 marker, allele 1 of +2018 of IL-1RN, allele 2 of +4845 of IL-1A, and allele 1 of the VNTR marker of IL-1RN; and administering to the subject a therapeutic that compensates for a causative mutation that is in linkage disequilibrium with the IL-1 inflammatory haplotype.

* * * * *

UNITED STATES PATENT AND TRADEMARK OFFICE
CERTIFICATE OF CORRECTION

PATENT NO. : 6,706,478 B2
DATED : March 16, 2004
INVENTOR(S) : Gordon W. Duff et al.

It is certified that error appears in the above-identified patent and that said Letters Patent is hereby corrected as shown below:

Column 81,
Line 63, replace "perdisposed" with -- predisposed --.

Column 84,
Line 30, replace "+2019" with -- +2018 --.

Column 85,
Line 31, replace "mom" with -- more --.

Column 86,
Line 22, replace "+2019" with -- +2018 --.
Line 46, replace "mare" with -- more --.

Signed and Sealed this

Ninth Day of November, 2004

JON W. DUDAS
*Director of the United States Patent and Trademark Office*